United States Patent
Blaskovich et al.

(10) Patent No.: US 7,829,737 B2
(45) Date of Patent: Nov. 9, 2010

(54) PROTEIN TYROSINE PHOSPHATASE INHIBITORS AND METHODS OF USE THEREOF

(75) Inventors: Mark Arnold Thomas Blaskovich, Bardon (AU); Ted Baughman, Bothell, WA (US); Thomas Little, Redmond, WA (US); Maher Qabar, Sammamish, WA (US); Lauri Marie Schultz, Batavia, WA (US); Feng Hong, Bellevue, WA (US); William Patt, Lawrence, KS (US); Gangadhar Nagula, Bothell, WA (US); Jennifer Lynn Gage, Kenmore, WA (US); James Jeffry Howbert, Bellevue, WA (US)

(73) Assignee: Ceptyr, Inc., Bothell, WA (US)

( * ) Notice: Subject to any disclaimer, the term of this patent is extended or adjusted under 35 U.S.C. 154(b) by 293 days.

(21) Appl. No.: 12/043,872

(22) Filed: Mar. 6, 2008

(65) Prior Publication Data
US 2008/0161592 A1 Jul. 3, 2008

Related U.S. Application Data

(62) Division of application No. 11/280,724, filed on Nov. 15, 2005, now Pat. No. 7,504,389.

(60) Provisional application No. 60/708,817, filed on Aug. 15, 2005, provisional application No. 60/628,233, filed on Nov. 15, 2004.

(51) Int. Cl.
C07F 9/02 (2006.01)
(52) U.S. Cl. .................................. 558/190; 558/89
(58) Field of Classification Search ............ 558/190, 558/89
See application file for complete search history.

(56) References Cited

U.S. PATENT DOCUMENTS

| | | | |
|---|---|---|---|
| 4,668,506 A | 5/1987 | Bawa | |
| 4,713,244 A | 12/1987 | Bawa | |
| 4,816,570 A | 3/1989 | Farquhar | |
| 4,931,279 A | 6/1990 | Bawa | |
| 4,968,788 A | 11/1990 | Farquhar | |
| 5,411,947 A | 5/1995 | Hostetler | |
| 5,463,092 A | 10/1995 | Hostetler | |
| 6,312,662 B1 | 11/2001 | Erion | |
| 6,348,572 B1 | 2/2002 | Desmarais | |
| 6,498,151 B2* | 12/2002 | Li et al. | 514/80 |
| 6,583,126 B2 | 6/2003 | Leblanc et al. | |
| 6,716,825 B2 | 4/2004 | Hostetler | |
| 6,752,981 B1 | 6/2004 | Erion | |
| 6,903,081 B2 | 6/2005 | Borch | |
| 2002/0004594 A1 | 1/2002 | Borch | |
| 2003/0225277 A1 | 12/2003 | Kopcho | |
| 2003/0229225 A1 | 12/2003 | Reddy | |
| 2004/0176330 A1 | 9/2004 | Dufresne et al. | |
| 2005/0171060 A1 | 8/2005 | Borch | |

FOREIGN PATENT DOCUMENTS

| | | |
|---|---|---|
| WO | WO 90/00555 | 1/1990 |
| WO | WO 94/08600 | 4/1994 |
| WO | WO 96/39831 | 12/1996 |
| WO | WO 98/20024 | 5/1998 |
| WO | WO 98/20156 | 5/1998 |
| WO | WO 99/46268 | 9/1999 |
| WO | WO 99/47529 | 9/1999 |
| WO | WO 00/17211 | 3/2000 |
| WO | WO 00/69889 | 11/2000 |
| WO | WO 01/18013 | 3/2001 |
| WO | WO 03/041729 | 5/2003 |
| WO | WO 03/090690 | 11/2003 |
| WO | WO 03/095665 | 11/2003 |
| WO | WO 2004/079012 | 9/2004 |

OTHER PUBLICATIONS

Andersen et al., "Structural and evolutionary relationships among Protein Tyrosine Phosphatase domains" *Mol. Cell Biol.* 21:7117-36 (2001).
Asante-Appiah et al., "The YRD motif is a major determinant of substrate and inhibitor specificity in T-cell protein-tyrosine phosphatase" *J. Biol. Chem.* 276(28):26036-26043 (2001).
Buchanan et al., "Preparation of Heterocyclyl Phosphotyrosine Derivatives as SH-2mediated Signal Transduction Inhibitors" CAS 131: 257875.

(Continued)

*Primary Examiner*—Rei-tsang Shiao
(74) *Attorney, Agent, or Firm*—Merchant & Gould

(57) ABSTRACT

The present invention provides compounds of Formula (I) and Formula (II) that are useful for modulating the biological activity of the protein tyrosine phosphatase-1b (PTP1B) enzyme. Compounds of this invention can be used to treat diseases and/or conditions in which the PTP1B enzyme is a factor. Such diseases and/or conditions include, but are not limited to, Type 1 diabetes, Type 2 diabetes, inadequate glucose tolerance, insulin resistance, obesity, hyperlipidemia, hypertriglyceridemia, hypercholesterolemia, low HDL levels, atherosclerosis, vascular restenosis, inflammatory bowel disease, pancreatitis, adipose cell tumors, adipose cell carcinoma, liposarcoma, dyslipidemia, cancer, and neurodegenerative diseases.

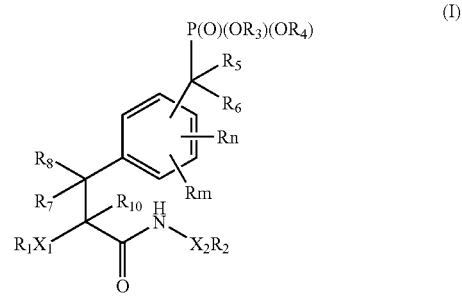

(I)

3 Claims, No Drawings

OTHER PUBLICATIONS

Charbonneau and Tonks, "1002 Protein phosphatases?" *Annu. Rev. Cell Biol.* 8:463-493 (1992).

Chemical Abstracts, "34-Amino Acids, Peptides, and Proteins" 131(19):735 (1999).

Cho et al., "Substrate specificities of catalytic fragments of protein tyrosine phosphatases (HPTP {beta}, LAR, and CD45) toward phosphotyrosylpeptide substates and thiophosphotyrosylated peptides as inhibitors" *Protein Sci.* 2:977-984 (1993).

Dang et al., "Synthesis of phosphonate 3-phthalidyl esters as prodrugs for potential intracellular delivery of phosphonates" *Bioorganic & Med. Chem Letters* 9:1505-1510 (1999).

Dechert et al., "Comparison of the specificity of bacterially espressed cytoplasmic protein-tyrosine phosphatases SHP and SH-PTP2 towards synthetic phosphopeptide substrates" *Eur. J. Biochem.* 231:673-681 (1995).

Desai et al., "Receptor Tyrosine Phosphatases are required for motor axon guidance in the Drosophila embryo" *Cell* 84:599-609 (1996).

Elchebly et al., "Increased insulin sensitivity and obesity resistance in mice lacking the protein tyrosine phosphatase-1B gene" *Science* 283:1544 (1999).

Erion et al., "Design, synthesis, and characterization of a series of cytochrome P450 3A-activated prodrugs (HepDirect Prodrugs) useful for targeting phosph(on)ate-based drugs to the liver" *J. Am. Chem. Soc.* 126:5154-5163 (2004).

Erion et al., "Liver-targeted drug delivery using HepDirect prodrugs" *Am. Soc. Pharm. & Exper. Ther.* 312(2):554-560 (2004) DOI:10.1124/jept.104.75903.

Farquhar et al., "5'-[4-(Pivalyloxy)-1,3,2-dioxaphosphorinan-2-yl]-2'-deoxy-5-fluorouridine: a membrane-permeating prodrug of 5-fluoro-2'-deoxyuridylic acid (FdUMP)" *J. Med. Chem.* 38:488-495 (1995).

Flint et al., "Multi-site phosphorylation of the protein tyrosine phosphatase, PTP1B: identification of cell cycle regulated and phorbol ester stimulated sites of phosphorylation" *EMBO J.* 12:1937-1946 (1993).

Freeman and Ross "3. Prodrug design for phosphatases and phosphonates" *Progress in Medicinal Chemistry* 34:112-147 (1997).

Fukada et al., "The reciprocal role of Egr-1 and Sp family proteins in regulation of the PTPIB promoter in response to the p210 Ber-Abl oncoprotein-tyrosine kinase" *J. Biol. Chem.* 276:25512-19 (2001).

Galic et al., "Regulation of insulin receptor signaling by the protein tyrosine phosphatase TCPTP" *Mol. Cell. Biol.* 23:2096-2108 (2003).

Griffiths et al., 2004, CAS: 141: 343429.

Harris et al., "Synthesis and antiviral evaluation of phosphoramidate derivatives of (E)-5-(2-bromovinyl)-2'-deoxyuridine" *Antiviral Chem & Chemo.* 12:293-300 (2001).

Heinonen et al., "T-cell protein tyrosine phosphatase deletion results in progressive systemic inflammatory disease" *Blood* 103:3457-3464 (2004).

Hostetler et al., "Enhanced oral absorption and antiviral activity of 1-O-octadecyl-sn-glycero-3-phospho-acyclovir and related compounds in hepatitis B virus infection, in vitro" *Biochem. Pharm.* 53:1815-1822 (1997).

Hostetler et al., "Lipid prodrugs of phosphonacids: greatly enhanced antiviral activity of 1-O-octadecyl-sn-glycero-3-phosphonoformate in HIV-1, HSV-1, and HCMV-infected cells, in vitro" *Antiviral Research* 31:59-67 (1996).

Kishihara et al., "Normal B lymphocyte development but impaired T cell maturation in CD45-exon6 protein tyrosine phosphatase-deficient mice" *Cell* 74:143-156 (1993).

Klaman et al., "Increased energy expenditure, decreased adiposity, and tissue-specific insulin sensitivity in protein-tyrosine phosphatase 1B-deficient mice" *Mol. Cell. Biol.* 20:5479 (2000).

Knaggs et al., "A QSAR study investigating the effect of L-alanine ester variation on the anti-HIV activity of some phosphoramidate derivatives of d4T" *Bioorganic & Med. Chem. Letters* 10:2075-2078 (2000).

LaMontagne et al., "Protein Tyrosine Phosphatase 1B antagonizes signaling by oncoprotein tyrosine kinase p210 ber-abl in vivo" *Mol. Cell. Biol.* 18:2965-75 (1998).

LaMontagne et al., "Protein tyrosine phosphatase PTP1B suppresses p210 ber-abl-induced transformation of Rat-1 fibroblasts and promotes differentiation of K562 cells" *Proc. Natl. Acad. Sci. USA* 95:14094-99 (1998).

Lau et al., 2001, CAS: 135: 61438.

Leblanc et al., 2001, CAS: 135: 76988.

McGuire et al. "Abnormal regulation of protein tyrosine phosphatase activities in skeletal muscle of insulin-resistant humans" *Diabetes* 40:939 (1991).

Meng et al., "Regulation of insulin signaling through reversible oxidation of the protein-tyrosine phosphatases TC45 and PTP1B" *J. Biol. Chem.*, 279:37716 (2004).

Myerovitch et al., "Hepatic phosphotyrosine phosphatase activity and its alterations in diabetic rats" *J. Clin. Invest.* 84:976 (1989).

Myers et al., "P-TEN, the tumor suppressor from human chromosome 10q23, is a dual-specificity phosphatase" *Proc. Natl. Acad. Sci. USA* 94:9052 (1997).

Myers et al., "TYK2 and JAK2 are substrates of Protein-tyrosine Phosphatase 1B" *J. Biol. Chem.* 276:47771 (2001).

Nishimura et al., 2002, CAS: 137: 232854.

Perkins et al., "*corkscrew* encodes a putative protein tyrosine phosphatase that functions to transducer the terminal signal fro mthe receptor tyrosine kinase torso" *Cell* 70:225-236 (1992).

Pingel and Thomas, "Evidence that the leukocyte-common antigen is required for antigen-induced T lymphocyte proliferation" *Cell* 58:1055-1065 (1989).

Ruzzene et al., "Specificity of T-cell protein tyrosine phosphatase toward phosphorylated synthetic peptides" *Eur. J. Biochem.* 211:289-295 (1993).

Salmeen et al., "Molecular basis for the dephosphorylation of the activation segment of the insulin receptor by Protein Tyrosine Phosphatase 1B" *Molecular Cell* 6:1401 (2000).

Schultz et al., "Mutations at the murine motheaten locus are within the hamatopoietic cell protein-tyrosine phosphatase (Heph) gene" *Cell* 73:1445-1454 (1993).

Simoncic et al., "The T cell protein tyrosine phosphatase is a negative regulator of Janus family kinases 1 and 3" *Curr. Biol. Mar 19*; 12(6):446-453 (2002).

Sredy et al., "Insulin resistance is associated with abnormal dephosphorylation of a synthetic phosphopeptide corresponding to the major autophosphorylation sites of the insulin receptor" *Metabolism* 44:1074 (1995).

Srivastva and Farquhar, "Bioreversible phosphate protective groups: synthesis and stability of model acyloxylmethyl phosphates" *Bioorganic Chemistry* 12, 118-129 (1984).

Tonks and Neel, "Combinatorial control of the specificity of protein phosphates" *Curr. Opin. Cell Biol.* 13:182 (2001).

Tonks, "Introduction: Protein tyrosine phosphatases" *Semin. Cell Biol.* 4:373-453 (1993).

Touw et al., "Signaling mechanisms of cytokine receptors and their perturbances in disease" *Mol. Cell. Endocrinol.* 160:109 (2000).

You-Ten et al., "Impaired bone marrow microenvironment and immune function in T cell protein tyrosine phosphatase-deficient mice" *J. Exp. Med.*, 186:683-693 (1997).

Zhang et al., "Protein tyrosine phosphatase substrate specificity; size and phosphotyrosine positioning requirements in peptide substrates" *Biochemistry* 33:2285-2290 (1994).

Supplementary Partial European Search Report dated Jan. 14, 2010 re: European Patent Application No. 05851631.

Burger (1991) Progress in Drug Research: Isoterism and bioisoterism in drug design. Birkhauser Verlag Basel, vol. 37; pp. 287-371.

\* cited by examiner

PROTEIN TYROSINE PHOSPHATASE INHIBITORS AND METHODS OF USE THEREOF

RELATED APPLICATIONS

This is a Divisional application of U.S. patent application Ser. No. 11/280,724 filed Nov. 15, 2005, which claims the benefit of U.S. Provisional Application No. 60/628,233, filed Nov. 15, 2004, and U.S. Provisional Application No. 60/708,817, filed Aug. 15, 2005, the entire contents of each are incorporated herein by reference.

FIELD OF THE INVENTION

This invention relates to the field of protein tyrosine phosphatase inhibition.

BACKGROUND OF THE INVENTION

This invention relates to a novel class of phosphonic acid derivatives that are inhibitors of PTP-1B.

Reversible protein tyrosine phosphorylation, coordinated by the action of protein tyrosine kinases (PTKs) that phosphorylate certain tyrosine residues in polypeptides, and protein tyrosine phosphatases (PTPs) that dephosphorylate certain phosphotyrosine residues, is a key mechanism in regulating many cellular activities. It is becoming apparent that the diversity and complexity of the PTPs and PTKs are comparable, and that PTPs are equally important in delivering both positive and negative signals for proper function of cellular machinery. Regulated tyrosine phosphorylation contributes to specific pathways for biological signal transduction, including those associated with cell division, cell survival, apoptosis, proliferation and differentiation. Defects and/or malfunctions in these pathways may underlie certain disease conditions for which effective means for intervention remain elusive, including for example, malignancy, autoimmune disorders, diabetes, obesity, and infection.

The protein tyrosine phosphatase (PTP) family of enzymes consists of more than 100 structurally diverse proteins in vertebrates, including human PTPs that have in common the conserved 250 amino acid PTP catalytic domain, but which display considerable variation in their non-catalytic segments (Charbonneau et al., 1992 *Annu. Rev. Cell Biol.* 8:463-493; Tonks, 1993 *Semin. Cell Biol.* 4:373-453; Andersen et al., (2001 *Mol. Cell. Biol.* 21:7117-36). This structural diversity presumably reflects the diversity of physiological roles of individual PTP family members, which in certain cases have been demonstrated to have specific functions in growth, development and differentiation (Desai et al., 1996 *Cell* 84:599-609; Kishihara et al., 1993 *Cell* 74:143-156; Perkins et al., 1992 *Cell* 70:225-236; Pingel et al., 1989 *Cell* 58:1055-1065; Schultz et al., 1993 *Cell* 73:1445-1454). The PTP family includes receptor-like and non-transmembrane enzymes that exhibit exquisite substrate specificity in vivo and that are involved in regulating a wide variety of cellular signaling pathways (Andersen et al., 2001 *Mol. Cell. Biol.* 21:7117; Tonks et al., 2001 *Curr. Opin. Cell Biol.* 13:182). PTPs thus participate in a variety of physiologic functions, providing a number of opportunities for therapeutic intervention in physiologic processes through alteration (i.e., a statistically significant increase or decrease) or modulation (e.g., up-regulation or down-regulation) of PTP activity.

Although recent studies have also generated considerable information regarding the structure, expression and regulation of PTPs, the nature of many tyrosine phosphorylated substrates through which the PTPs exert their effects remains to be determined. Studies with a limited number of synthetic phosphopeptide substrates have demonstrated some differences in the substrate selectivities of different PTPs (Cho et al., 1993 *Protein Sci.* 2: 977-984; Dechert et al., 1995 *Eur. J. Biochem.* 231:673-681). Analyses of PTP-mediated dephosphorylation of PTP substrates suggest that catalytic activity may be favored by the presence of certain amino acid residues at specific positions in the substrate polypeptide relative to the phosphorylated tyrosine residue (Salmeen et al., 2000 *Molecular Cell* 6:1401; Myers et al., 2001 *J. Biol. Chem.* 276:47771; Myers et al., 1997 *Proc. Natl. Acad. Sci. USA* 94:9052; Ruzzene et al., 1993 *Eur. J. Biochem.* 211:289-295; Zhang et al., 1994 *Biochemistry* 33:2285-2290). Thus, although the physiological relevance of the substrates used in these studies is unclear, PTPs display a certain level of substrate selectivity in vitro.

The PTP family of enzymes contains a common evolutionarily conserved segment of approximately 250 amino acids known as the PTP catalytic domain. Within this conserved domain is a unique signature sequence motif, $CX_5R$, that is invariant among all PTPs. In a majority of PTPs, an 11 amino acid conserved sequence ([I/V]HCXAGXXR[S/T]G (SEQ ID NO: 1)) containing the signature sequence motif is found. The cysteine residue in this motif is invariant in members of the family and is essential for catalysis of the phosphotyrosine dephosphorylation reaction. It functions as a nucleophile to attack the phosphate moiety present on a phosphotyrosine residue of the incoming substrate. It is well-known that if the cysteine residue is altered by site-directed mutagenesis to serine (e.g., in cysteine-to-serine or "CS" mutants) or alanine (e.g., cysteine-to-alanine or "CA" mutants), the resulting PTP is catalytically deficient but retains the ability to complex with, or bind, its substrate, at least in vitro.

One non-transmembrane PTP, PTP1B, recognizes several tyrosine-phosphorylated proteins as substrates, many of which are involved in human disease. For example, therapeutic inhibition of PTP1B in the insulin signaling pathway may serve to augment insulin action, thereby ameliorating the state of insulin resistance common in Type II diabetes patients. PTP1B acts as a negative regulator of signaling that is initiated by several growth factor/hormone receptor PTKs, including p210 Bcr-Abl (LaMontagne et al., 1998 *Mol. Cell. Biol.* 18:2965-75; LaMontagne et al., 1998 *Proc. Natl. Acad. Sci. USA* 95:14094-99), receptor tyrosine kinases, such as EGF receptor, PDGF receptor, and insulin receptor (IR) (Tonks et al., 2001 *Curr. Opin. Cell Biol.* 13:182-95), and JAK family members such as Jak2 and others (Myers et al., 2001 *J. Biol. Chem.* 276:47771-74), as well as signaling events induced by cytokines (Tonks et al., 2001). Activity of PTP1B is regulated by modifications of several amino acid residues, such as phosphorylation of Ser residues (Brautigan et al., 1993; Dadke et al., 2001; Flint et al., 1993), and oxidation of the active Cys residue in its catalytic motif (Lee et al., 1998; Meng et al., 2002) which is evolutionary conserved among protein tyrosine phosphatases and dual phosphatase family members (Andersen et al., 2001). In addition, changes in the expression levels of PTP1B have been noted in several human diseases, particularly those associated with disruption of the normal patterns of tyrosine phosphorylation.

Diabetes mellitus is a common, degenerative disease affecting 5-10% of the human population in developed countries, and in many countries, it may be one of the five leading causes of death. Approximately 2% of the world's population has diabetes, the overwhelming majority of cases (>90%) being type 2 diabetes and the remainder being type 1. In type 1 diabetes, which is frequently diagnosed in children or young adults, insulin production by pancreatic islet beta cells is destroyed. Type 2 diabetes, or "late onset" or "adult onset" diabetes, is a complex metabolic disorder in which cells and tissues cannot effectively use available insulin; in some cases insulin production is also inadequate. At the cellular level, the degenerative phenotype that may be characteristic of late onset diabetes mellitus includes, for example, impaired insulin secretion and decreased insulin sensitivity, i.e., an impaired response to insulin.

Studies have shown that diabetes mellitus may be preceded by or is associated with certain related disorders. For example, an estimated forty million individuals in the U.S. suffer from late onset impaired glucose tolerance (IGT). IGT patients fail to respond to glucose with increased insulin secretion. Each year a small percentage (5-10%) of IGT individuals progress to insulin deficient non-insulin dependent diabetes (NIDDM). Some of these individuals further progress to insulin dependent diabetes mellitus (IDDM). NIDDM and IDDM are associated with decreased release of insulin by pancreatic beta cells and/or a decreased response to insulin by cells and tissues that normally exhibit insulin sensitivity. Other symptoms of diabetes mellitus and conditions that precede or are associated with diabetes mellitus include obesity, vascular pathologies, and various neuropathies, including blindness and deafness.

Type 1 diabetes is treated with lifelong insulin therapy, which is often associated with undesirable side effects such as weight gain and an increased risk of hypoglycemia. Current therapies for type 2 diabetes (NIDDM) include altered diet, exercise therapy, and pharmacological intervention with injected insulin or oral agents that are designed to lower blood glucose levels. Examples of such presently available oral agents include sulfonylureas, biguanides, thiazolidinediones, repaglinide, and acarbose, each of which alters insulin and/or glucose levels. None of the current pharmacological therapies, however, controls the disease over its full course, nor do any of the current therapies correct all of the physiological abnormalities in type 2 NIDDM, such as impaired insulin secretion, insulin resistance, and excessive hepatic glucose output. In addition, treatment failures are common with these agents, such that multi-drug therapy is frequently necessary.

In certain metabolic diseases or disorders, one or more biochemical processes, which may be either anabolic or catabolic (e.g., build-up or breakdown of substances, respectively), are altered (e.g., increased or decreased in a statistically significant manner) or modulated (e.g., up- or down-regulated to a statistically significant degree) relative to the levels at which they occur in a disease-free or normal subject such as an appropriate control individual. The alteration may result from an increase or decrease in a substrate, enzyme, cofactor, or any other component in any biochemical reaction involved in a particular process. Altered (i.e., increased or decreased in a statistically significant manner relative to a normal state) PTP activity can underlie certain disorders and suggests a PTP role in certain metabolic diseases.

For example, disruption of the murine PTP1B gene homolog in a knock-out mouse model results in PTP1B$^{-/-}$ mice exhibiting enhanced insulin sensitivity, decreased levels of circulating insulin and glucose, and resistance to weight gain even on a high-fat diet, relative to control animals having at least one functional PTP1B gene (Elchebly et al., *Science* 283:1544 (1999)). Insulin receptor hyperphosphorylation has also been detected in certain tissues of PTP1B deficient mice, consistent with a PTP1B contribution to the physiologic regulation of insulin and glucose metabolism (Id.). PTP1B-deficient mice exhibit decreased adiposity (reduced fat cell mass but not fat cell number), increased basal metabolic rate and energy expenditure, and enhanced insulin-stimulated glucose utilization (Klaman et al., 2000 *Mol. Cell. Biol.* 20:5479). Additionally, altered PTP activity has been correlated with impaired glucose metabolism in other biological systems (e.g., McGuire et al., 1991 *Diabetes* 40:939; Myerovitch et al., 1989 *J. Clin. Invest.* 84:976; Sredy et al., 1995 *Metabolism* 44:1074), including PTP involvement in biological signal transduction via the insulin receptor (see, e.g., WO 99/46268 and references cited therein).

An integration of crystallographic, kinetic, and PTP1B-peptide binding assays illustrated the interaction of PTP1B and insulin receptor (IR) (Salmeen et al., 2000 *Mol. Cell.* 6:1401-12). The insulin receptor (IR) comprises two extracellular α subunits and two transmembrane β subunits. Activation of the receptor results in autophosphorylation of tyrosine residues in both β subunits, each of which contains a protein kinase domain. Extensive interactions that form between PTP1B and insulin receptor kinase (IRK) encompass tandem pTyr residues at 1162 and 1163 of IRK, such that pTyr-1162 is located in the active site of PTP1B (id.). The Asp/Glu-pTyr-pTyr-Arg/Lys motif has been implicated for optimal recognition by PTP1B for IRK. This motif is also present in other receptor PTKs, including Trk, FGFR, and Axl. In addition, this motif is found in the JAK family of PTKs, members of which transmit signals from cytokine receptors, including a classic cytokine receptor that is recognized by the satiety hormone leptin (Touw et al., 2000 *Mol. Cell. Endocrinol.* 160:1-9).

Changes in the expression levels of PTP1B have been observed in several human diseases, particularly in diseases associated with disruption of the normal patterns of tyrosine phosphorylation. For example, the expression of PTP1B is induced specifically by the p210 Bcr-Abl oncoprotein, a PTK that is directly responsible for the initial manifestations of chronic myelogenous leukemia (CML) (LaMontagne et al., 1998 *Mol. Cell. Biol.* 18:2965-75; LaMontagne et al., 1998 *Proc. Natl. Acad. Sci. USA* 95:14094-99). Expression of PTPB1 in response to this oncoprotein is regulated, in part, by transcription factors Sp1, Sp3, and Egr-1 (Fukada et al., 2001 *J. Biol. Chem.* 276:25512-19). These transcription factors have been shown to bind to a p210 Bcr-Abl responsive sequence (PRS) in the human PTP1B promoter, located between −49 to −37 base pairs from the transcription start site, but do not appear to mediate certain additional, independent PTP1B transcriptional events, for which neither transcription factor(s) nor transcription factor recognition element(s) have been defined (id.).

Another protein tyrosine phosphatase enzyme, T-cell protein tyrosine phosphatase, or TCPTP, dephosphorylates JAK1 and JAK3. TCPTP appears to have a role in the regulation of immune homeostasis. TCPTP is also known to dephosphorylate the EGF receptor, and the adapter protein p52shc. TCPTP may also play a role in certain T-cell malignancies. (See, for example, Simoncic et al., 2002 *Curr. Biol.* March 19; 12(6): 446-45; Heinonen et al., 2004 *Blood,* 103:3457-3464; You-Ten et al., 1997 *J. Exp. Med.,* 186:683-693). TCPTP also may play a role in insulin-signaling. (See Tonks et al., 2004 *JBC,* 279:37716; and 2003 *Mol. Cell. Biol.* 23:2096).

Currently, therefore, desirable goals for therapeutic regulation of biological signal transduction include modulation of PTP1B-mediated cellular events including, inter alia, inhibition or potentiation of interactions among PTP1B-binding molecules, substrates and binding partners, or of other agents that regulate PTP1B activities. Accordingly, a need exists in the art for an improved ability to intervene in the regulation of phosphotyrosine signaling, including regulating PTP1B by altering PTP1B catalytic activity, PTP1B binding to PTP1B substrate molecules, and/or PTP1B-encoding gene expression. An increased ability to so regulate PTP1B may facilitate the development of methods for modulating the activity of proteins involved in phosphotyrosine signaling pathways and for treating conditions associated with such pathways. The present invention fulfills these needs and further provides other related advantages.

SUMMARY OF THE INVENTION

The present invention provides compounds of Formula (I) or Formula (II):

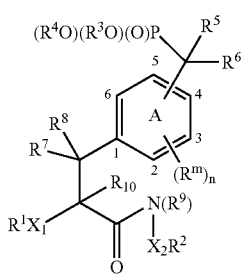

(I)

wherein:

$X_1$ is a linker group or is absent;

$X_2$ is H, absent or a linker group, preferably selected from an optionally substituted straight-chained or branched aliphatic, preferably comprising 1 to 8 carbons, optionally containing 1 or more double or triple bonds, wherein one or more of the carbons are optionally replaced by R* wherein R* is optionally substituted cycloalkyl, heterocycloalkyl, aryl or heteroaryl; —C(O)—, —C(O)C(O)—, —C(O)NR$^{11}$—, —C(O)NR$^{11}$NR$^{12}$—, —C(O)O—, —OC(O)—, —NR$^{11}$CO$_2$—, —O—, —NR$^{11}$C(O)NR$^{12}$—, —OC(O)NR$^{11}$—, —NR$^{11}$NR$^{12}$—, —NR$^{11}$C(O)—, —S—, —SO—, —SO$_2$—, —NR$^{11}$—, —SO$_2$NR$^{11}$— or —NR$^{11}$SO$_2$—, wherein R$^{11}$ and R$^{12}$ are independently selected from H and optionally substituted aliphatic, cycloalkyl, heterocycloalkyl, aryl or heteroaryl; or $X_2$ is optionally substituted cycloalkyl, heterocycloalkyl, aryl or heteroaryl; —C(O)—, —C(O)C(O)—, —C(O)NR$^{11}$—, —C(O)NR$^{11}$N$^{12}$, —C(O)O—, —OC(O)—, —NR$^{11}$CO$_2$—, —O—, —NR$^{11}$C(O)NR$^{12}$—, —OC(O)NR$^{11}$, NR$^{11}$NR$^{12}$—, —NR$^{11}$C(O)—, —S—, —SO—, —SO$_2$—, —NR$^{11}$—, —SO$_2$NR$^{11}$— or —NR$^{11}$SO$_2$—; provided that when $X_1$ is —NH—, $X_2$ is not —CH$_2$C(O)— or substituted —CH$_2$C(O)—;

R$^1$ is H or optionally substituted C$_{1-8}$ aliphatic, cycloalkyl, heterocycloalkyl, aryl or heteroaryl;

R$^2$ is H or optionally substituted C$_{1-8}$ aliphatic, cycloalkyl, heterocycloalkyl, aryl or heteroaryl; or R$_2$ is absent when $X_2$ is H;

R$^3$ and R$^4$ are independently H, alkyl or C$_{5-6}$ aryl;

R$^5$ and R$^6$ are independently H or halo;

R$^7$ and R$^8$ are independently H, —OR$^{23}$ or —NHR$^{23}$; or optionally substituted aliphatic, cycloalkyl, heterocycloalkyl, aryl or heteroaryl; or together form an optionally substituted ring comprising 3 to 7 carbon or heteroatoms;

R$^9$ is H or C$_{1-3}$ alkyl;

R$^{10}$ is H or C$_{1-3}$ alkyl; or R$^8$ and R$^{10}$ together form an optionally substituted ring comprising 3 to 7 carbon or heteroatoms; and each R$^m$ is independently H, halo, —OH, —NO$_2$, —CN; optionally substituted C$_{1-3}$ alkyl; —OR$^{23}$, —C(O)R$^{23}$, —C(O)OR$^{23}$, —C(O)N(R$^{23}$)(R$^{24}$), —OC(O)R$^{23}$, —OC(O) OR$^{23}$, —OC(O)N(R$^{23}$)(R$^{24}$), —N(R$^{23}$)(R$^{24}$), —S(O)$_2$R$^{23}$, —S(O)R$^{23}$, SR$^{23}$, —S(O)$_2$N(R$^{23}$)(R$^{24}$); NR$^{23}$C(O)R$^{24}$, —NR$^{23}$C(O)OR$^{24}$, —NR$^{23}$SOOR$^{24}$, —NR$^{23}$C(O)N(R$^{24}$) (R$^{25}$) or —NR$^{23}$SO$_2$N(R$^{24}$)(R$^{25}$); where R$^{23}$, R$^{24}$ and R$^{25}$ are each independently H, C$_{1-4}$ alkyl or optionally substituted 3 to 8 membered cycloalkyl, heterocycloalkyl, aryl or heteroaryl; or two adjacent R$^m$ groups together form an optionally substituted aromatic or non-aromatic ring comprising 5 to 7 carbon or heteroatoms; where n is 0, 1, 2, 3 or 4; or R$^m$ and R$^7$ together form an optionally substituted aromatic or non-aromatic ring;

wherein each of the phenyl ring A carbon atoms 2-6 is optionally replaced by N; or any pair of adjacent phenyl ring A carbons atoms 2-6 is optionally replaced by S, N or O; provided that in no instance is the phenyl ring A carbon atom that is substituted with the phosphonate group replaced; and a pharmaceutically acceptable salt, ester or prodrug thereof.

Also included in the present invention are compounds of Formula II (IIa-IIe):

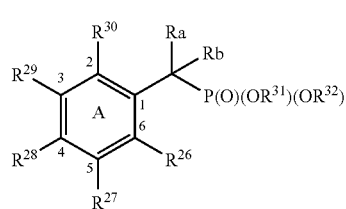

(IIa)

wherein:

R$_a$ and R$_b$ are independently H or halogen;

R$^{26}$, R$^{27}$, R$^{29}$ and R$^{30}$ are each independently H, halo, —OH, —NO$_2$, —CN, —CF$_3$, —CHF$_2$, —CH$_2$CH$_3$, —CH$_2$CF$_3$, —CF$_2$CF$_3$, —CH$_2$Cl, —CH$_2$OH, —CH$_2$CH$_2$OH, —CH$_2$NH$_2$, —CH$_2$CH$_2$NH$_2$, —CH$_2$SO$_2$CH$_3$, —OR$^{23}$, —C(O)R$^{23}$, —C(O)OR$^{23}$, —C(O) N(R$^{23}$)(R$^{24}$), —OC(O)R$^{23}$, —OC(O)OR$^{23}$, —OC(O)N(R$^{23}$) (R$^{24}$), —N(R$^{23}$)(R$^{24}$), —S(O)$_2$R$^{23}$, —S(O)R$^{23}$, —SR$^{23}$, —S(O)$_2$N(R$^{23}$)(R$^{24}$), NR$^{23}$C(O)R$^{24}$, —NR$^{23}$C(O)OR$^{24}$, —NR$^{23}$SOOR$^{24}$, —NR$^{23}$C(O)N(R$^{24}$)(R$^{25}$), —NR$^{23}$SO$_2$R$^{24}$ or —NR$^3$SO$_2$N(R$^{24}$)(R$^{25}$); or optionally substituted C$_{1-6}$ alkyl, C$_{1-6}$ alkoxy or aryl; where R$^{23}$, R$^{24}$ and R$^{25}$ are each independently H, C$_{1-4}$ alkyl or C$_{3-8}$ cycloalkyl, heterocloalkyl, aryl or heteroaryl;

R$^{31}$ and R$^{32}$ are each independently H, alkyl or C$_{5-6}$ aryl;

R$^{28}$ is H, halogen, —CN, —[CH$_2$]$_n$—[C(H)$_{3-p}$]$_x$(R$^{33}$)$_g$, —C(O)OH, —C(O)(CH$_2$)$_n$NH$_2$, —C(O)NH(CH$_2$)$_n$R$^{33}$, —C=N—N—S(O)$_2$R$^{33}$, —(CH$_2$)$_n$—CH(R$^{34}$)(R$^{35}$) or —CHNR$^{34}$—; or R$^{28}$ taken together with either R$^{27}$ or R$^{29}$ form an optionally substituted ring comprising 3 to 8 carbon or heteroatoms;

each R$^{33}$ is independently H, halogen, —C(O)OR$^{39}$, —OH, —CN, —N=N—N, —N(R$^{37}$)(R$^{38}$), —C(O)NH (CH$_2$)$_n$R$^{39}$, —C(R$^{39}$)(NH$_2$)C(O)OR$^{39}$, —CH$_2$R$^{35}$ or —CH (R$^{35}$)NHS(O)$_2$R$^{39}$; or an optionally substituted cycloalkyl, heterocycloalkyl, aryl or heteroaryl;

R$^{34}$ is H or —N(R$^{37}$)(R$^{38}$);

R$^{35}$ is H, —C(O)R$^{34}$, —C(O)OR$^{39}$ or —N(NH$_2$)C(O)NH (CH$_2$)$_n$Ph;

R$^{37}$ and R$^{38}$ are each independently H, —C(O)OR$^{39}$, —C(O)cycloalkyl-Ph, —S(O)$_2$R$^{39}$, —C(O)R$^9$, —OC(O) R$^{39}$—C(O)(CH$_2$)$_q$R$^{39}$, —S(O)$_2$, —S(O)$_2$NHR$^{39}$, —S(O)$_2$N (R$^{44}$)(R$^{39}$), —N(R$^{39}$)(R$^{44}$), —C(O)N(R$^{44}$)(R$^{39}$) or —NHC (O)N(R$^{44}$)(R$^{39}$); or optionally substituted C$_{1-6}$ alkyl, C$_{3-8}$ cycloalkyl, $C_{5-8}$ aryl, 3 to 8 membered heterocycloalkyl or 5 to 8 membered heteroaryl; and $R^{39}$ and $R^{44}$ are each independently H or optionally substituted $C_{1-6}$ alkyl, $C_{3-8}$ cycloalkyl, $C_{5-8}$ aryl, 3 to 8 membered heterocycloalkyl or 5 to 8 membered heteroaryl;

wherein each of the phenyl ring A carbon atoms 2-6 including its respective substituents is optionally replaced by N; or any pair of adjacent phenyl ring A carbons atoms 2-6 and their respective substituents are optionally replaced by S, N or O;

wherein n is an integer from 0 to 4; m is 0, 1 or 2; p is an integer from 1 to 3; q is an integer from 0 to 6; and x is either 0 or 1, provided that when x is 0, p is 1; and a pharmaceutically acceptable salt, ester or prodrug thereof.

Compounds within the present invention are compounds of Formula IIb:

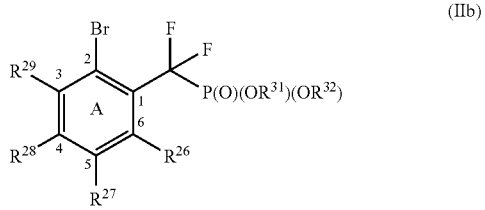

(IIb)

wherein $R^{26}$, $R^{27}$, $R^{28}$, $R^{29}$, $R^{31}$ and $R^{32}$ are as defined above; each of the phenyl ring A carbon atoms 3-6 including its respective substituents is optionally replaced by N; or any pair of adjacent phenyl ring A carbons atoms 3-6 and their respective substituents are optionally replaced by S, N or O; and a pharmaceutically acceptable salt, ester or prodrug thereof.

Additional compounds within the present invention are compounds of the following Formula IIc:

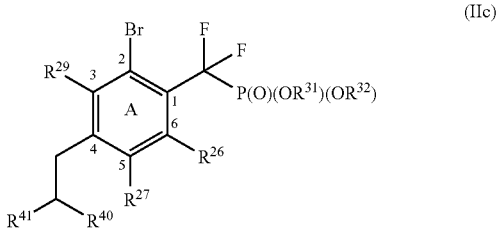

(IIc)

wherein $R^{26}$, $R^{27}$, $R^{29}$, $R^{31}$ and $R^{32}$ are as defined above for Formula IIa;

$R^{40}$ is H, alkyl, alkylene, —C(O)OR$^{39}$, —C(O)N(R$^{37}$)(R$^{38}$) or —N(NH$_2$)C(O)NH(CH$_2$)$_n$Ph;

$R^{41}$ is —N(R$^{37}$)(R$^{38}$); wherein $R^{37}$ and $R^{38}$ are as described above for Formula Ia; and each of the phenyl ring A carbon atoms 3, 5 or 6 including its respective substituents is optionally replaced by N; or phenyl ring A carbons atoms 5 and 6 together and their respective substituents is optionally replaced by an S, N or O;

and a pharmaceutically acceptable salt, ester or prodrug thereof.

Further compounds within the present invention are compounds of the following Formula IId:

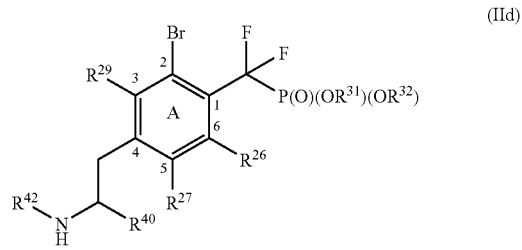

(IId)

wherein $R^{26}$, $R^{27}$ and $R^{29}$ are as defined above for Formula IIa;

$R^{31}$ and $R^{32}$ are each independently H, alkyl or $C_{5-6}$ aryl;

$R^{40}$ is as defined above for Formula IIc; $R^{42}$ is H, optionally substituted $C_{1-3}$ alkyl, —C(O)OR$^{39}$, —OC(O)R$^{39}$, —C(O)N(R$^{44}$)(R$^{39}$), —C(O)cyclopropyl-Ph, —S(O)$_2$R$^{39}$, —S(O)$_2$NHR$^{39}$ or —C(O)(CH$_2$)$_q$R$^{39}$; and each of the phenyl ring A carbon atoms 3, 5 or 6 including its respective substituents are optionally replaced by N; or phenyl ring A carbons atoms 5 and 6 together and their respective substituents are optionally replaced by an S, N or O;

wherein $R^{39}$ is as defined above for Formula IIa; and a pharmaceutically acceptable salt, ester or prodrug thereof.

Additional compounds within the present invention are compounds of the following Formula IIe:

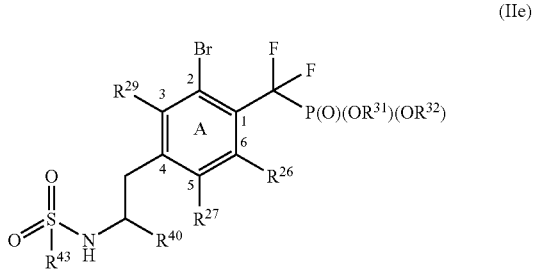

(IIe)

wherein $R^{26}$, $R^{27}$, $R^{29}$ and $R^{40}$ are as defined above for Formula IId;

$R^{31}$ and $R^{32}$ are each independently H, alkyl or $C_{5-6}$ aryl; $R^{43}$ is H, —NHR$^{39}$ or is R$^{39}$; wherein $R^{39}$ is H or optionally substituted $C_{1-6}$ alkyl, $C_{3-8}$ cycloalkyl, 3-8 member heterocycloalkyl, $C_{3-8}$ aryl or 3 to 8 membered heteroaryl; and each of the phenyl ring A carbon atoms 3, 5 or 6 including its respective substituents is optionally replaced by N; or phenyl ring A carbons atoms 5 and 6 together and their respective substituents are optionally replaced by S, N or O; and a pharmaceutically acceptable salt, ester or prodrug thereof.

The present invention additionally provides pharmaceutical compositions comprising compounds of Formula (I) or (IIa-e), or a pharmaceutically acceptable salt, ester or prodrug thereof, in combination with a pharmaceutically effective diluent or carrier. For simplification, compounds of Formula IIa-IIe are referred to herein as Formula II.

The present invention also provides methods of treating, preventing, or controlling PTP-mediated diseases, including but not limited to, Type 1 diabetes, Type 2 diabetes, inadequate (impaired) glucose tolerance, insulin resistance, obesity, hyperlipidemia, hypertriglyceridemia, hypercholesterolemia, low HDL levels, atherosclerosis, vascular restenosis, inflammatory bowel disease, pancreatitis, adipose cell tumors, adipose cell carcinoma, liposarcoma, dyslipidemia, cancer, and neurodegenerative disease, where the method comprises administration of an effective, or PTP-modulating, amount of a pharmaceutical composition described herein. In addition, the invention comprises methods of increasing the insulin sensitivity of a mammal comprising administering to said mammal an insulin-sensitizing amount of a compound of Formula (I) or Formula (II), or a pharmaceutically acceptable salt, ester, or prodrug thereof.

The present invention provides methods of modulating the biological activity of PTPs, in particular a PTP1B enzyme comprising contacting PTP1B with a compound of Formula (I) or Formula (II), or a pharmaceutically acceptable salt, ester or prodrug thereof.

In addition, the invention provides a method of modulating the biological activity of PTP1B in a mammal comprising administering a PTP1B-modulating amount of a compound of Formula (I) or Formula (II), or a pharmaceutically acceptable salt, ester or prodrug thereof. Further included are methods of treating a mammal having a TCPTP-mediated disease, such as, for example, cutaneous T-cell Lymphoma (CTCL) which is also known as Mycosis Fungoides and the Sezary Syndrome, by modulating the biological activity of TC-PTP. Such treatment comprises administering a TCPTP-modulating effective amount of a compound of Formula (I) or Formula (II), or a pharmaceutically acceptable salt, ester or prodrug thereof.

The present invention also provides methods of modulating the biological activity of a TCPTP (T-cell protein tyrosine phosphatase) enzyme comprising contacting TCPTP with a compound of Formula (I) or Formula (II), or a pharmaceutically acceptable salt, ester or prodrug thereof.

The present invention also provides complexes comprising PTP1B or TCPTP and a compound of Formula (I) or Formula (II).

DETAILED DESCRIPTION

As used herein, the following definitions shall apply unless otherwise indicated.

The phrase "optionally substituted" is used interchangeably with the phrase "substituted or unsubstituted." Unless otherwise indicated, an optionally substituted group may have a substituent at each substitutable position of the group, and each substitution is independent of any other. Also, combinations of substituents or variables are permissible only if such combinations result in stable compounds. In addition, unless otherwise indicated, functional group radicals are independently selected. Where "optionally substituted" modifies a series of groups separated by commas (e.g., "optionally substituted A, B or C"; or "A, B or C optionally substituted with"), it is intended that each of the groups (e.g., A, B and C) is optionally substituted.

The term "PTP1B" means protein tyrosine phosphatase enzyme 1B. PTP1B as used herein refers to the enzyme in its wild-type or natural form, or can refer to any isolated or purified form. Further, the term PTP1B means either the enzyme in its full-length form or in a truncated form. When compounds of the invention are used for in vitro studies, the PTP1B enzyme can be truncated or full-length, provided the catalytic domain is intact and its activity and protein folding characteristics have not been altered from its natural state. Such forms are commercially available or readily obtained using standard methods in the art, and described in the literature.

The term "aliphatic" or "aliphatic group" as used herein means a straight-chain or branched $C_{1-12}$ hydrocarbon chain that is completely saturated or that contains one or more units of unsaturation, or a monocyclic $C_{3-8}$ hydrocarbon or bicyclic $C_{8-12}$ hydrocarbon that is completely saturated or that contains one or more units of unsaturation, but which is not aromatic (also referred to herein as "carbocycle" or "cycloalkyl"), that has a single point of attachment to the rest of the molecule wherein any individual ring in said bicyclic ring system has 3-7 members. For example, suitable aliphatic groups include, but are not limited to, linear or branched alkyl, alkenyl, alkynyl groups and hybrids thereof such as (cycloalkyl)alkyl, (cycloalkenyl)alkyl or (cycloalkyl)alkenyl.

The terms "alkyl," "alkoxy," "hydroxyalkyl," "alkoxyalkyl" and "alkoxycarbonyl," used alone or as part of a larger moiety include both straight and branched chains containing one to twelve carbon atoms. The terms "alkenyl" and "alkynyl" used alone or as part of a larger moiety shall include both straight and branched chains containing two to twelve carbon atoms.

The terms "haloalkyl," "haloalkenyl" and "haloalkoxy" means alkyl, alkenyl or alkoxy, as the case may be, substituted with one or more halogen atoms. The term "halogen" or "halo" means F, Cl, Br or I.

The term "heteroatom" means nitrogen, oxygen, or sulfur and includes any oxidized form of nitrogen and sulfur, and the quaternized form of any basic nitrogen.

The term "aryl" used alone or in combination with other terms, refers to monocyclic, bicyclic or tricyclic carbocyclic ring systems having a total of five to fourteen ring members, wherein at least one ring in the system is aromatic and wherein each ring in the system contains 3 to 8 ring members. The term "aryl" may be used interchangeably with the term "aryl ring". The term "aralkyl" refers to an alkyl group substituted by an aryl. The term "aralkoxy" refers to an alkoxy group substituted by an aryl.

As used herein, where a ring is defined to contain or comprise x to y members, it is understood that the total number of member atoms (e.g., carbon or heteroatoms) making up the ring is x, y or any integer between x and y. By way of example, a ring comprising 3 to 8 carbon or heteroatoms may be ring containing 3, 4, 5, 6, 7 or 8 ring members.

The term "heterocycloalkyl," "heterocycle," "heterocyclyl" or "heterocyclic" as used herein means monocyclic, bicyclic or tricyclic ring systems having 5, 6, 7, 8, 9, 10, 11, 12, 13 or 14 ring members in which one or more ring members is a heteroatom, wherein each ring in the system contains 3, 4, 5, 6, 7 or 8 ring members and is non-aromatic.

The term "heteroaryl," used alone or in combination with other terms, refers to monocyclic, bicyclic and tricyclic ring systems having a total of 5, 6, 7, 8, 9, 10, 11, 12, 13 or 14 ring members, and wherein: 1) at least one ring in the system is aromatic; 2) at least one ring in the system contains one or more heteroatoms; and 3) each ring in the system contains 3, 4, 5, 6 or 7 ring members. The term "heteroaryl" may be used interchangeably with the term "heteroaryl ring" or the term "heteroaromatic". Examples of heteroaryl rings include, but are not limited to, 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 1-pyrazolyl, 3-pyrazolyl, 4-pyrazolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indazolyl, isoindolyl, acridinyl, and benzoisoxazolyl. The term "heteroaralkyl" refers to an alkyl group substituted by a heteroaryl. The term "heteroarylalkoxy" refers to an alkoxy group substituted by a heteroaryl.

An aryl (including aralkyl, aralkoxy, aryloxyalkyl and the like) or heteroaryl (including heteroaralkyl, heteroarylalkoxy and the like) group may contain one or more substituents. Suitable substituents on an unsaturated carbon atom of an aryl, heteroaryl, aralkyl or heteroaralkyl group are selected from halogen; haloalkyl; —CF$_3$; —R; —OR; —SR; 1,2-methylenedioxy; 1,2-ethylenedioxy; protected OH (such as acyloxy); phenyl (Ph); Ph substituted with R; —O(Ph); —O-(Ph) substituted with R; —CH$_2$(Ph); —CH$_2$(Ph) substituted with R; —CH$_2$CH$_2$(Ph); —CH$_2$CH$_2$(Ph) substituted with R; —NO$_2$; —CN; —N(R)$_2$; —NRC(O)R; —NRC(O)N(R)$_2$; —NRCO$_2$R; —NRNRC(O)R; —NR—NRC(O)N(R)$_2$; —NRNRCO$_2$R; —C(O)C(O)R; —C(O)CH$_2$C(O)R; —CO$_2$R; —C(O)R; —C(O)N(R)$_2$; —OC(O)N(R)$_2$; —S(O)$_2$R; —SO$_2$N(R)$_2$; —S(O)R; —NRSO$_2$N(R)$_2$; —NRSO$_2$R; —C(=S)N(R)$_2$; —C(=NH)—N(R)$_2$; —(CH$_2$)$_y$NHC(O)R; —(CH$_2$)$_y$R; —(CH$_2$)$_y$NHC(O)NHR; —(CH$_2$)$_y$NHC(O)OR; —(CH$_2$)$_y$NHS(O)R; —(CH$_2$)$_y$NHSO$_2$R; or —(CH$_2$)$_y$NHC(O)CH((V)$_z$—R)(R) wherein each R is independently selected from hydrogen, optionally substituted aliphatic (preferably C$_{1-6}$), an unsubstituted heteroaryl or heterocyclic ring (preferably C$_{5-6}$), phenyl (Ph), —O(Ph), or —CH$_2$(Ph)-CH$_2$(Ph), wherein y is 0-6; z is 0-1; and V is a linker group. When R is aliphatic, it may be substituted with one or more substituents selected from —NH$_2$, —NH(C$_{1-4}$ aliphatic), —N(C$_{1-4}$ aliphatic)$_2$, —S(O)(C$_{1-4}$ aliphatic), —SO$_2$(C$_{1-4}$ aliphatic), halogen, (C$_{1-4}$ aliphatic), —OH, —O—(C$_{1-4}$ aliphatic), —NO$_2$, —CN, —CO$_2$H, —CO$_2$(C$_{1-4}$ aliphatic), —O(halo C$_{1-4}$ aliphatic) or -halo(C$_{1-4}$ aliphatic); wherein each C$_{1-4}$ aliphatic is unsubstituted.

An aliphatic group or a non-aromatic heterocyclic ring may contain one or more substituents. Suitable substituents on a saturated carbon of an aliphatic group or of a non-aromatic heterocyclic ring are selected from those listed above for the unsaturated carbon of an aryl or heteroaryl group and the following: =O, =S, =NNHR, =NN(R)$_2$, =N—, =NNHC(O)R, =NNHCO$_2$(alkyl), =NNHSO$_2$(alkyl), or =NR, where each R is independently selected from hydrogen or an optionally substituted aliphatic (preferably C$_{1-6}$). When R is aliphatic, it may be substituted with one or more substituents selected from —NH$_2$, —NH(C$_{1-4}$ aliphatic), —N(C$_{1-4}$ aliphatic)$_2$, halogen, —OH, —O—(C$_{1-4}$ aliphatic), —NO$_2$, —CN, —CO$_2$H, —CO$_2$(C$_{1-4}$ aliphatic), —O(halo C$_{1-4}$ aliphatic), or -halo(C$_{1-4}$ aliphatic); wherein each C$_{1-4}$ aliphatic is unsubstituted.

Substituents on a nitrogen of a non-aromatic heterocyclic ring are selected from —R, —N(R)$_2$, —C(O)R, —C(O)OR, —C(O)C(O)R, —C(O)CH$_2$C(O)R, —SO$_2$R, —SO$_2$N(R)$_2$, —C(=S)N(R)$_2$, —C(=NH)—N(R)$_2$ or —NRSO$_2$R; wherein each R is independently selected from hydrogen, an optionally substituted aliphatic (preferably C$_{1-6}$), optionally substituted phenyl (Ph), optionally substituted —O(Ph), optionally substituted —CH$_2$(Ph), optionally substituted —CH$_2$CH$_2$(Ph), or an unsubstituted heteroaryl or heterocyclic ring (preferably 5-6 membered). When R is a C$_{1-6}$ aliphatic group or a phenyl ring, it may be substituted with one or more substituents selected from —NH$_2$, —NH(C$_{1-4}$ aliphatic), —N(C$_{1-4}$ aliphatic)$_2$, halogen, —(C$_{1-4}$ aliphatic), —OH, —O—(C$_{1-4}$ aliphatic), —NO$_2$, —CN, —CO$_2$H, —CO$_2$(C$_{1-4}$ aliphatic), —O(halo C$_{1-4}$ aliphatic) or -halo(C$_{1-4}$ aliphatic); wherein each C$_{1-4}$ aliphatic is unsubstituted.

The term "linker group" or "linker" means an organic moiety that connects two parts of a compound. Linkers include alkylidene chain that is a saturated or unsaturated, straight or branched, C$_{1-8}$ carbon chain which is optionally substituted, and wherein one or more saturated carbons of the chain are optionally replaced by R* wherein R* is —C(O)—, —C(O)C(O)—, —C(O)NR—, —C(O)NRNR—, —C(O)O—, —OC(O)—, —NRCO$_2$—, —O—, —NRC(O)NR—, —OC(O)NR—, —NRNR—, —NRC(O)—, —S—, —SO—, —SO$_2$—, —NR—, —SO$_2$NR—, or —NRSO$_2$—; or an optionally substituted cycloalkyl, heterocycloalkyl, aryl or heteroaryl; wherein R is selected from hydrogen or C$_{1-4}$ aliphatic; wherein C$_{1-4}$ aliphatic is unsubstituted. In one embodiment, two or more non-adjacent saturated carbons of the chain are optionally replaced by R*. Optional substituents on the alkylidene chain are as described above for an aliphatic group. Alternatively, the linker group is R*. Additional linkers include aryl and heteroaryl.

For compounds of Formula (I) or Formula (II), the phenyl ring A can be optionally modified to be a heteroaryl ring by one, two, or three applications of either or both of the following alterations: 1) any one or more of the phenyl ring A carbon atoms 2-6 including its respective substituent is replaced by N; and/or 2) any pair of adjacent phenyl ring A carbons atoms 2-6 and their respective substituents are replaced by an S or O or N. Such heteroaryl rings preferably include, but are not limited to, oxazoles, isoxazoles, imidazoles, thiazoles, isothiazoles, pyrazoles, thiophenes, furans, pyrroles, pyridines, pyrimidines, pyrazines, and pyridazines. Preferably, ring A is a phenyl, pyridine, thiophene, furan, pyrrole, oxazole, isoxazole, thiazole or an isothiazole. More preferably, ring A is a phenyl, pyridine, thiophene, furan or pyrrole. Even more preferably, ring A is a phenyl, pyridine or thiophene. Most preferred is where ring A is phenyl.

For compounds of Formula II where $R^{28}$ is taken together with either $R^{27}$ or $R^{29}$ they form an optionally substituted 3-8 membered, or preferably 5-8 membered, cycloalkyl, aryl, heterocycloalkyl or heteroaryl.

The term "treatment" refers to any treatment of a pathologic condition in a mammal, particularly a human, and includes: (i) preventing the pathologic condition from occurring in a subject which may be predisposed to the condition but has not yet been diagnosed with the condition and, accordingly, the treatment constitutes prophylactic treatment for the disease condition; (ii) inhibiting the pathologic condition, i.e., arresting its development; (iii) relieving the pathologic condition, i.e., causing regression of the pathologic condition; or (iv) relieving the conditions mediated by the pathologic condition.

The term "therapeutically effective amount" refers to that amount of a compound of the invention that is sufficient to effect treatment, as defined above, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "pharmaceutically acceptable salts" includes, but is not limited to, salts well known to those skilled in the art, for example, mono-salts (e.g. alkali metal and ammonium salts) and poly salts (e.g. di- or tri-salts,) of the compounds of the invention. Pharmaceutically acceptable salts of compounds of Formulas (I) and (II) are where, for example, an exchangeable group, such as hydrogen in —OH, —NH, or —P(=O)

(OH)—, is replaced with a pharmaceutically acceptable cation (e.g. a sodium, potassium, or ammonium ion) and can be conveniently be prepared from a corresponding compound of Formula (I) or Formula (II) by, for example, reaction with a suitable base. In cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts. Pharmaceutically acceptable salts may be obtained using standard procedures well known in the art, for example, by reacting a sufficiently basic compound such as an amine with a suitable acid affording a physiologically acceptable anion. Alkali metal (for example, sodium, potassium or lithium) or alkaline earth metal (for example, calcium) salts of carboxylic acids can also be made.

The term "prodrug" or "prodrugs" is used in its ordinary meaning in the art and means a compound of the invention that has its charged moieties masked or protected by another moiety that is designed to be cleaved under particular physiological conditions, leaving the deprotected or unmasked compound of the invention. The use of masking agents is common and well-known in the art and, in particular, masking phosphate or phosphonate groups. All such masking agents are suitable and can be used with the compounds of the invention. Various agents such as acyloxy alkyl esters are described by Srivasta et al., (1984 *Bioorganic Chemistry* 12, 118-12), and by Freeman et al. (1997 *Progress in Medicinal Chemistry* 34:112-147) which are each incorporated in their entirety herein by reference; and 3-phthalidyl phosphonate esters are described by Dang Q., et al., (1999 *Bioorganic & Med. Chem. Letters,* 9:1505-1510), which is incorporated in its entirety herein by reference. For example, and not by way of limitation, Srivasta et al. also describe acetoxymethyl, isobutryloxymethyl, and pivaloxymethyl as masking agents. Other suitable masking groups comprising pivaloxyalkyl, e.g., pivaloxymethyl, or a pivaloyloxy group as described by Farquhar D. et al., (1995 *J. Med. Chem.,* 38:488-495) which is incorporated in its entirety herein by reference. Still other masking or protecting agents are described in U.S. Pat. Nos. 4,816,570 and 4,968,788 both of which are incorporated in their entirety herein by reference. Lipid prodrugs are also suitable for use with the compounds of the invention. By non-limiting example, certain lipid prodrugs are described in Hostetler et al., (1997 *Biochem. Pharm.* 53:1815-1822), and Hostetler et al., 1996 *Antiviral Research* 31:59-67), both of which are incorporated in their entirety herein by reference. Additional examples of suitable prodrug technology is described in WO 90/00555; WO 96/39831; WO 03/095665A2; U.S. Pat. Nos. 5,411,947; 5,463,092; 6,312,662; 6,716,825; and U.S. Published Patent Application Nos. 2003/0229225 and 2003/0225277 each of which is incorporated in their entirety herein by reference. Such prodrugs may also possess the ability to target the drug compound to a particular tissue within the patient, e.g., liver, as described by Erion et al., (2004 *J. Am. Chem. Soc.* 126:5154-5163; Erion et al., *Am. Soc. Pharm. & Exper. Ther. DOI:*10.1124/jept.104.75903 (2004); WO 01/18013 A1; U.S. Pat. No. 6,752,981), each of which is incorporated in their entirety herein by reference. By way of non-limiting example, other prodrugs suitable for use with the compounds of the invention are described in WO 03/090690; U.S. Pat. No. 6,903,081; U.S. Patent Application No. 2005/0171060A1; U.S. Patent Application No. 2002/0004594A1; and by Harris et al., (2002 *Antiviral Chem & Chemo.* 12: 293-300; Knaggs et al., 2000 *Bioorganic & Med. Chem. Letters* 10: 2075-2078) each of which is incorporated in their entirety herein by reference. Some of the compounds described herein possess one or more chiral (also known as asymmetric) centers, and may lead to optical isomers. All such isomers, as well as diastereomers and enantiomers are included in the present invention. Racemic mixtures of compounds are also included in the present invention. Resolution of such racemic mixtures can be made using standard procedures known in the art. By way of non-limiting example, one of skill in the art can obtain the two enantiomers of the racemic amino acid by using chiral column separation or by proper functionalization followed by enzymatic resolution or by treatment of the racemate with a chiral amine to form a diastereomeric salt and the two diastereomers separated by crystallization. The parent compound can then be liberated from the amine salt by acid treatment. Alternatively, one can obtain the two enantiomers of the racemic final compound by using chiral column separation or by treatment with a chiral amine to form a diastereomeric salt and the two diastereomers separated by crystallization. The parent compound can then be liberated from the amine salt by acid treatment. Another method that can be used to resolve enantiomers of a chiral amino acid is to form a conjugate (e.g. ester) with a chiral moiety (e.g. a chiral alcohol) to produce a mixture of diasteromeric adducts. These adducts can be separated by ordinary (non-chiral) chromatography or by fractional crystallization, then the respective enantiomers of the amino acid liberated by cleavage of the conjugate.

According to one embodiment, the invention provides compounds of Formula (I) where:

$X_1$ is a linker group or is absent;

$X_2$ is H or optionally substituted straight-chained or branched aliphatic, preferably comprising 1 to 8 carbons, optionally containing 1 or more double or triple bonds, wherein one or more of the carbons are optionally replaced by R* wherein R* is optionally substituted cycloalkyl, heterocycloalkyl, aryl or heteroaryl; —C(O)—, —C(O)C(O)—, —C(O)NR$^{11}$—, —C(O)NR$^{11}$NR$^{12}$—, —C(O)O—, —OC(O)—, —NR$^{11}$CO$_2$—, —O—, —NR$^{11}$C(O)NR$^{12}$—, —OC(O)NR$^{11}$—, —NR$^{11}$NR$^{12}$—, —NR$^{11}$C(O)—, —S—, —SO—, —SO$_2$—, —NR$^{11}$—, —SO$_2$NR$^{11}$— or —NR$^{11}$SO$_2$—, wherein R$^{11}$ and R$^{12}$ are independently selected from H and optionally substituted aliphatic, cycloalkyl, heterocycloalkyl, aryl or heteroaryl; or $X_2$ is R*, i.e., $X_2$ is an optionally substituted cycloalkyl, heterocycloalkyl, aryl or heteroaryl; —C(O)—, —C(O)C(O)—, —C(O)NR$^{11}$, —C(O)NR$^{11}$NR$^{12}$—, —C(O)O—, —OC(O)—, —NR$^{11}$CO$_2$—, —O—, —NR$^{11}$C(O)NR$^{12}$—, —OC(O)NR$^{11}$, —NR$^{11}$NR$^{12}$—, —NR$^{11}$C(O)—, —S—, —SO—, —SO$_2$—, —NR$^{11}$—, —SO$_2$NR$^{11}$— or —NR$^{11}$SO$_2$—;

R$^1$ is H or optionally substituted aliphatic, cycloalkyl, heterocycloalkyl, aryl or heteroaryl;

$R_2$ is H or an optionally substituted cycloalkyl, heterocycloalkyl, aryl or heteroaryl; or $R_2$ is absent when $X_2$ is H;

$R_3$ and $R_4$ are independently H, alkyl or $C_{5-6}$ aryl;

at least one of $R_5$ and $R_6$ is halo;

$R_7$ and $R_8$ are each independently H or optionally substituted aliphatic, cycloalkyl, heterocycloalkyl, aryl or heteroaryl; or together form an optionally substituted ring comprising 3 to 7 carbon or heteroatoms;

R$^9$ is H or —CH$_3$;

R$^{10}$ is H or —CH$_3$; and each $R_m$ is independently H, halo, —OH, —NO$_2$, —CN, —CH$_3$, —CF$_3$, —CHF$_2$, —CH$_2$CH$_3$, —CH$_2$CF$_3$, —$CF_2CF_3$, —$CH_2Cl$, —$CH_2OH$, —$CH_2CH_2OH$, —$CH_2NH_2$, —$CH_2CH_2NH_2$, —$CH_2SO_2CH_3$, —$OR^{23}$, —$C(O)R^{23}$, —$C(O)OR^{23}$, —$C(O)N(R^{23})(R^{24})$, —$OC(O)R^{23}$, —$OC(O)OR^{23}$, —$OC(O)N(R^{23})(R^{24})$, —$N(R^{23})(R^{24})$, —$S(O)_2R^{23}$, —$SR^{23}$, —$S(O)_2N(R^{23})(R^{24})$, —$NR^{23}C(O)R^{24}$, —$NR^{21}C(O)OR^{24}$, —$NR^{23}SOOR^{24}$, —$NR^{23}C(O)N(R^{24})(R^{25})$—$NR^{23}SO_2R^{24}$, or —$NSO_2(R^{23})(R^{24})$; where $R^{23}$, $R^{24}$ and $R^{25}$ are each independently H, $C_{1-4}$ alkyl or 5 or 6 membered cycloalkyl, heterocycloalkyl, aryl or heteroaryl; or two adjacent $R^m$ groups together form an optionally substituted aromatic or non-aromatic ring comprising 5 to 7 carbon or heteroatoms; or $R^m$ and $R^7$ together form an optionally substituted aromatic or non-aromatic ring; where n is 0, 1, 2, 3 or 4.

It is preferred that compounds of formula (I) do not comprise dipeptide, tripeptide or oligopeptide moieties, such as where formula (I) represents compounds of the formula $R_1$-$AA_n$-$R_2$ where AA is an amino acid or derivative thereof and n is an integer greater than 1. Thus, it preferred that where $X_1$ is —NH—, $X_2$ is not, or does not comprise, —CHRC(O)— where R is an α-carbon substituent. Put in other terms, it is preferred that where $X_1$ is —NH—, $X_2$ is not, or does not comprise, —$CH_2C(O)$— or —$CH_2C(O)$— substituted at the methylene group. It is also preferred that $R_1X_1$ is not of the form $R_1$—C(O)CRNH— where R is an α-carbon substituent. It is further preferred that $R_1X_1$ is not of the form $R_1$—NHC(R)C(O)NH—, where R is an α-carbon substituent; particularly where $X_2$ is H or lower alkyl such as —$CH_3$ and $R_2$ is absent.

In one embodiment, $X_1$ is optionally substituted $C_{1-8}$ alkyl wherein one or more methylenes are optionally replaced by R* wherein R* is —C(O)—, —C(O)C(O)—, —C(O)NR$^{13}$—, —C(O)NR$^{13}$NR$^{14}$—, —$CO_2$—, —OC(O)—, —NR$^{13}CO_2$—, —O—, —NR$^{13}$C(O)NR$^{14}$—, —OC(O)NR$^{13}$—, —NR$^{13}$NR$^{14}$—, —NR$^{13}$C(O)—, —S—, —SO—, —$SO_2$—, —NR$^{13}$—, —$SO_2$NR$^{13}$— or —NR$^{13}SO_2$—; wherein $R^{13}$ and $R^{14}$ are independently selected from H and $C_{1-4}$ alkyl; or $X_1$ is —C(O)—, —C(O)C(O)—, —C(O)NR$^{13}$—, —C(O)NR$^{13}$N$^{14}$—, —$CO_2$—, —OC(O)—, —NR$^{13}CO_2$—, —O—, —NR$^{13}$C(O)NR$^{14}$—, —OC(O)NR$^{13}$—, —NR$^{13}$NR$^{14}$—, —NR$^{13}$C(O)—, —S—, —SO—, —$SO_2$—, —NR$^3$—, —$SO_2$NR$^{13}$— or —NR$^{13}SO_2$—.

In another embodiment, $X_1$ is —$(CH_2)$R*—, —C(O)—, —C(O)C(O)—, —C(O)NR$^{13}$—, —C(O)NR$^{13}$NR$^{14}$—, —C(O)O—, —OC(O)—, —NR$^{13}CO_2$—, —O—, —NR$^{13}$C(O)NR$^{14}$—, —OC(O)NR$^{13}$—, —NR$^{13}$NR$^{14}$—, —NR$^{13}$C(O)—, —S—, —SO—, —$SO_2$—, —NR$^{13}$—, —$SO_2$NR$^{13}$— or —NR$^{13}SO_2$—.

According to another embodiment, $X_1$ is —$SO_2$NR$^{13}$—, —NR$^{13}SO_2$—, —$(CH_2)$OC(O)NH—, —C(O)NH— or —OC(O)NR$^{13}$—.

In another embodiment, $X_1$ is absent and $R^1$ is $C_{1-8}$ alkyl or is H.

In one embodiment of compounds of Formula (I), $X_2$ is optionally substituted $C_{2-8}$ alkyl wherein one or more carbons are optionally replaced by R* wherein R* is —C(O)—, —C(O)C(O)—, —C(O)NR$^1$—, —C(O)NR$^{11}$NR$^{12}$—, —C(O)O—, —OC(O)—, —NR—C(O)O—, —O—, —NR$^{11}$C(O)NR$^{12}$—, —OC(O)NR$^{11}$—, —NR$^{11}$NR$^{12}$—, —NR$^{11}$C(O)—, —S—, —SO—, —$SO_2$—, —NR$^1$—, —$SO_2$NR$^{11}$— or —NR$^{11}SO_2$—.

In another, $X_2$ is —$(CH_2)_m$— where m is 2 to 8; or —$(CH_2)_m$—O— where m is 2 to 7; or —$(CH_2)_m(C\equiv C)(CH_2)_n$—, —$(CH_2)_m(C\equiv C)(CH_2)_nO$—, or —$(CH_2)_m(C\equiv C)(CH_2)_n$— where m and n are independently 0, 1, 2 or 3; or $X_2$ is —$CH_3$ and $R_2$ is absent.

In other embodiments, $R_1$ is $C_{1-8}$ alkyl, alkenyl or alkynyl optionally substituted with halo or hydroxyl; or optionally substituted 5 or 6 membered cycloalkyl, heterocycloalkyl, aryl or heteroaryl, and more specifically, $R_1$ is 5 or 6 membered cycloalkyl, heterocycloalkyl, aryl or heteroaryl optionally substituted with halogen, haloalkyl, —$R^{15}$, —$OR^{15}$, —$SR^{15}$, 1,2-methylenedioxy, 1,2-ethylenedioxy, —$NO_2$, —CN, —$NR^{15}R^{16}$, —$NR^{15}C(O)R^{16}$, —$NR^{15}C(O)NR^{16}R^{17}$, —$NR^{15}C(O)OR^6$, —$NR^{15}NR^{16}C(O)R^{17}$, —$NR^{15}NR^{16}C(O)NR^{17}R^{18}$, —$NR^{15}NR^{16}C(O)OR^{17}$, —$C(O)C(O)R^{16}$, —$C(O)CH_2C(O)R^{16}$, —$C(O)OR^{15}$, —$C(O)R^{15}$, —$C(O)NR^{15}R^{16}$, —$OC(O)NR^{15}R^{16}$, —$S(O)_2R^{15}$, —$SO_2NR^{15}R^{16}$, —$S(O)R^{15}$, —$NR^{15}SO_2$, —$NR^{16}R^{17}$, —$NR^{15}SO_2R^{16}$, —$C(=S)NR^{15}R^{16}$, —$C(=NH)N^{15}R^{16}$, —$(CH_2)_yNHC(O)R^{15}$, —$(CH_2)_yR^{15}$, —$(CH_2)_yNHC(O)NHR^{15}$, —$(CH_2)_yNHC(O)OR^{15}$, —$(CH_2)_yNHS(O)R^{15}$ or —$(CH_2)_yNHSO_2R^{15}$, wherein $R^{15}$, $R^{16}$, $R^{17}$ and $R^{18}$ are independently selected from H and optionally substituted $C_{1-6}$ alkyl; and wherein y is 0-6.

In another embodiment, $R_1$ is methyl or phenyl.

In other embodiments, $R_2$ is optionally substituted 5 or 6 membered cycloalkyl, heterocycloalkyl, aryl or heteroaryl, and more specifically, $R_2$ is 5 or 6 membered cycloalkyl, heterocycloalkyl, aryl or heteroaryl optionally substituted with halogen, haloalkyl, —$R^{19}$, —$OR^{19}$, —$SR^{19}$, 1,2-methylenedioxy, 1,2-ethylenedioxy, —$NO_2$, —CN, —$NR^{19}R^{20}$, —$NR^{19}C(O)R^{20}$, —$NR^{19}C(O)NR^{20}R^{21}$, —$NR^{19}C(O)OR^2$, —$NR^{19}NR^{20}C(O)R^{21}$, —$NR^{19}NR^{20}C(O)NR^{21}NR^{22}$, —$NR^{19}NR^{20}C(O)OR^{21}$, —$C(O)C(O)R^{19}$, —$C(O)CH_2C(O)R^{19}$, —$C(O)OR^{19}$, —$C(O)R^{19}$, —$C(O)N^{19}R^{20}$, —$OC(O)NR^{19}R^{20}$, —$S(O)_2R^{19}$, —$SO_2NR^{19}R^{20}$, —$S(O)R^{19}$—$NR^{19}SO_2NR^{20}R^{21}$, —$NR^{19}SO_2R^{20}$, —$C(=S)NR^{19}R^{20}$, —$C(=NH)NR^{19}R^{20}$, —$(CH_2)_yNHC(O)R^{19}$, —$(CH_2)_yR^{19}$, —$(CH_2)_yNHC(O)NHR^{19}$, —$(CH_2)_yNHC(O)OR^{19}$, —$(CH_2)_yNHS(O)R^{19}$ or —$(CH_2)_yNHSO_2R^{19}$, wherein $R^{19}$, $R^{20}$, $R^{21}$ and $R^{22}$ are independently selected from H, $C_{1-6}$ aliphatic or 5 or 6 membered aryl, heteroaryl, cycloalkyl or heterocycloalkyl, and wherein y is 0-6.

$R_2$ can also be phenyl optionally substituted with —OH or —$C(O)OR^{19}$. In a specific embodiment, $R_2$ is phenyl substituted with one or more groups selected from —OH and —$C(O)OCH_3$. $X_2R_2$ (i.e., where $R_2$ is absent) can also be lower alkyl, such as, for example, methyl, ethyl or propyl.

In yet another embodiment of compounds of formula (I), $X_1$ is —$SO_2$NR$^{13}$—, —$(CH_2)OC(O)NH$—, —C(O)NH— or —OC(O)NR$^{13}$—; and $X_2$ is —$(CH_2)_m$— where m is 2 to 8 or —$(CH_2)_m$—O— where m is 2 to 7. In another, $X_1$ is —$SO_2$NH— or —$(CH_2)OC(O)NH$—; and $X_2$ is —$(CH_2)_4$O— or —C(O)NH—; where, for example, $R_1$ is methyl or phenyl; and $R_2$ is phenyl optionally substituted with one or more groups selected from —OH and —$C(O)OCH_3$. In a further embodiment, $R_3$ and $R_4$ are independently H, $C_{1-4}$ alkyl such as methyl, ethyl, propyl or butyl, or phenyl. In another embodiment, $R_3$ and $R_4$ are each H. In another, both $R_5$ and $R_6$ are halo, preferably F; and $R_m$ is halo where m is 0, 1 or 2.

Specific embodiments of Formula I include the following compounds as well as those set forth in the Examples 1-24:

(2S)-{4-[2-Benzyloxycarbonylamino-2-(3-hydroxy-propylcarbamoyl)-ethyl]-phenyl}difluoromethylphosphonic acid;

(2S)-{4-[2-Benzyloxycarbonylamino-2-(dimethylcarbamoyl)-ethyl]-phenyl}difluoromethylphosphonic acid;

(2S)-{4-[2-(4-chlorophenyl)sulfonylamino-2-(4-phenylbutylcarbamoyl)-ethyl]-phenyl}difluoromethylphosphonic acid;

(2S)-{4-[2-Benzyloxycarbonylamino-2-(3-morpholin-4-yl-propylcarbamoyl)-ethyl]-phenyl}difluoromethylphosphonic acid;
(2S)-{4-[2-(2-Pyridyl)sulfonylamino-2-(4-phenylbutylcarbamoyl)-ethyl]-phenyl}difluoromethylphosphonic acid;
(2S)-{4-[2-(3-Pyridyl)sulfonylamino-2-(4-phenylbutylcarbamoyl)-ethyl]-phenyl}difluoromethylphosphonic acid;
(2S)-{4-[2-Benzyloxycarbonylamino-2-(3-dimethylaminopropylcarbamoyl)-ethyl]-phenyl}difluoromethylphosphonic acid;
(2S)-{4-[2-Phenylsulfonylamino-2-(3-imidazol-1-yl-propylcarbamoyl)-ethyl]-phenyl}difluoromethylphosphonic acid;
(2S)-{4-[2-Phenylsulfonylamino-2-(3-(4-chlorophenoxy)propylcarbamoyl)-ethyl]-phenyl}difluoromethylphosphonic acid;
(2S)-{4-[2-Phenylsulfonylamino-2-(4-(phenylamino)phenylcarbamoyl)-ethyl]-phenyl}difluoromethylphosphonic acid;
(2S)-{4-[2-Phenylsulfonylamino-2-(3-(3-chlorophenoxy)propylcarbamoyl)-ethyl]-phenyl}difluoromethylphosphonic acid;
(2S)-{4-[2-Phenylsulfonylamino-2-(3-(3-dimethylaminophenoxy)propylcarbamoyl)-ethyl]-phenyl}difluoromethylphosphonic acid;
(2S)-{4-[2-Dimethylaminosulfonylamino-2-(4-phenylbutylcarbamoyl)-ethyl]-phenyl}difluoromethylphosphonic acid;
(2S)-{4-[2-Methylsulfonylamino-2-(4-phenylbutylcarbamoyl)-ethyl]-phenyl}difluoromethylphosphonic acid;
(2S)-{4-[2-Phenylsulfonylamino-2-(3-phenoxypropylcarbamoyl)-ethyl]-phenyl}difluoromethylphosphonic acid;
(2S)-{4-[2-(N-dodecylsulfonylamino)-2-(4-phenylbutylcarbamoyl)-ethyl]-phenyl}difluoromethylphosphonic acid;
(2S)-{4-[2-(4-Methoxyphenyl)sulfonylamino-2-(4-phenylbutylcarbamoyl)-ethyl]-phenyl}difluoromethylphosphonic acid;
(2S)-{4-[2-(2-Aminoethanesulfonylamino)-2-(4-phenylbutylcarbamoyl)-ethyl]-phenyl}difluoromethylphosphonic acid;
(2S)-{4-[2-Phenylsulfonylamino-2-(3-phenoxy-phenylcarbamoyl)-ethyl]-phenyl}difluoromethylphosphonic acid;
(2S)-{4-[2-Phenylsulfonylamino-2-(3-benzyl-phenylcarbamoyl)-ethyl]-phenyl}difluoromethylphosphonic acid;
(2S)-{4-[2-Phenylsulfonylamino-2-(3-(N-methyl,N-phenylamino)-propylcarbamoyl)-ethyl]-phenyl}difluoromethylphosphonic acid;
(2S)-{4-[2-(4-Methylphenylsulfonylamino)-2-(4-phenylbutylcarbamoyl)-ethyl]-phenyl}difluoromethylphosphonic acid;
(2S)-{4-[2-Isopropylsulfonylamino-2-(4-phenylbutylcarbamoyl)-ethyl]-phenyl}difluoromethylphosphonic acid;
(2S)-{4-[2-(6-Phenoxy-pyrid-3-yl)sulfonylamino-2-(4-phenylbutylcarbamoyl)-ethyl]-phenyl}difluoromethylphosphonic acid;
(2S)-{4-[2-Phenylsulfonylamino-2-(4-(3-chlorophenoxy)-phenylcarbamoyl)-ethyl]-phenyl}difluoromethylphosphonic acid;
(2S)-{4-[2-Phenylsulfonylamino-2-(3-phenylamino-phenylcarbamoyl)-ethyl]-phenyl}difluoromethylphosphonic acid;
(2S)-{4-[2-Phenylsulfonylamino-2-(3-(4-trifluoromethoxyphenoxy)propylcarbamoyl)-ethyl]-phenyl}difluoromethylphosphonic acid;
(2S)-{4-[2-(3,4-dichlorophenyl)sulfonylamino-2-(4-phenylbutylcarbamoyl)-ethyl]-phenyl}difluoromethylphosphonic acid;
(2S)-{4-[2-(6-Morpholin-4-yl-pyrid-3-yl)sulfonylamino-2-(4-phenylbutylcarbamoyl)-ethyl]-phenyl}difluoromethylphosphonic acid;
(2S)-{4-[2-(2-Benzothiophene)sulfonylamino-2-(4-phenylbutylcarbamoyl)-ethyl]-phenyl}difluoromethylphosphonic acid;
(2S)-{4-[2-(2-Thienyl)sulfonylamino-2-(4-phenylbutylcarbamoyl)-ethyl]-phenyl}difluoromethylphosphonic acid;
(2S)-{4-[2-(1-Naphthyl)sulfonylamino-2-(4-phenylbutylcarbamoyl)-ethyl]-phenyl}difluoromethylphosphonic acid;
(2S)-{4-[2-Phenylsulfonylamino-2-(4-phenyl-but-3E-enylcarbamoyl)-ethyl]-phenyl}difluoromethylphosphonic acid;
(2S)-{4-[2-Phenylsulfonylamino-2-(2-(4-chlorophenylcarbamoyl)ethyl-carbamoyl)-ethyl]-phenyl}difluoromethylphosphonic acid;
(2S)-{4-[2-Phenylsulfonylamino-2-(3-(4-bromo-phenoxy)propylcarbamoyl)-ethyl]-phenyl}difluoromethylphosphonic acid;
(2S)-{4-[2-Phenylsulfonylamino-2-(3-(3,5-dimethoxy-4-acetyl-phenoxy)propyl-carbamoyl)-ethyl]-phenyl}difluoromethylphosphonic acid;
(2S)-{4-[2-Phenylsulfonylamino-2-(3-(3,4-dichloro-phenoxy)propylcarbamoyl)-ethyl]-phenyl}difluoromethylphosphonic acid;
(2S)-{4-[2-Phenylsulfonylamino-2-(3-(2-nitrophenylsulfonylamino)propyl-carbamoyl)-ethyl]-phenyl}difluoromethylphosphonic acid;
(2S)-{4-[2-Benzylsulfonylamino-2-(4-phenylbutylcarbamoyl)-ethyl]-phenyl}-difluoromethylphosphonic acid;
(2S)-{4-[2-(2-Phenylethyl)sulfonylamino-2-(4-phenylbutylcarbamoyl)-ethyl]-phenyl}difluoromethylphosphonic acid;
(2S)-{4-[2-(3,5-Dimethylisoxazol-4-yl)sulfonylamino-2-(4-phenylbutyl-carbamoyl)-ethyl]-phenyl}difluoromethylphosphonic acid;
(2S)-{4-[2-(Trifluoromethyl)sulfonylamino-2-(4-phenylbutylcarbamoyl)-ethyl]-phenyl}difluoromethylphosphonic acid;
(2S)-(2-Bromo-4-{2-(3-pyridyl)sulfonylamino-2-[4-(2-methoxycarbonyl-3-hydroxy-phenoxy)butylcarbamoyl]-ethyl}-phenyl)difluoromethylphosphonic acid;
(2S)-[(4-{2-Phenylsulfonylamino-2-[3-(2-oxo-pyrrolidin-1-yl)-propylcarbamoyl]-ethyl}-phenyl)]difluoromethylphosphonic acid;
(2S)-{4-[2-Phenylsulfonylamino-2-(4-(4-methoxyphenylamino)phenyl-carbamoyl)-ethyl]-phenyl}difluoromethylphosphonic acid;
(2S)-[4-(2-Phenylsulfonylamino-3-[1,4']bipiperidinyl-1'-yl-3-oxo-propyl)-phenyl]difluoromethylphosphonic acid;
(2S)-{4-[2-Phenylsulfonylamino-2-(3-(4-trifluoromethyl-phenoxy)propyl-carbamoyl)-ethyl]-phenyl}difluoromethylphosphonic acid; and
(2S)-{4-[2-Phenylsulfonylamino-2-(3-(4-quinolineoxy)propylcarbamoyl)-ethyl]-phenyl}difluoromethylphosphonic acid.

According to one embodiment, the invention provides compounds of Formula (IIa) where at least one of, and preferably both, $R_a$ and $R_b$ are halogen;
$R^{31}$ and $R^{32}$ are each hydrogen;
ring A is phenyl, pyridine or thiophene;
$R^{28}$ is preferably —$[CH_2]_n$—$[C(H)_{3-p}]_x(R^{33})_p$, —$C(O)NH(CH_2)_nR^{33}$, —$(CH_2)_n$—$CHR^{34}R^{35}$ or $CHNR^{34}$; or $R^{28}$ taken together with either $R^{27}$ or $R^{29}$ form an optionally substituted ring comprising 3 to 7 carbon or heteroatoms, and more preferably 5 to 8 carbon or heteroatoms;

each $R^{33}$ is independently H, halogen, —C(O)OR$^{39}$, —OH, —CN, —N=N—N, —N(R$^{37}$)(R$^{38}$), —CH(R$^{39}$)(NH$_2$)C(O)OR$^{39}$, —CH$_2$R$^{35}$ or —CHR$^{35}$—(NHS(O)$_2$—R$^{39}$); or optionally substituted cycloalkyl, aryl, heterocyloalkyl, or heteroaryl;

$R^{34}$ is H or —N(R$^{37}$)(R$^{38}$);

$R^{35}$ is H or —C(O)R$^{34}$;

$R^{37}$ and $R^{38}$ are each independently H, $C_{1-6}$ alkyl, —S(O)$_2$R$^{39}$, —C(O)(CH$_2$)$_q$R$^{39}$, —S(O)$_2$NHR$^{39}$ or —NHC(O)NHR$^{39}$; and $R^{39}$ is H, optionally substituted $C_{1-6}$ alkyl, $C_{3-8}$ aryl or 3 to 8 membered heteroaryl.

Compounds of formula IIa wherein $R^{28}$ together with $R^{29}$ (or alternatively, with $R^{27}$) form an optionally substituted 5 membered ring may be exemplified by formula IIa1:

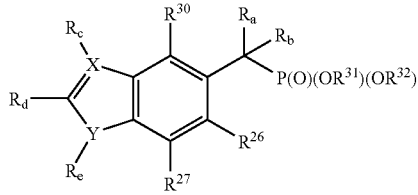

(IIa1)

wherein X and Y are independently C, N, S and O;

$R_c$, $R_d$ and $R_e$ are independently absent or selected from H, halogen, haloalkyl, —R$^{45}$, —OR$^{45}$, —SR$^{45}$, 1,2-methylenedioxy, 1,2-ethylenedioxy, —NO$_2$, —CN, —NR$^{45}$R$^{46}$, —NR$^{45}$C(O)R$^6$, —NR$^{45}$C(O)NR$^{46}$R$^{47}$, —NR$^{45}$C(O)OR$^{46}$, —NR$^{45}$NR$^{46}$C(O)R$^{47}$, —NR$^{45}$NR$^{46}$C(O)NR$^{47}$R$^{48}$, —NR$^{45}$NR$^{46}$C(O)OR$^{47}$, —C(O)C(O)R$^{16}$, —C(O)CH$_2$C(O)R$^{46}$, C(O)OR$^{45}$, —C(O)R$^{45}$, C(O)NR$^{45}$R$^{46}$, —OC(O)NR$^{45}$R$^{46}$, —S(O)$_2$R$^{45}$, —SO$_2$NR$^{45}$R$^{46}$, —S(O)R$^{45}$, —NR$^{45}$SO$_2$NR$^{46}$R$^{47}$, —NR$^{45}$SO$_2$R$^{46}$, —C(=S)NR$^{45}$R$^{46}$, —C(=NH)NR$^{45}$R$^{46}$, —(CH$_2$)$_y$NHC(O)R$^{45}$, —(CH$_2$)$_y$R$^{45}$, —(CH$_2$)$_y$NHC(O)NHR$^{45}$, —(CH$_2$)$_y$NHC(O)OR$^{45}$, —(CH$_2$)$_y$NHC(O)(CH$_2$)R$^{45}$NHC(O)R$^{46}$, —(CH$_2$)$_y$NHS(O)R$^{45}$ or —(CH$_2$)$_y$NHSO$_2$R$^{45}$, wherein R$^{45}$ and R$^{46}$ are independently selected from H and optionally substituted $C_{1-6}$ alkyl; and wherein y is 0-6.

According to several embodiments, X and Y are independently S or N, and $R_c$, $R_d$ and $R_e$ are independently absent or selected from —NR$^{45}$C(O)R$^{46}$, —(CH$_2$)$_y$NHC(O)R$^{45}$ and —(CH$_2$)$_y$NHC(O)(CH)(R$^{45}$)NHC(O)R$^{46}$. In further embodiments, X and Y are independently S or N; $R_c$, $R_d$ and $R_e$ are independently absent or selected from —NHC(O)CH$_3$, —(CH$_2$)NHC(O)CH$_3$ and —(CH$_2$)NHC(O)(CH$_2$)NHC(O)CH$_3$. Other embodiments include compounds where X and Y are O; X is N and Y is S; X is S and Y is N; X is N and Y is C; and X is C and Y is N. Preferred embodiments include compounds where one of R$^{26}$ and R$^{30}$ is halo, preferably Br; one or both of R$_a$ and R$_b$ are halo, preferably F; and one or both of R$^{31}$ and R$^{32}$ are H.

According to another embodiment of the invention, compounds of Formula (IIb) are provided where $R_a$ and $R_b$ are both F; $R^{31}$ and $R^{32}$ are each hydrogen; ring A is phenyl, pyridine or thiophene; $R^{30}$ is Br;

$R^{28}$ is —(CH$_2$)$_n$—CHR$^{34}$R$^{35}$ or —CHNR$^{34}$; or R$^{28}$ taken together with either R$^{27}$ or R$^{29}$ form an optionally substituted ring comprising 3 to 8 carbon or heteroatoms;

$R^{34}$ is H or —NR$^{37}$R$^{38}$;

$R^{35}$ is H or —C(O)R$^{34}$;

$R^{37}$ and $R^{38}$ preferably are each independently H, $C_{1-6}$ alkyl, —S(O)$_2$R$^{39}$, —C(O)(CH$_2$)$_q$R$^{39}$, —S(O)$_2$NHR$^{39}$ or —NHC(O)NHR$^{39}$; and $R^{39}$ is H or an optionally substituted $C_{1-6}$ alkyl, 3 to 8 membered aryl or heteroaryl.

According to yet another embodiment of the invention, compounds of Formula (IIc) are provided where $R^{31}$ and $R^{32}$ are each hydrogen; ring A is phenyl, pyridine or thiophene; $R^{26}$, $R^{27}$ and $R^{29}$ are each H;

$R^{40}$ is H, alkyl or —C(O)NR$^{37}$R$^{38}$;

$R^{41}$ is —NR$^{37}$R$^{38}$;

$R^{37}$ and $R^{38}$ are each independently H, $C_{1-6}$ alkyl, —S(O)$_2$R$^{39}$, C(O)(CH$_2$)$_q$R$^{39}$, —S(O)$_2$NHR$^{39}$ or —NHC(O)NHR$^{39}$; and $R^{39}$ is H or an optionally substituted $C_{1-6}$ alkyl, 3 to 8 membered aryl or heteroaryl.

According to yet another embodiment of the invention, compounds of Formula (IId) are provided where $R^{31}$ and $R^{32}$ are each hydrogen; ring A is phenyl; $R^{26}$, $R^{27}$ and $R^{29}$ are each H;

$R^{40}$ is alkyl or —C(O)NR$^{37}$R$^{38}$;

$R^{42}$ is —S(O)$_2$R$^{39}$, —C(O)(CH$_2$)$_q$R$^{39}$, —S(O)$_2$NHR$^{39}$ or —NHC(O)NHR$^{39}$;

$R^{37}$ and $R^{38}$ are each independently H, $C_{1-3}$ alkyl, —S(O)$_2$R$^{39}$, C(O)(CH$_2$)$_q$R$^{39}$, —S(O)$_2$NHR$^{39}$ or —NHC(O)NHR$^{39}$; and $R^{39}$ is H or an optionally substituted $C_{1-3}$ alkyl, 3 to 8 membered aryl or heteroaryl.

According to a still further embodiment of the invention, compounds of Formula (IIe) are provided where $R^{31}$ and $R^{32}$ are each hydrogen; ring A is phenyl; $R^{26}$, $R^{27}$ and $R^{29}$ are each H;

$R^{40}$ is alkyl or —C(O)NR$^{37}$R$^{38}$;

$R^{43}$ is H or R$^{39}$;

$R^{37}$ and $R^{38}$ are each independently H, $C_{1-3}$ alkyl, —S(O)$_2$R$^{39}$, C(O)(CH$_2$)$_q$R$^{39}$, —S(O)$_2$NHR$^{39}$ or —NHC(O)NHR$^{39}$; and $R^{39}$ is H or an optionally substituted $C_{1-3}$ alkyl, 3-8 membered aryl or 3-8 membered heteroaryl.

Specific embodiments of Formula (II) include the following compounds as well as those set forth in the Examples 25-105:

{[4-(2-Acetylamino-2-carbamoyl-ethyl)-phenyl]-difluoromethyl}-phosphonic acid;

[4-(Phosphono-difluoro-methyl)-phenyl]-acetic acid benzyl ester;

[4-(Phosphono-difluoro-methyl)-phenyl]-acetic acid;

4-{2-[4-(2-methoxycarbonyl-3-hydroxy-phenoxy)butylcarbamoyl]-ethyl}-phenyldifluoromethylphosphonic acid;

4-methyl-2-nitro-phenyldifluoromethylphosphonic acid;

2-Amino-3-[3-bromo-4-(difluoro-phosphono-methyl)-phenyl]-propionic acid;

[(2-Bromo-4-ethylaminomethyl-phenyl)-difluoro-methyl]-phosphonic acid;

{[2-Bromo-4-(4-phenyl-butylcarbamoyl)-phenyl]-difluoromethyl}-phosphonic acid;

[(2-Bromo-3-methyl-phenyl)-difluoro-methyl]-phosphonic acid;

{[4-(2-Acetylamino-ethyl)-phenyl]-difluoro-methyl}-phosphonic acid;

[(4-Azidomethyl-2-bromo-phenyl)-difluoro-methyl]-phosphonic acid;

{[2-Bromo-4-(2-benzoyloxy-amino-ethyl)-phenyl]-difluoro-methyl}-phosphonic acid; and

[(2-Bromo-4-fluoro-phenyl)-difluoro-methyl]-phosphonic acid.

Non-limiting examples of compounds of Formula IIa wherein $R^{28}$ when taken together with either $R^{27}$ or $R^{29}$ form an optionally substituted $C_{3-8}$ cycloalkyl, aryl, heterocycloalkyl or heteroaryl are shown in the Table 1 below.

TABLE 1

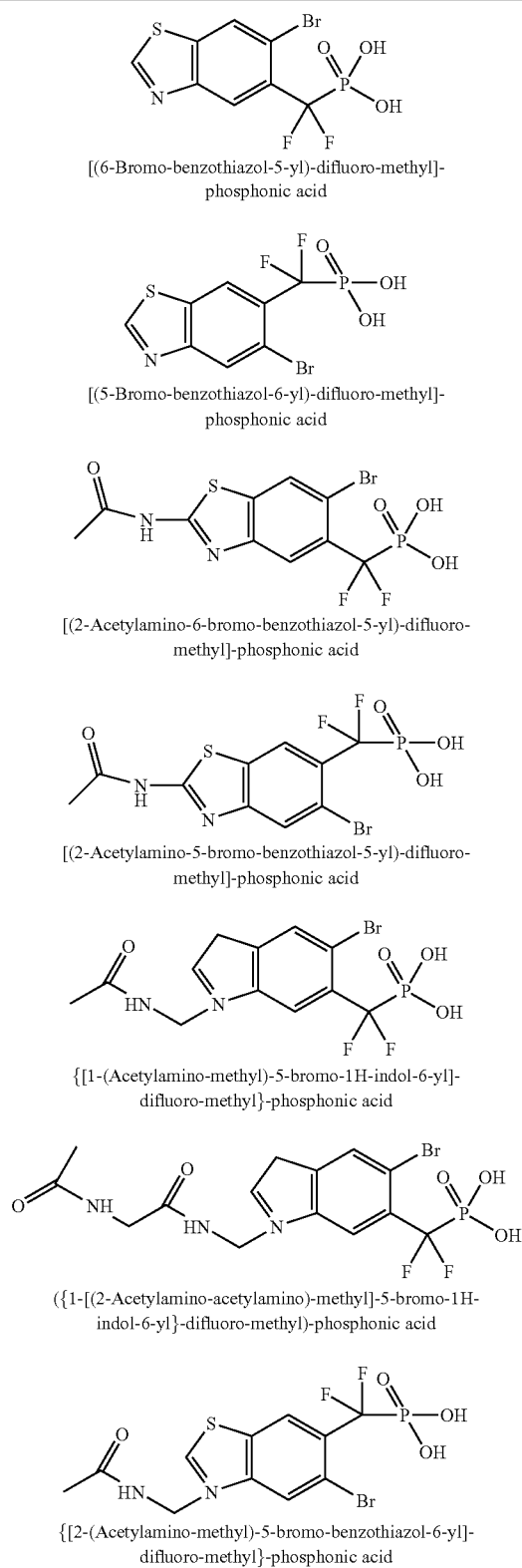

[(6-Bromo-benzothiazol-5-yl)-difluoro-methyl]-phosphonic acid

[(5-Bromo-benzothiazol-6-yl)-difluoro-methyl]-phosphonic acid

[(2-Acetylamino-6-bromo-benzothiazol-5-yl)-difluoro-methyl]-phosphonic acid

[(2-Acetylamino-5-bromo-benzothiazol-5-yl)-difluoro-methyl]-phosphonic acid

{[1-(Acetylamino-methyl)-5-bromo-1H-indol-6-yl]-difluoro-methyl}-phosphonic acid ({1-[(2-Acetylamino-acetylamino)-methyl]-5-bromo-1H-indol-6-yl}-difluoro-methyl)-phosphonic acid {[2-(Acetylamino-methyl)-5-bromo-benzothiazol-6-yl]-difluoro-methyl}-phosphonic acid TABLE 1-continued

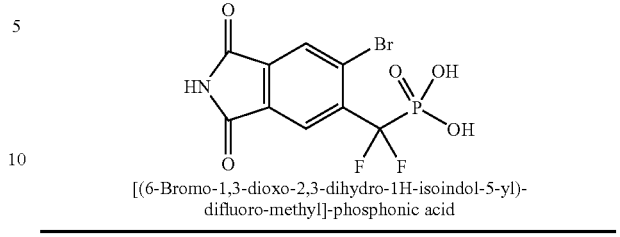

[(6-Bromo-1,3-dioxo-2,3-dihydro-1H-isoindol-5-yl)-difluoro-methyl]-phosphonic acid The compounds of the present invention, by inhibiting PTP 1B, improve insulin-sensitivity and thus have utility in preventing or treating Type 1 and Type 2 diabetes, improving glucose tolerance and insulin-sensitivity when there is insulin-resistance, and in treating or preventing obesity, all in mammals that are in need of such treatments or that might benefit from such treatments.

The compounds of the present invention may also be useful in the treatment, prevention or control of a number of conditions that accompany type 2 diabetes, including hyperlipidemia, hypertriglyceridemia, hypercholesterolemia (including beneficially raising low HDL levels), atherosclerosis, vascular restenosis, pancreatitis, adipose cell tumors, adipose cell carcinomas such as liposarcoma, dyslipidemia, inflammatory bowel disease, inflammation in general, and other disorders where insulin resistance is a component. Finally, the compounds may be used to treat or prevent cancer, such as prostate cancer, neurodegenerative diseases and the like.

Dosage levels on the order of from about 0.01 mg to about 100 mg/kg of body weight per day are useful in the treatment of the above-indicated conditions, or alternatively about 0.5 mg to about 7 g per patient per day. For example, the diseases and conditions described herein may be effectively treated by the administration of from about 0.01 to 50 mg of the compound per kilogram of body weight per day, or alternatively about 0.5 mg to about 3.5 g per patient per day.

A compound of the invention is typically combined with the carrier to produce a dosage form suitable for the particular patient being treated and the particular mode of administration. For example, a formulation intended for the oral administration to humans may contain from about 0.5 mg to about 5 g of the compound of the invention, compounded with an appropriate and convenient amount of carrier material which may vary from about 5 to about 95 percent of the total composition. Representative dosage forms will generally contain between from about 1 mg to about 500 mg of a compound of the invention, typically 25 mg, 50 mg, 100 mg, 200 mg, 300 mg, 400 mg, 500 mg, 600 mg, 800 mg, or 1000 mg.

It is understood that the specific dose level for any particular patient will depend upon a variety of factors including the age, body weight, general health, sex, diet, time of administration, route of administration, rate of excretion, drug combination and the severity of the particular disease undergoing therapy.

The compounds of the present invention may be used in combination with one or more other pharmaceutically-active compounds, such as anti-diabetic compounds (by way of non-limiting example, insulin, sulfonyl ureas, PPAR-alpha and/or -gamma ligands, including ligands that have both PPAR-alpha and -gamma activity) or anti-obesity compounds, and compounds that improve the lipid profile of the patient. The compounds may be combined with a cholesterol biosynthesis inhibitor, particularly an HMG-CoA reductase inhibitor, such as lovastatin, simvastatin, pravastatin, fluvastatin, atorvastatin and rivastatin, in an amount effective to improve the lipid profile. In combination with a PTP-1B inhibitor, this may be beneficial in treating or preventing atherosclerosis and other conditions that often are associated with Type 2 diabetes.

Examples of other pharmaceutically active compounds that may be combined with a compound of Formula (I) or Formula (II) and administered in concurrent or sequential combination therewith may include, by way of non-limiting example, other anti-diabetic agents such as DPP IV initors, GLP 1 analogs, insulin sensitizers such as PPARγ agonists such as the glitazones (e.g. troglitazone, pioglitazone, englitazone, MCC-555, rosiglitazone, and the like), and compounds disclosed in WO97/27857, 97/28115, 97/28137 and 97/27847; biguanides such as metformin and phenformin; insulin or insulin mimetics; sulfonylureas such as tolbutamide and glipizide, or related materials; α-glucosidase inhibitors (such as acarbose); cholesterol lowering agents such as HMG-CoA reductase inhibitors (lovastatin, simvastatin and pravastatin, fluvastatin, atorvastatin, rivastatin and other statins), sequestrants (cholestyramine, colestipol and a dialkylaminoalkyl derivatives of a cross-linked dextran), nicotinyl alcohol, nicotinic acid or a salt thereof, PPARα agonists such as fenofibric acid derivatives (gemfibrozil, clofibrate, fenofibrate and benzafibrate), inhibitors of cholesterol absorption such as for example β-sitosterol and acyl CoA: cholesterol acyltransferase inhibitors such as for example melinamide, and probucol; PPARγ agonists; antiobesity compounds such as appetite suppressants, fenfluramine, dexfenfluramine, phentiramine, sulbitramine, orlistat, neuropeptide Y5 inhibitors (NPY5 receptor antagonosts), leptin, β₃ adrenergic receptor agonists; ileal bile acid transporter inhibitors; and insulin receptor activators, such as those disclosed in copending, commonly assigned U.S. application Ser. Nos. 09/095,244 and 09/280,602.

Where a second pharmaceutical is used in addition to a compound of the invention described herein, the two pharmaceuticals may be administered together in a single composition, separately at approximately the same time, or on separate dosing schedules. The important feature is that their dosing schedules comprise a treatment plan in which the dosing schedules overlap in time and thus are being followed concurrently.

Any suitable route of administration may be employed for providing the patient with an effective dosage (e.g., oral, sublingual, rectal, intravenous, epidural, intrethecal, subcutaneous, transcutaneous, intramuscular, intraperitoneal, intracutaneous, inhalation, transdermal, nasal spray or drop, and the like). While it is possible that, for use in therapy, compounds of the present invention may be administered as the pure chemicals without carriers, excipients and the like, as by inhalation of a fine powder via an insufflator, it is preferable to present the active ingredient as a pharmaceutical formulation. The invention thus further provides a pharmaceutical formulation comprising a compound of the present invention, together with one or more pharmaceutically acceptable carriers therefor and, optionally, other therapeutic and/or prophylactic ingredients. The carrier(s) must be 'acceptable' in the sense of being compatible with the other ingredients of the formulation and not deleterious to the recipient thereof, such as a human patient or domestic animal.

Pharmaceutical formulations include those suitable for oral or parenteral (including intramuscular, subcutaneous and intravenous) administration. Forms suitable for parenteral administration also include forms suitable for administration by inhalation or insufflation or for nasal, or topical (including buccal, rectal, vaginal and sublingual) administration. The formulations may, where appropriate, be conveniently presented in discrete unit dosage forms and may be prepared by any of the methods well known in the art of pharmacy. Such methods include the step of bringing into association a compound of the invention with liquid carriers, solid matrices, semi-solid carriers, finely divided solid carriers or combinations thereof, and then, if necessary, shaping the product into the desired delivery system.

Pharmaceutical formulations suitable for oral administration may be presented as discrete unit dosage forms such as hard or soft gelatin capsules, cachets or tablets each containing a predetermined amount of the active ingredient; as a powder or asganules; as a solution, a suspension or as an emulsion; or in a chewable base such as a synthetic resin or chicle for ingestion of the agent from a chewing gum. A compound of Formula I or Formula II may also be presented as a bolus, electuary or paste. Tablets and capsules for oral administration may contain conventional excipients such as binding agents, fillers, lubricants, disintegrants, or wetting agents. The tablets may be coated according to methods well known in the art, i.e., with enteric coatings.

Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds according to the invention may also be formulated for parenteral administration (e.g., by injection, for example, bolus injection or continuous infusion) and may be presented in unit dose form in ampules, pre-filled syringes, small volume infusion containers or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, a compound of the invention as shown in Formula I or Formula II may be in powder form, obtained by aseptic isolation of sterile solid or by lyophilization from solution, for constitution with a suitable vehicle, e.g., sterile, pyrogen-free water, before use.

For topical administration to the epidermis, the compounds may be formulated as ointments, creams or lotions, or as the active ingredient of a transdermal patch. Suitable transdermal delivery systems are disclosed, for example, in A. Fisher et al. (U.S. Pat. No. 4,788,603), or R. Bawa et al. (U.S. Pat. Nos. 4,931,279; 4,668,506 and 4,713,224). Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include unit dosage forms such as lozenges comprising active ingredient in a flavored base, usually sucrose and acacia or tragacanth; pastilles comprising the active ingredient in an inert base such as gelatin and glycerin or sucrose and acacia; mucoadherent gels, and mouthwashes comprising a compound of the invention in a suitable liquid carrier.

When desired, the above-described formulations can be adapted to give sustained release of the active ingredient employed, e.g., by combination with certain hydrophilic polymer matrices, e.g., comprising natural gels, synthetic polymer gels or mixtures thereof. The polymer matrix can be coated onto, or used to form, a medical prosthesis, such as a stent, valve, shunt, gaft, or the like.

Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of a compound of the invention with the softened or melted carrier(s) followed by chilling and shaping in molds.

Formulations suitable for vaginal administration may be presented as pessaries, tampons, creams, gels, pastes, foams or sprays containing, in addition to a compound of the invention, such carriers as are known in the art to be appropriate.

For administration by inhalation, the compounds according to the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the compounds according to the invention may take the form of a dry powder composition, for example, a powder mix of the compound and a suitable powder base such as lactose or starch. The powder composition may be presented in unit dosage form in, for example, capsules or cartridges or, e.g., gelatin or blister packs from which the powder may be administered with the aid of an inhalator or insufflator.

For intra-nasal administration, the compounds of the invention may be administered via a liquid spray, such as via a plastic bottle atomizer. Typical of these are the Mistometer® (Wintrop) and the Medihaler® (Riker).

For topical administration to the eye, the compounds can be administered as drops, gels (U.S. Pat. No. 4,255,415), gums (see U.S. Pat. No. 4,136,177) or via a prolonged-release ocular insert.

The invention will now be described in greater detail by reference to the following non-limiting examples.

EXAMPLES

All starting materials described in the Examples below are commercially available or readily synthesized by those skilled in the art.

Example 1

Synthesis of Compound 1

(2S)-{4-[2-(5-Dimethylamino-1 naphthyl)sulfonylamino-2-(4-phenylbutylcarbamoyl)-ethyl]-phenyl}difluoromethylphosphonic acid

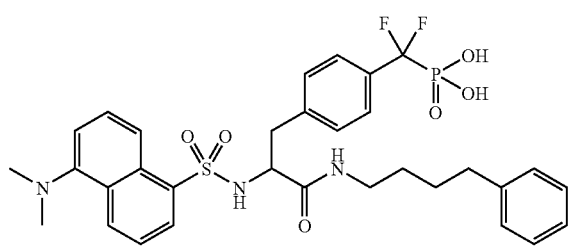

1

To a suspension of Cd metal (15.2 g, 0.135 mole) in DMF (125 mL, dried over 4 Å molecular sieves for 24 hours) was added diethyl bromodifluoromethylphosphonate (21.7 mL, 0.122 mole) and glacial acetic acid (1.6 mL). Within 4 minutes an exotherm started and lasted for 20 minutes. The suspension was stirred for 3 hours and allowed to stand at room temperature for 30-40 minutes. A 100 mL aliquot of this solution was then added to methyl N-Boc 4-iodophenylalanine (11.0 g, 0.027 mole) followed by the addition of copper (I) chloride (10.7 g, 0.108 mole) and the reaction was stirred vigorously for 18 hours. The remaining cadmium reagent solution was then added to the reaction mixture and the reaction was stirred for additional 48 hours. Ether ($Et_2O$, 1000 mL) was added and the reaction mixture was filtered through Celite®. The Celite® was washed with additional volume of ether (300 mL) and the combined ether layer was washed with saturated aqueous ammonium chloride ($NH_4Cl$, 300 mL), saturated aqueous sodium bicarbonate ($NaHCO_3$, 300 mL), water (500 mL) then dried over magnesium sulfate ($MgSO_4$). Filtration and solvent evaporation provided 19 g of crude product. Flash chromatography on silica gel using 30-45% ethyl acetate/hexanes followed by drying of the product under high vacuum with occasional warming with a heat gun afforded 5.8 g of >95% pure (2S)-{4-[2-tert-butoxycarbonylamino-2-(methoxycarbonyl)-ethyl]-phenyl}difluoromethyl-phosphonic acid diethyl ester. To this material, (1.0 g, 0.0021 mole) in THF (25 mL) at 0° C., was added 0.2N LiOH (21.0 mL, 0.0042 mole) and the reaction was stirred at 0° C. for 45 minutes. The reaction mixture was poured into a separatory funnel that contained 0.2N HCl/EtOAc (300 mL each). The EtOAc layer was separated and the aqueous layer was washed with EtOAc (100 mL). The combined EtOAc layer was dried over $MgSO_4$, filtered and the solvent evaporated to leave 0.94 g of product upon drying under high vacuum. To this material, (0.94 g, 0.0021 mole) in DMF (15 mL) at room temperature, were added hydroxybenzotriazole (HOBt, 0.35 g, 0.0023 mole), phenbutylamine (0.36 mL, 0.0023 mole), EDC (0.44 g, 0.0023 mole) and DIEA (1.0 mL, 0.0059 mole) and the solution was stirred at room temperature for 20 hours EtOAc (150 mL) and 1N HCl (70 mL) were added and the EtOAc layer was washed with saturated $NaHCO_3$ (70 mL), $H_2O$ (70 mL), brine (70 mL), dried over $MgSO_4$, filtered and evaporated. Flash chromatography on silica gel using 25% ethyl acetate/hexanes afforded substantially purified (2S)-{4-[2-tert-butoxycarbonylamino-2-(4-phenylbutyl-carbamoyl)-ethyl]-phenyl}difluoromethylphosphonic acid diethyl ester (1.16 g).

To the diethyl ester obtained, (0.55 g, 0.00094 mole) in $CH_2Cl_2$ (9.5 mL) at room temperature, was added TFA (0.5 mL). The reaction was stirred for 1 hour followed by addition of more TFA (0.5 mL) and the reaction stirred for two more hours. The solvents were removed on the rotavap and the residue dried under high vacuum for 15 hours to afford the product (0.54 g). This material, (0.05 g, 0.000084 mole) was dissolved in THF/saturated $NaHCO_3$ (0.5 mL each) at room temperature, dansyl chloride (0.024 g, 0.000088 mole) was added, and the reaction was vigorously stirred for 2 hours during which time a suspension formed. $H_2O$ (4 mL) was added and the aqueous layer was extracted with EtOAc (10 mL). The EtOAc layer was washed with brine (4 mL), dried over $MgSO_4$, filtered and evaporated. Flash chromatography on silica gel using 10% MeOH/$CHCl_3$ afforded the product contaminated with some dansyl chloride. This material was taken up in 10% MeOH/$CHCl_3$ (5 mL) and treated with an amine resin (PS—$NH_2$ 200, 1.86 mmol/g, 100 mg) for 10 minutes and the solvent removed on the rotavap. This process was repeated three times. The resin was taken up in 10%

MeOH/CHCl₃ (5 mL) and filtered through Celite® followed by solvent evaporation and drying under high vacuum produced (2S)-{4-[2-(5-dimethylamino-1-naphthyl)sulfonylamino-2-(4-phenyl-butylcarbamoyl)-ethyl]-phenyl}difluoromethylphosphonic acid diethyl ester (26 mg).

The 2S isomer of Compound 1 was prepared by subjecting the (2S)-{4-[2-(5-dimethylamino-1-naphthyl)sulfonylamino-2-(4-phenyl-butylcarbamoyl)-ethyl]-phenyl}difluoromethyl-phosphonic acid diethyl ester to the procedure of Example 2D below. MS (ion spray):m/z 660.3 (M+H).

Example 2

Synthesis of Compound 2

(2RS)-{4-[2-Benzenesulfonylamino-2-(4-phenylbutylcarbamoyl)-ethyl]-2-bromo-phenyl}difluoromethylphosphonic acid

2

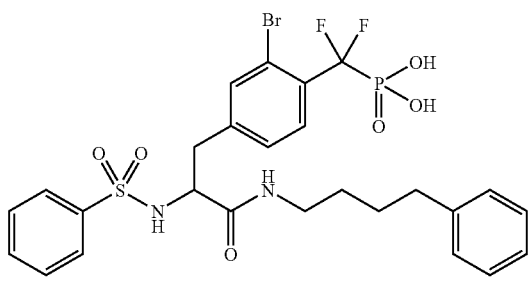

A. The cadmium reagent was generated as in Example 1 using Cd metal (8.5 g, 0.075 mole), diethyl bromodifluoromethylphosphonate (18 g, 0.068 mole) and AcOH (1.0 mL) in DMF (80 mL). A 40 mL aliquot of this solution was added to CuCl (6.72 g, 0.068 mole) followed after 2 minutes by the addition of 3-bromo-4-iodotoluene (5.0 g, 0.017 mole). The reaction suspension was stirred for 28 hours, then more cadmium reagent solution (30 mL) was added and the reaction stirred an additional 4 days. Ether (700 mL) was added and the solution was filtered through Celite®. The Celite® cake was washed with additional ether (300 mL) and the combined ether layer was washed with saturated ammonium chloride (500 mL) and water (500 mL) then dried over magnesium sulfate. Filtration and solvent evaporation left behind 8.5 g of crude product. Flash chromatography on silica gel using 30% ethyl acetate/hexanes afforded 4.4 g of (2-bromo-4-methylphenyl)difluoromethylphosphonic acid diethyl ester. To the diethyl ester material obtained, (1.8 g, 0.005 mole) in carbon tetrachloride (CCl₄, 30 mL), were added AIBN (0.033 g, 0.0002 mole) and N-bromosuccinimide (NBS, 0.89 g, 0.005 mole). The reaction was heated at reflux for 2 hours (a thin white suspension formed). The reaction was allowed to reach room temperature and the solvent was removed under vacuum. The residue was taken up in ethyl acetate (EtOAc, 120 mL) and washed with saturated NaHCO₃ (60 mL) and brine (60 mL) then dried over MgSO₄. Filtration and solvent evaporation afforded 2.1 g of crude product. Flash chromatography on silica gel using 20-30% ethyl acetate/hexanes afforded 1.11 g of (2-bromo-4-bromomethyl-phenyl)-difluoro-methylphosphonic acid diethyl ester.

B. To a solution of tert-butyl diphenyliminoglycine (0.14 g, 0.00048 mole), the (2-bromo-4-bromomethylphenyl)difluoromethylphosphonic acid diethyl ester obtained above (0.21 g, 0.00048 mole) and tetrabutyl ammonium hydrogensulfate (0.16 g, 0.00048 mole) in dichloromethane (CH₂Cl₂, 1.8 mL), at room temperature was added a 10% NaOH solution (1.2 mL) and the reaction was vigorously stirred for 7 hours. The reaction was diluted with CH₂Cl₂ (6 mL) and the CH₂Cl₂ layer was concentrated. The residue was taken up in Et₂O (15 mL) and washed with H₂O (5 mL), brine (5 mL) and dried for 5 minutes over MgSO₄. Filtration and solvent evaporation resulted in 0.25 g of product. Flash chromatography on silica gel using 20% ethyl acetate/hexanes afforded (2RS)-{4-[2-benzhydrylideneamino-2-(tert-butoxycarbonyl)-ethyl]-2-bromophenyl}-difluoromethylphosphonic acid diethyl ester (0.17 g). To this material (0.23 g, 0.00035 mole) in THF (3 mL) at room temperature, was added 1N HCl (10 mL) and the reaction was stirred at room temperature for 2 hours. The aqueous layer was washed with Et₂O (3×10 mL) and concentrated under vacuum, followed by drying under high vacuum for 20 hours to give 0.122 g of intermediate. This intermediate compound was used in the next step without further purification. To the intermediate material (0.12 g, 0.00026 mole) in Et₂O (0.8 mL), at −5° C. were added 1N NaOH (0.8 mL), water (0.8 mL) and benzenesulfonyl chloride (PhSO₂Cl, 0.037 mL, 0.00029 mole) and the reaction was stirred for 1 hour. More PhSO₂Cl (0.037 mL, 0.00029 mole) was added and the reaction stirred an additional 3 hours then allowed to reach room temperature over 2 hours. The aqueous layer was extracted with Et₂O (3×4 mL), acidified with 1N HCl (1 mL), and extracted with Et₂O (3×3 mL). The combined Et₂O layer (from both washes) was evaporated and the residue was treated with MeOH (5 mL) and polystyrene amine resin (PS—NH₂ 200, 120 mg) shaken on rotovap for 5 minutes. The solvent was evaporated, MeOH (5 mL) was added, and the solution filtered through a cotton plug. Solvent evaporation and drying under high vacuum overnight afforded about 0.142 g of sulfonamide acid material.

C. To the sulfonamide acid obtained above (0.11 g, 0.00019 mole) in DMF (2.3 mL) at room temperature, were added HOBt (0.032 g, 0.00021 mole), phenbutyl amine (0.033 mL, 0.00021 mole), EDC (0.04 g, 0.00021 mole) and DIEA (0.1 mL, 0.00057 mole) and the reaction was stirred overnight. EtOAc (15 mL) and 1N HCl (6 mL) were added and the EtOAc layer was washed with saturated NaHCO₃ (6 mL), H₂O (6 mL), and brine (6 mL), then dried over MgSO₄. Filtration and solvent evaporation followed by flash chromatography on silica gel using 60% ethyl acetate/hexanes afforded the pure (2RS)-{4-[2-benzenesulfonylamino-2-(4-phenylbutyl-carbamoyl)-ethyl]-2-bromo-phenyl}difluoromethylphosphonic acid diethyl ester (0.028 g).

D. To this phenbutyl amide compound (0.028 g) in CH₂Cl₂ (0.5 mL) at room temperature, was added trimethylsilyl bromide (0.1 mL) and the reaction was stirred at room temperature overnight. The CH₂Cl₂ was removed and the residue was taken up in CH₂Cl₂ (1 mL) and the solvent removed again. The residue was dried under high vacuum for 40 minutes then dissolved in CH₂Cl₂ (0.5 mL) and treated with H₂O (0.5 mL) and the resultant reaction was stirred for 1 hour. CH₂Cl₂ was removed on the rotavap and the aqueous solution was transferred to a vial with the aid of H₂O, frozen and lyophilized to give the pure Compound 2 (0.025 g). MS (ion spray):m/z 643.3/645.2 (N—H); 645.2/647.1 (M+H). ¹H NMR: (DMSO-d₆, 400 MHz) δ 8.12 (d, 1H, J=9.2 Hz) 7.89 (t, 1H, J=5.2 Hz), 7.53 (m, 2H), 7.48 (m, 3H), 7.37 (m, 2H), 7.26 (m, 2H), 7.17 (m, 4H), 3.91 (m, 1H), 2.81 (m, 3H), 2.65 (m, 1H), 2.49 (m, 2H), 1.43 (m, 2H), 1.22 (m, 2H).

Example 3

Synthesis of Compound 3

(2RS)-(4-{2-Benzenesulfonylamino-2-[4-(2-methoxycarbonyl-3-hydroxy-phenoxy)-butylcarbamoyl]ethyl}-2-bromophenyl)difluoromethylphosphonic acid diethyl ester, and (2RS)-(4-{2-Benzenesulfonylamino-2-[4-(2-methoxycarbonyl-3-hydroxy-phenoxy)-butylcarbamoyl]ethyl}-2-bromophenyl)difluoromethylphosphonic acid

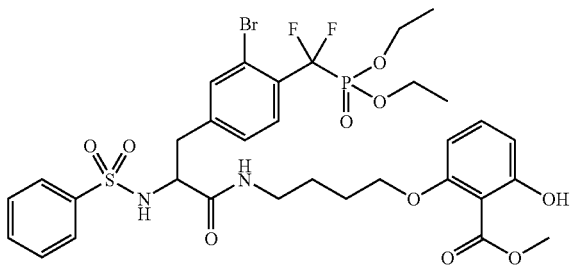

(2RS)-(4-{2-Benzenesulfonylamino-2-[4-(2-methoxycarbonyl-3-hydroxy-phenoxy)butylcarbamoyl]-ethyl}-2-bromo-phenyl)difluoromethylphosphonic acid diethyl ester
$C_{32}H_{38}BrF_2N_2O_{10}PS$
Exact Mass: 790.11

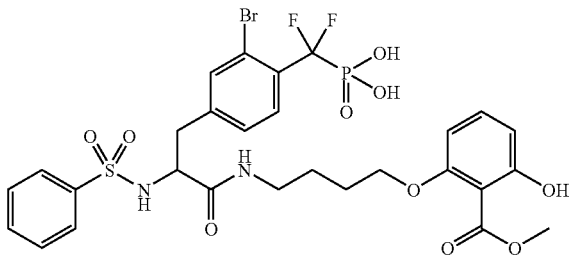

(2RS)-(4-{2-Benzenesulfonylamino-2-[4-(2-methoxycarbonyl-3-hydroxy-phenoxy)butylcarbamoyl]-ethyl}-2-bromo-phenyl)difluoromethylphosphonic acid
$C_{28}H_{30}BrF_2N_2O_{10}PS$
Exact Mass: 734.05

(2RS)-(4-{2-Benzenesulfonylamino-2-[4-(2-methoxycarbonyl-3-hydroxy-phenoxy)butylcarbamoyl]ethyl}-2-bromophenyl)difluoromethylphosphonic acid diethyl ester (Compound 3A) was prepared from the sulfonamide acid obtained in Example 2B following a procedure similar to Example 2C except that 2-(4-amino-butoxy)-6-hydroxybenzoic acid methyl ester was used instead of phenbutylamine. The 2-(4-amino-butoxy)-6-hydroxy-benzoic acid methyl ester was prepared by taking a solution of 2,6-dihydroxymethylbenzoate (1.0 g, 5.95 mmol), 1.5 equivalents N-Boc aminobutanol and 1.5 equivalents of triphenylphosphine (2.34 g, 8.93 mmol) in 40 mL of $CH_2Cl_2$ and adding 1.5 equivalents of DIAD (1.80 g, 8.93 mmol). Stirring continued for 1.5 hours at room temperature. Evaporation to dryness followed by column chromatography (30% EtOAc/hexanes) gave 2-(4-tert-butoxycarbonylamino-butoxy)-6-hydroxybenzoic acid methyl ester. This compound was cooled to 0° C. in an ice/brine bath. HCl gas was bubbled into the solution for 2 minutes and stirring was continued for 1 hour. Evaporation to dryness followed by precipitation with ether and filtration gave 2-(4-aminobutoxy)-6-hydroxybenzoic acid methyl ester as the HCl salt. Compound 3 was prepared from Compound 3A following the procedures in Example 2D. MS (ion spray): m/z 733.4/735.4 (M–H). $^1$H NMR: (DMSO-$d_6$, 400 MHz) δ 9.91 (br s, 1H), 8.15 (d, 1H, J=9.2 Hz), 7.94 (br s, 1H), 7.55 (d, 2H, J=8.0 Hz), 7.46 (m, 5H), 7.21 (d, 1H, J=8.0 Hz), 7.15 (t, 1H, J=8.0 Hz), 6.47 (m, 2H), 3.95 (m, 1H), 3.85 (m, 2H), 3.72 (s, 3H), 2.85 (m, 3H), 2.65 (m, 1H), 1.49 (m, 2H), 1.35 (m, 2H).

Example 4

Synthesis of Compound 4

(2S)-{4-[2-Benzyloxycarbonylamino-2-(carboxy)-ethyl]-phenyl}difluoromethyl-phosphonic acid diethyl ester

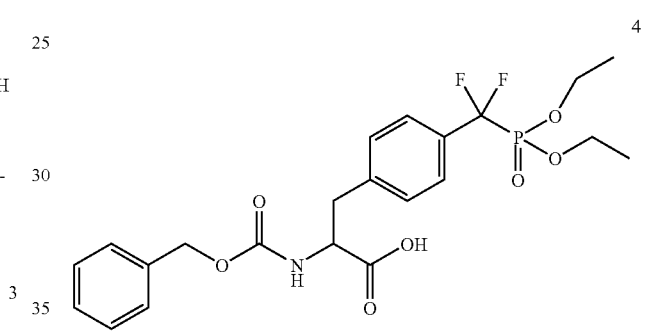

A slurry of L-4-Iodo-Phe (5.0 g, 17.2 mmol) in 100 mL of MeOH was cooled to 0 degrees in an ice/brine bath. HCl gas was bubbled into the mixture for 5 minutes at which time the starting material dissolved. The mixture was allowed to warm to room temperature and stirring was continued for 16 hours. Evaporation to dryness followed by precipitation with ether and filtration gave 4.62 g (79%) of L-4'-Iodo-Phe —OMe, (2S)-2-amino-3-(4-iodophenyl)-propionic acid methyl ester as the HCl salt. To 4.0 g (11.7 mmol) of the obtained propionic acid methyl ester HCl salt, in 250 mL of THF/$H_2O$ (1:1) was added 2.0 equivalents of $Na_2CO_3$ followed by 1.01 equivalents of Z—OSu (2.94 g, 11.8 mmol). The mixture was stirred at room temperature for 4 hours followed by extraction with 2×200 mL of EtOAc. The combined organic layers were dried over $Na_2SO_4$ and evaporated. Column chromatography (20% EtOAc/hexanes) gave 3.89 g (76%) of Cbz-L-4'-Iodo-Phe-OMe, (2S)-2-amino-3-(4-iodophenyl)-propionic acid methyl ester. (2S)-{4-[2-Benzyloxycarbonylamino-2-(methoxycarbonyl)ethyl]phenyl}difluoromethyl-phosphonic acid diethyl ester was prepared from the previously obtained Cbz-L-4'-Iodo-Phe-OMe, (2S)-2-Amino-3-(4-iodophenyl)-propionic acid methyl ester following the procedure used to make the (2-bromo-4-methyl-phenyl)difluoro-methylphosphonic acid diethyl ester in Example 2.

To 3.92 g (7.85 mmol) of the (2S)-{4-[2-benzyloxycarbonylamino-2-(methoxy-carbonyl)-ethyl]-phenyl}-difluoromethylphosphonic acid diethyl ester obtained above, in 50 mL of THF at 0° C. was added 2 equivalents of LiOH (0.66 g, 15.7 mmol) in 50 mL of $H_2O$. Stirring was continued for 15 minutes at which time TLC indicated absence of starting material.

The mixture was poured into 250 mL of EtOAc and 150 mL of 1N HCl. The aqueous layer was then extracted with an additional 100 mL of EtOAc. The combined organic layers were dried over Na$_2$SO$_4$ and evaporated. Column chromatography (1-5% MeOH/CH$_2$Cl$_2$) gave 3.5 g (92%) of Compound 4. $^1$H NMR: (DMSO-d$_6$, 400 MHz) δ 12.77 (s, 1H), 7.70 (d, 1H), 7.45 (d, 2H), 7.40 (d, 2H), 7.34-7.20 (m, 5H), 4.94 (m, 2H), 4.20 (m, 1H), 4.08 (m, 4H), 3.12 (dd, 1H), 2.89 (dd, 1H). 1.18 (t, 6H).

Example 5

Synthesis of Compound 5

(2S)-{4-[2-Benzyloxycarbonylamino-2-(3-phenyl-propylcarbamoyl)-ethyl]-phenyl}difluoromethylphosphonic acid

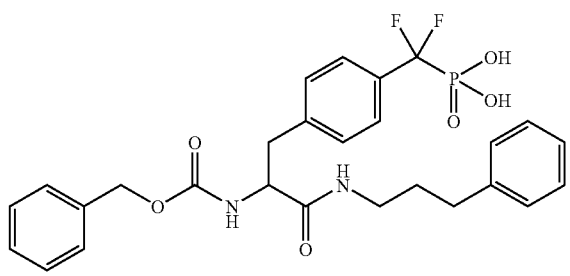

5

(2S)-{4-[2-Benzyloxycarbonylamino-2-(3-phenylpropyl-carbamoyl)-ethyl]-phenyl}-difluoromethylphosphonic acid diethyl ester was prepared from Compound 4 and phenpropylamine following procedure C in Example 2. Compound 5 was prepared from the resultant material following the procedure described in Example 2D. MS (ion spray):m/z 547.3 (M+H). $^1$H NMR: (DMSO-d$_6$, 400 MHz) δ 8.04 (t, 1H), 7.51 (d, 1H), 7.42 (d, 2H), 7.33-7.13 (m, 12H), 4.93 (m, 2H), 3.05 (m, 2H), 2.95 (dd, 1H), 2.79 (dd, 1H), 2.53 (t, 2H), 1.66 (m, 2H).

Example 6

Synthesis of Compound 6

(2S)-{4-[2-Phenylsulfonylamino-2-(4-phenylbutyl-carbamoyl)-ethyl]-phenyl}difluoro-methylphosphonic acid

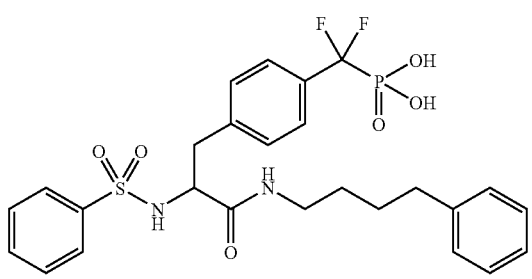

6

(2S)-{4-[2-phenylsulfonylamino-2-(4-phenylbutylcarbamoyl)-ethyl]-phenyl}difluoromethylphosphonic acid A solution of 200 mg of (2S)-{4-[2-Benzyloxycarbony-lamino-2-(4-phenylbutylcarbamoyl)-ethyl]-phenyl}-difluoromethylphosphonic acid diethyl ester (prepared from Compound 4 and phenbutylamine following procedure C in Example 2) was degassed with a stream of nitrogen gas for 2 minutes with stirring. Five percent Pd/C (40 mg) was added and a vacuum was applied for 1 minute until bubbling occurred. A balloon of hydrogen gas was applied and stirring continued for 30 minutes at which time TLC indicated absence of starting material. The mixture was filtered over a bed of Celite® and evaporated to dryness. The amine product was dissolved in 5 mL of THF. Five mL of saturated NaHCO$_3$ was added followed by 1 equivalent of benzene sulfonyl chloride with stirring. The reaction was poured into 25 mL of EtOAc and 25 mL of H$_2$O. The aqueous layer was then extracted with an additional 25 mL of EtOAc. The organic layers were combined, dried over Na$_2$SO$_4$ and evaporated. Column chromatography (3% MeOH/CH$_2$Cl$_2$) gave 121 mg (60%) of (2S)-{4-[2-phenylsulfonylamino-2-(4-phenyl-butylcarbamoyl)ethyl]-phenyl}difluoromethylphosphonic acid diethyl ester. Compound 6 was prepared from this material following the procedure described in Example 2. MS (ion spray):m/z 567.4 (M+H). $^1$H NMR: (DMSO-d$_6$, 400 MHz) δ 8.08 (d, 1H), 7.86 (t, 1H), 7.57 (d, 2H), 7.49 (t, 1H), 7.41-7.35 (m, 4H), 7.29-7.25 (m, 4H), 7.17-7.14 (m, 3H), 3.93 (m, 1H), 2.84-2.74 (m, 3H), 2.66 (dd, 1H), 2.49 (m, 2H), 1.40 (m, 2H), 1.17 (m, 2H).

Example 7

Synthesis of Compound 7

(2S)-{4-[2-Benzyloxycarbonylamino-2-(4-phenylbu-tylcarbamoyl)-ethyl]-phenyl}difluoromethylphosphonic acid

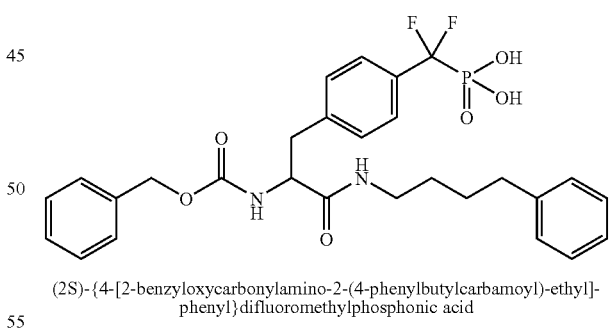

7

(2S)-{4-[2-benzyloxycarbonylamino-2-(4-phenylbutylcarbamoyl)-ethyl]-phenyl}difluoromethylphosphonic acid (2S)-{4-[2-Benzyloxycarbonylamino-2-(4-phenylbutyl-carbamoyl)-ethyl]-phenyl}-difluoromethylphosphonic acid diethyl ester was prepared from Compound 4 and phenbuty-lamine following procedure C in Example 2D. Compound 7 was then prepared from this material by following the procedure described in Example 2D. MS (ion spray):m/z 561.4 (M+H). $^1$H NMR: (DMSO-d$_6$, 400 MHz) δ 7.98 (t, 1H), 7.48 (d, 1H), 7.39 (m, 4H), 7.32-7.12 (m, 10H), 4.92 (s, 2H), 4.17 (m, 1H), 3.05 (m, 2H), 2.93 (dd, 1H), 2.77 (dd, 1H), 2.52 (t, 2H), 1.52 (m, 2H), 1.37 (m, 2H).

Example 8

Synthesis of Compound 8

(2S)-(4-{2-Benzyloxycarbonylamino-2-[4-(2-methoxycarbonyl-3-hydroxy-phenoxy)-butylcarbamoyl]-ethyl}-phenyl)difluoromethylphosphonic acid

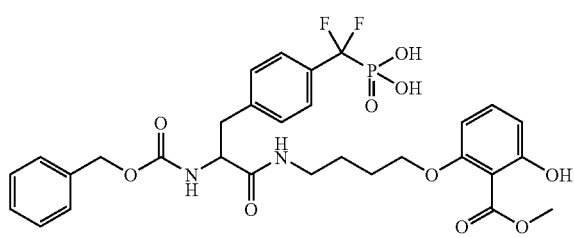

8

(2S)-(4-{2-benzyloxycarbonylamino-2-[4-(2-methoxycarbonyl)-3-hydroxy-phenoxy)butylcarbamoyl]-ethyl}-phenyl)difluoromethylphosphonic acid (2S)-(4-{2-Benzyloxycarbonylamino-2-[4-(2-methoxycarbonyl-3-hydroxy-phenoxy)-butylcarbamoyl]-ethyl}-phenyl)difluoromethylphosphonic acid diethyl ester was prepared from Compound 4 and 2-(4-amino-butoxy)-6-hydroxy-benzoic acid methyl ester following procedures in Example 2C. Compound 8 was prepared from the (2S)-(4-{2-benzyloxycarbonylamino-2-[4-(2-methoxycarbonyl-3-hydroxy-phenoxy)-butyl-carbamoyl]-ethyl}-phenyl)difluoromethylphosphonic acid diethyl ester following the procedure described in Example 2D. MS (ion spray):m/z 651.3 (M+H). $^1$H NMR: (DMSO-$d_6$, 400 MHz) δ 8.02 (t, 1H), 7.51 (d, 1H), 7.41 (d, 2H), 7.35-7.24 (m, 7H), 7.14 (t, 1H), 6.46 (m, 2H), 4.94, (s, 2H), 4.20 (m, 1H), 3.92 (t, 2H), 3.71 (s, 3H), 3.09 (m, 3H), 2.80 (dd, 1H), 1.57 (m, 2H), 1.48 (m, 2H).

Example 9

Synthesis of Compound 9

(2S)-(4-{2-Phenylsulfonylamino-2-[4-(2-methoxycarbonyl-3-hydroxy-phenoxy)butylcarbamoyl]-ethyl}-phenyl)difluoromethylphosphonic acid

9

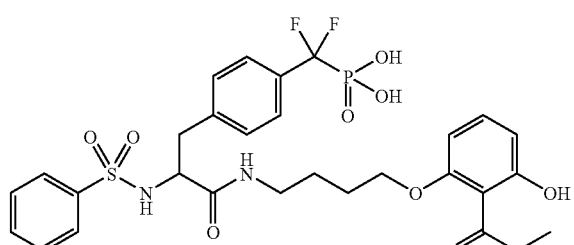

(2S)-(4-{2-phenylsulfonylamino-2-[4-(2-methoxycarbonyl)-3-hydroxy-phenoxy)butylcarbamoyl]-ethyl}-phenyl)difluoromethylphosphonic acid (2S)-(4-{2-Phenylsulfonylamino-2-[4-(2-methoxycarbonyl-3-hydroxy-phenoxy)-butyl-carbamoyl]-ethyl}-phenyl) difluoromethylphosphonic acid diethyl ester was prepared following the procedure in Example 6 using (2S)-(4-{2-benzyloxycarbonyl-amino-2-[4-(2-methoxycarbonyl-3-hydroxyphenoxy)butylcarbamoyl]-ethyl}-phenyl)-difluoro-methylphosphonic acid diethyl ester as the starting material. This material was used to prepare Compound 9 following the procedure described in Example 2D. MS (ion spray):m/z 657.3 (M+H). $^1$H NMR: (DMSO-$d_6$, 400 MHz) δ 9.92 (s, 1H), 8.11 (d, 1H), 7.90 (t, 1H), 7.57 (d, 2H), 7.49 (t, 1H), 7.43-7.36 (m, 4H), 7.20 (d, 2H), 7.15 (t, 1H), 6.46 (d, 2H), 4.05 (m, 4H), 3.93 (m, 1H), 3.84 (t, 2H), 3.71 (s, 3H), 2.86-2.76 (m, 3H), 2.69 (dd, 1H), 1.43 (m, 2H), 1.28 (m, 2H).

Example 10

Synthesis of Compound 10

(2S)-(4-{2-Methylsulfonylamino-2-[4-(2-methoxycarbonyl-3-hydroxyphenoxy)butylcarbamoyl]-ethyl}-phenyl)difluoromethylphosphonic acid

10

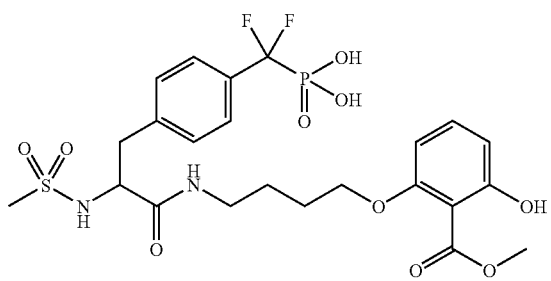

(2S)-(4-{2-methylsulfonylamino-2-[4-(2-methoxycarbonyl-3-hydroxy-phenoxy)butylcarbamoyl]-ethyl}-phenyl)difluoromethylphosphonic acid (2S)-(4-{2-Methylsulfonylamino-2-[4-(2-methoxycarbonyl-3-hydroxy-phenoxy)-butyl-carbamoyl]-ethyl}-phenyl) difluoromethylphosphonic acid diethyl ester was prepared following the procedure in Example 6 using (2S)-(4-{2-benzyloxycarbonyl-amino-2-[4-(2-methoxycarbonyl-3-hydroxyphenoxy)butylcarbamoyl]-ethyl}-phenyl)-difluoromethylphosphonic acid diethyl ester and methanesulfonyl chloride as the starting materials, then treated as in Example 2D to yield Compound 10. $^1$H NMR: (DMSO-$d_6$, 400 MHz) δ 8.13 (t, 1H), 7.57 (d, 1H), 7.45 (d, 2H), 7.36 (d, 2H), 7.14 (t, 1H), 6.46 (m, 2H), 4.02 (m, 1H), 3.92 (t, 2H), 3.71 (s, 3H), 3.08 (m, 2H), 2.95 (dd, 1H), 2.79 (dd, 1H), 2.55 (s, 3H), 1.57 (m, 2H), 1.46 (m, 2H).

Example 11

Synthesis of Compound 11
(2S)-{4-[2-Benzyloxycarbonylamino-2-(3-phenoxy-propylcarbamoyl)-ethyl]-phenyl}difluoromethylphosphonic acid

11

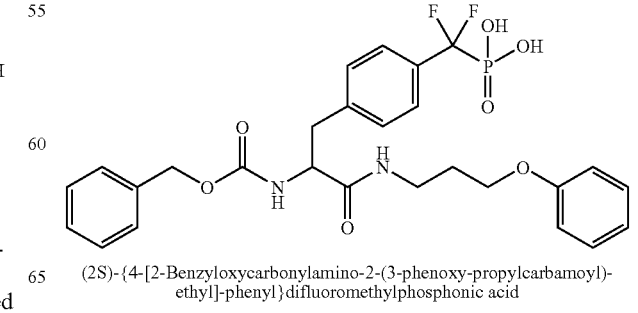

(2S)-{4-[2-Benzyloxycarbonylamino-2-(3-phenoxy-propylcarbamoyl)-ethyl]-phenyl}difluoromethylphosphonic acid A. A solution of Compound 4 (470 mg, 0.97 mmol) and NHS (138 mg, 1.2 mmol) in 5 mL of $CH_2Cl_2$ was treated with 225 mg (1.2 mmol) of EDC. After 20 minutes, the reaction mixture was charged with 96 μL of 3-amino-1-propanol (1.2 mmol) and 372 μL of DIEA (2.1 mmol). After stirring for 3 days, the solution was diluted with $CH_2Cl_2$ and quenched with 1M aqueous HCl. The phases were partitioned, and the organic layer was further washed with water. The organic solution was then dried ($Na_2SO_4$), decanted and concentrated. Chromatography over silica gel using 5% methanolic $CH_2Cl_2$ afforded 285 mg of (2S)-{4-[2-benzyloxycarbonylamino-2-(3-hydroxypropylcarbamoyl)-ethyl]-phenyl}-difluoromethylphosphonic acid diethyl ester. (54%).

B. A solution of this material (282 mg, 0.52 mmol) and phenol (51 mg, 0.54 mmol) in 20 mL of THF was cooled to 0° C. and treated with 110 μL of DIAD (0.57 mmol). After stirring for 20 hours, the reaction mixture was concentrated under vacuum and dissolved into 25 mL of EtOAc and washed sequentially with 5% aqueous $NaHCO_3$ (2×25 mL) and brine (1×25 mL). After drying over $Na_2SO_4$, the solution was decanted and concentrated to 583 mg. Chromatography over silica gel using 50-100% EtOAc in hexanes afforded 50 mg of (2S)-{4-[2-benzyloxycarbonylamino-2-(3-phenoxy-propylcarbamoyl)ethyl]phenyl}difluoromethylphosphonic acid diethyl ester (15%).

C. A solution of this material (49 mg, 79 μmol) in $CH_2Cl_2$ was treated with 500 μL of bromotrimethylsilane. The solution was stirred overnight, and then concentrated to dryness under vacuum and dissolved in $CH_2Cl_2$ and re-concentrated under vacuum to afford solids. The solids were stored under vacuum for 4 hours, and then treated with 3 mL benzene, 2 mL of distilled water and 38 mg (0.47 mmol) of $NaHCO_3$. The resultant white slurry was stirred for 15 minutes before allowing to settle and partition. The aqueous was washed with 3 mL benzene, frozen and then lyophilyzed to dryness, reconstituted with 15 mL distilled water, refrozen and lyophilyzed again. Further purification by HPLC resulted in 15.7 mg of Compound 11 (35%). MS (ion spray):m/z 563.3 (M+H), 561.3 (M–H). $^1$H NMR: (DMSO-$d_6$, 400 MHz) δ 8.06 (dd, 1H), 7.49 (d, 1H), 7.36 (d, 2H) 7.18-7.30 (m, 9H), 6.83-6.86 (m, 3H), 4.88 (s, 2H), 4.11-4.17 (m, 1H), 3.85-3.88 (m, 2H), 3.13-3.20 (m, 2H), 2.91-2.94 (m, 2H) 2.70-2.78 (m, 1H), 1.77-1.78 (m, 2H).

Example 12

Synthesis of Compound 12
(2S)-(4-{2-Benzyloxycarbonylamino-2-[4-(2-methoxycarbonyl-3-methyl-phenoxy)butyl-carbamoyl]-ethyl}-phenyl)difluoromethylphosphonic acid

12

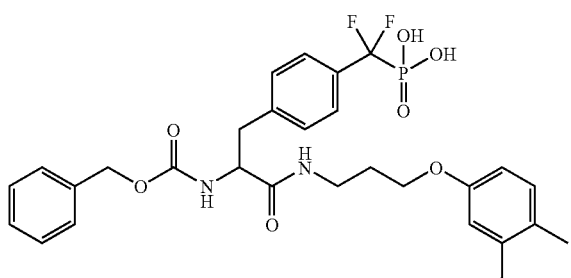

(2S)-(4-{2-benzyloxycarbonylamino-2-[4-(2-methoxycarbonyl-3-methyl-phenoxy)butylcarbamoyl]-ethyl}-phenyl)difluoromethylphosphonic acid (2S)-(4-{2-Benzyloxycarbonylamino-2-[4-(2-methoxycarbonyl-3-methyl-phenoxy)-butylcarbamoyl]-ethyl}-phenyl)difluoromethylphosphonic acid diethyl ester was prepared from Compound 4 following the coupling procedure of Example 1A, with the exception that 2-(4-amino-butoxy)-6-methyl-benzoic acid methyl ester was employed as the coupling partner. Chromatography over silica gel using 2% methanolic $CH_2Cl_2$ afforded the product (23%). Compound 12 was prepared by starting with the product of the previous procedure and then following the deprotection procedure of Example 11C, yielding 57 mg. This material was further purified by HPLC, resulting in 7.4 mg of Compound 12 (8%). MS (ion spray):m/z 649.3 (M+H), 647.3 (M–H). $^1$H NMR: (DMSO-$d_6$, 400 MHz) δ 8.03 (dd, 1H), 7.52 (d, 1H), 7.23-7.42 (m, 100H), 6.88 (s, 1H), 6.80 (s, 1H), 4.93 (s, 2H), 4.17-4.23 (m, 1H), 3.94 (dd, 2H), 3.76 (s, 3H), 3.03-3.10 (m, 2H), 2.90-2.98 (m, 1H), 2.15 (s, 3H), 1.57-1.60 (m, 2H), 1.43-1.49 (m, 2H), 1.22 (s, 3H).

Example 13

Synthesis of Compound 13

(2S)-(4-{2-Benzyloxycarbonylamino-2-[3-(4-methoxy-phenoxy)propylcarbamoyl]-ethyl}-phenyl)difluoromethylphosphonic acid

13

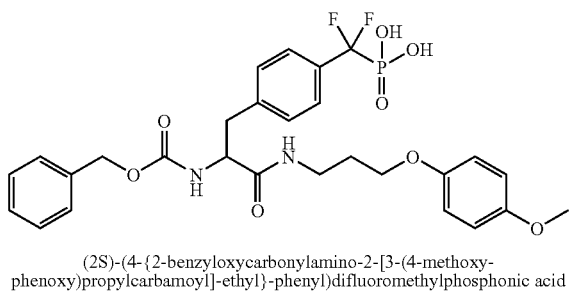

(2S)-(4-{2-benzyloxycarbonylamino-2-[3-(4-methoxy-phenoxy)propylcarbamoyl]-ethyl}-phenyl)difluoromethylphosphonic acid Compound 13 was prepared from Compound 4 generally following the coupling procedure of Example 11A, with the exception that 3-(4-methoxy-phenoxy)-propylamine was employed as the coupling partner, and dicyclohexylcarbodiimide as the coupling agent. Chromatography over silica gel using 30% EtOAc in hexanes, followed by 1 to 3% methanolic $CH_2Cl_2$ afforded 103 mg of (2S)-(4-{2-benzyloxycarbonylamino-2-[3-(4-methoxy-phenoxy)propylcarbamoyl]-ethyl}-phenyl)difluoromethylphosphonic acid di-ethyl ester (78%). This material was then converted to Compound 13 following the deprotection procedures of Example 11C, followed by purification by HPLC, yielding 29 mg of product (31%). MS (ion spray):m/z 593.3 (M+H), 591.4 (M–H). $^1$H NMR: (DMSO-$d_6$, 400 MHz) δ 8.10 (dd, 1H), 7.52 (d, 1H), 7.23-7.42 (m, 9H), 6.82 (s, 4H), 4.93 (s, 2H), 4.18-4.20 (m, 1H), 3.85 (dd, 2H), 3.66 (s, 3H), 3.18-3.35 (m, 2H), 2.94-2.98 (m, 1H), 2.78-2.82 (m, 1H), 1.75-1.79 (m, 2H).

Example 14

Synthesis of Compound 14

(2S)-(4-{2-Benzyloxycarbonylamino-2-[3-(4-chlorophenoxy)propylcarbamoyl]-ethyl}-phenyl)difluoromethylphosphonic acid

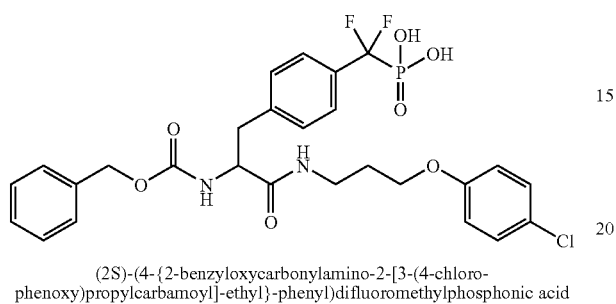

(2S)-(4-{2-benzyloxycarbonylamino-2-[3-(4-chlorophenoxy)propylcarbamoyl]-ethyl}-phenyl)difluoromethylphosphonic acid Compound 14 was prepared from Compound 4 following the coupling procedure of Example 11A, with the exception that 3-(4-chlorophenoxy)-propylamine was employed as the coupling partner, and 0.5M HOAt in DMF was substituted for NHS. Multiple chromatographies over silica gel using 2% methanolic $CH_2Cl_2$ and 50-100% EtOAc in hexanes afforded (2S)-(4-{2-benzyloxycarbonylamino-2-[3-(4-chloro-phenoxy)propyl-carbamoyl]ethyl}phenyl)difluoromethylphosphonic acid diethyl ester (10%). This material was then converted to Compound 14 following the deprotection procedure of Example 11C, followed by purification by HPLC, yielding 6.9 mg of Compound 14 (45%). MS (ion spray):m/z 597.2 (M+H), 595.4 (M−H). $^1$H NMR: (DMSO-$d_6$, 400 MHz) δ 8.10 (dd, 1H), 7.52 (d, 1H), 7.23-7.42 (m, 9H), 6.90 (d, 2H), 4.93 (s, 2H), 4.18-4.20 (m, 1H), 3.85 (dd, 2H), 3.18-3.35 (m, 2H), 2.94-2.98 (m, 1H), 2.78-2.82 (m, 1H), 1.75-1.79 (m, 2H).

Example 15

Synthesis of Compound 15

(2S)-{4-[2-Benzyloxycarbonylamino-2-(4-phenoxy-butylcarbamoyl)-ethyl]-phenyl}-difluoromethylphosphonic acid diethyl ester

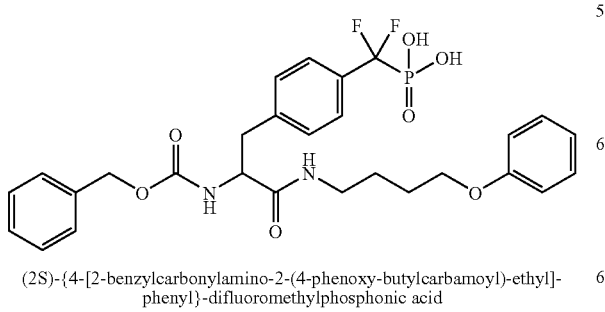

(2S)-{4-[2-benzylcarbonylamino-2-(4-phenoxy-butylcarbamoyl)-ethyl]-phenyl}-difluoromethylphosphonic acid Compound 15 was prepared from Compound 4 following the coupling procedure of Example 11A, with the exception that 4-phenoxy-butylamine was employed as the coupling partner, and HOBt in DMF was substituted for NHS. Chromatography over silica gel using 1-2% methanolic $CH_2Cl_2$ afforded (2S)-{4-[2-benzyloxycarbonylamino-2-(4-phenoxy-butyl-carbamoyl)-ethyl]-phenyl}-difluoromethylphosphonic acid diethyl ester (38%). This material was then converted into Compound 15 following the deprotection procedure of Example 11C, followed by purification by HPLC, yielding 7.3 mg of Compound 15 (15%). MS (ion spray):m/z 577.2 (M+H), 575.2 (M−H). $^1$H NMR: (DMSO-$d_6$, 400 MHz) δ 8.03 (dd, 1H), 7.52 (d, 1H), 7.23-7.42 (m, 10H), 6.87-6.90 (m, 3H), 4.93 (s, 2H), 4.17-4.20 (m, 1H), 3.92 (dd, 2H), 3.10 (ddd, 2H), 2.97 (ddd, 1H), 2.78 (ddd, 1H), 1.63-1.67 (m, 2H), 1.49-1.54 (m, 2H), 1.22 (s, 1H)

Example 16

Synthesis of Compound 16

(2S)-(4-{2-Benzyloxycarbonylamino-2-[4-(3-hydroxy-phenoxy)-butylcarbamoyl]-ethyl}-phenyl)-difluoromethylphosphonic acid ![Structure of compound 16]

(2S)-(4-{2-benzyloxycarbonylamino-2-[4-(3-hydroxy-phenoxy)-butylcarbamoyl]-ethyl}-phenyl)-difluoromethylphosphonic acid Compound 16 was prepared from Compound 4 following the coupling procedure of Example 11A, with the exception that 3-(4-amino-butoxy)-phenol was employed as the coupling partner, and HOBT in DMF was substituted for NHS. Chromatography over silica gel using 1-4% methanolic $CH_2Cl_2$ afforded the intermediate (2S)-(4-{2-benzyl-oxycarbonylamino-2-[4-(3-hydroxy-phenoxy)-butylcarbamoyl]-ethyl}-phenyl)-difluoro-methylphosphonic acid diethyl ester (52%). This material was then converted into Compound 16 following the deprotection procedure of Example 11C, yielding 47 mg of product (57%). MS (ion spray):m/z 593.2 (M+H), 591.2 (M−H). $^1$H NMR: (DMSO-$d_6$, 400 MHz) δ 8.03 (dd, 1H), 7.50 (d, 1H), 7.24-7.42 (m, 10H), 7.01 (dd, 1H), 6.30-6.34 (m, 3H), 4.94 (s, 2H), 4.16-4.24 (m, 2H), 3.86 (dd, 2H), 3.06-3.15 (m, 2H), 2.94-3.00 (m, 1H), 2.80 (dd, 1H), 1.60-1.68 (m, 2H), 1.46-1.54 (m, 2H).

Example 17
Synthesis of Compound 17
(2S)-(4-{2-Benzyloxyarbonylamino-2-[4-(2-methoxycarbonylphenoxy)butyl-carbamoyl]-ethyl}-phenyl)difluoromethylphosphonic acid ![Structure of compound 17]

(2S)-(4-{2-benzyloxycarbonylamino-2-[4-(2-methoxycarbonyl-phenoxy)butylcarbamoyl]-ethyl}-phenyl)difluoromethylphosphonic acid Compound 17 was prepared from Compound 4 following the coupling procedure of Example 11A, with the exception that 2-(4-amino-butoxy)-benzoic acid methyl ester was employed as the coupling partner, and diisopropylcarbodiimide as the coupling agent. Multiple chromatographies over silica gel using 2.5-5% methanolic $CH_2Cl_2$, then 50-100% EtOAc in hexanes afforded the intermediate compound (2S)-(4-{2-benzyloxycarbonyl-amino-2-[4-(2-methoxycarbonylphenoxy)butylcarbamoyl]-ethyl}-phenyl)-difluoro-methylphosphonic acid diethyl ester (63%). This material was then converted into Compound 17 following the deprotection procedure of Example 11C, followed by purification by HPLC yielding 23.1 mg of Compound 17 (16%). MS (ion spray): m/z 635.2 (M+1H), 633.3 (M–H). $^1$H NMR: (DMSO-$d_6$, 400 MHz) δ 8.04 (dd, 1H), 7.60 (dd, 1H), 7.46-7.54 (m, 2H), 7.21-7.43 (m, 9H), 7.10 (d, 1H), 6.98 (dd, 1H), 4.93 (s, 2H), 4.18-4.24 (m, 1H), 4.00 (dd, 2H), 3.75 (s, 3H), 3.08-3.16 (m, 2H), 2.94-3.00 (m 2H), 2.76-2.84 (m, 1H), 1.60-1.70 (m, 2H), 1.50-1.60 (m, 2H).

Example 18

Synthesis of Compound 18

(2S)-(4-{2-Benzyloxycarbonylamino-2-[3-(4-acetyl-2-nitro-phenoxy)-propylcarbamoyl]-ethyl}-phenyl)difluoromethylphosphonic acid

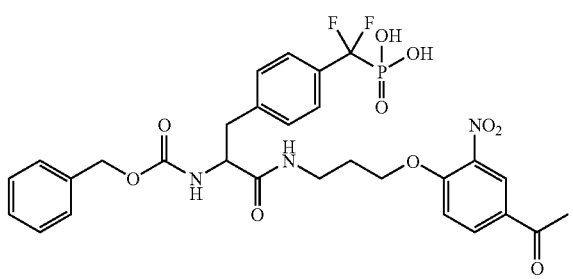

(2S)-(4-{2-benzyloxycarbonylamino-2-[3-(4-acetyl-2-nitro-phenoxy)-propylcarbamoyl]-ethyl}-phenyl)difluoromethylphosphonic acid Compound 18 was prepared from Compound 4 following the coupling procedure of Example 11A, with the exception that 1-[4-(3-amino-propoxy)-3-nitro-phenyl]-ethanone was employed as the coupling partner. Chromatography over silica gel using 1 to 4% methanolic $CH_2Cl_2$ afforded 47 mg of the intermediate compound (2S)-(4-{2-benzyloxy-carbonylamino-2-[3-(4-acetyl-2-nitrophenoxy)-propylcarbamoyl]-ethyl}-phenyl)difluoro-methylphosphonic acid diethyl ester (32%). This material was then converted into Compound 18 following the deprotection procedure of Example 11C, followed by purification by HPLC yielding 23.1 mg of Compound 18 (69%).

Example 19

Synthesis of Compound 19

(2S)-(4-{2-Benzyloxycarbonylamino-2-[3-(4-methyl-phenoxy)-propylcarbamoyl]-ethyl}-phenyl)difluoromethylphosphonic acid

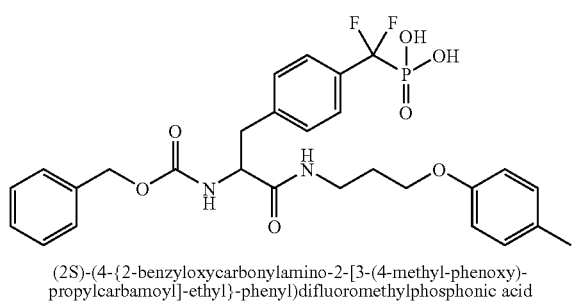

(2S)-(4-{2-benzyloxycarbonylamino-2-[3-(4-methyl-phenoxy)-propylcarbamoyl]-ethyl}-phenyl)difluoromethylphosphonic acid Compound 19 was prepared from Compound 4 following the coupling procedure of Example 11A, with the exception that 3-p-tolyloxy-propylamine was employed as the coupling partner and 0.5M HOAt in DMF was substituted for NHS. Multiple chromatographies over silica gel using 1 to 4% methanolic $CH_2Cl_2$ and 50% EtOAc in hexanes afforded 37 mg of the intermediate compound (2S)-(4-{2-benzyloxy-carbonylamino-2-[3-(4-methyl-phenoxy)-propylcarbamoyl]-ethyl}-phenyl)-difluoro-methylphosphonic acid diethyl ester (29%). This material was then converted into Compound 19 following the deprotection procedure of Example 11C, followed by purification by HPLC yielding 17 mg of Compound 19 (46%). MS (ion spray):m/z 577.3 (M+H), 575.4 (M–H). $^1$H NMR: (DMSO-$d_6$, 400 MHz) δ 8.10 (s, 1H), 7.52 (d, 1H), 7.23-7.44 (m, 8H), 7.04 (d, 2H), 6.78 (d, 2H), 4.93 (s, 2H), 4.20 (br m, 1H), 3.88 (br m, 2H), 3.15-3.24 (m, 2H), 2.92-3.00 (m, 2H), 2.75-2.84 (m, 1H), 2.20 (s, 3H).

Example 20

Synthesis of Compound 20

(2S)-(4-{2-Benzyloxycarbonylamino-2-[3-(3,4-dichloro-phenoxy)-propylcarbamoyl]-ethyl}-phenyl)difluoromethylphosphonic acid

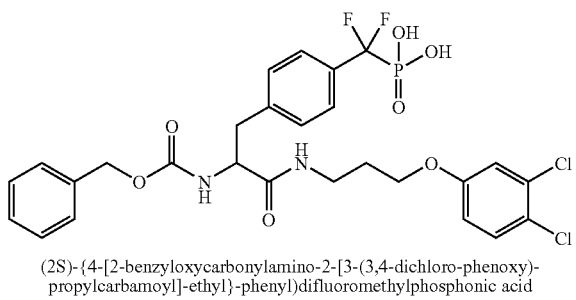

(2S)-{4-[2-benzyloxycarbonylamino-2-[3-(3,4-dichloro-phenoxy)-propylcarbamoyl]-ethyl}-phenyl)difluoromethylphosphonic acid Compound 20 was prepared from Compound 4 following the coupling procedure of Example 11A, with the exception that 3-(3,4-dichloro-phenoxy)-propylamine was employed as the coupling partner and 0.5M HOAt in DMF was substituted for NHS. Chromatography over silica gel using 20 to 50% EtOAc in $CH_2Cl_2$ afforded 14 mg of the intermediate compound (2S)-(4-{2-benzyloxycarbonylamino-2-[3-(3,4-dichloro-phenoxy)-propyl-carbamoyl]-ethyl}-phenyl)difluoromethylphosphonic acid diethyl ester (13%). This material was then converted into Compound 20 following the deprotection procedure of Example 11C, yielding 3 mg of product (24%). MS (ion spray):m/z 631.1 (M+H), 629.4 (M−H), 631.4 (M+2-H). $^1$H NMR: (DMSO-$d_6$, 400 MHz) δ 8.10 (dd, 1H), 7.16-7.58 (m, 12H), 6.90 (dd, 1H), 4.92 (s, 2H), 4.18-4.20 (m, 1H), 3.85 (dd, 2H), 3.18-3.35 (m, 2H), 2.94-2.98 (m, 1H), 2.78-2.82 (m, 1H), 1.75-1.79 (m, 2H).

Example 21

Synthesis of Compound 21

(4-{2-[4-(2-Methoxycarbonyl-3-hydroxy-phenoxy)butylcarbamoyl]-ethyl}-phenyl)difluoromethylphosphonic acid

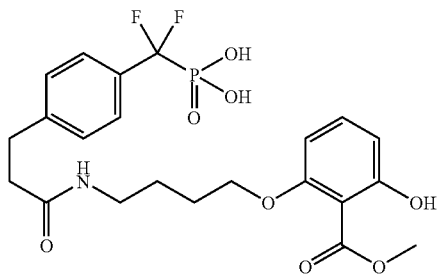

(4-{2-[4-(2-methoxycarbonyl-3-hydroxy-phenoxy)butylcarbamoyl]-ethyl}-phenyl)difluoromethylphosphonic acid
$C_{22}H_{26}F_2NO_8P$
Exact Mass: 501.14

(4-Methoxycarbonylethylphenyl)difluoromethylphosphonic acid diethyl ester was prepared from 3-(4-iodophenyl)-propionic acid methyl ester following the procedure of Example 1, yielding 53% of product. A solution of this compound (675 mg, 1.93 mmol) in 10 mL of 1:1 water:THF (v:v) was cooled to 0° C. LiOH.$H_2O$ (178 mg, 4.24 mmol) was added and the reaction stirred for 30 minutes. The reaction was quenched with aqueous $NH_4Cl$ and adjusted to pH=4 using 1M HCl. The crude product was extracted into EtOAc, dried and concentrated to 385 mg. Purification via silica chromatography (2.5% methanolic $CH_2Cl_2$) yielded 160 mg of (4-carboxyethyl-phenyl)difluoromethylphosphonic acid diethyl ester (25%). This diethyl ester was coupled to 2-(4-amino-butoxy)-6-hydroxy-benzoic acid methyl ester following the procedure of Example 11A, with the exception that dicyclohexylcarbodiimide was employed as the coupling agent. Multiple chromatographies over silica gel using methanolic $CH_2Cl_2$ afforded 157 mg of the intermediate compound (4-{2-[4-(2-methoxycarbonyl-3-hydroxyphenoxy)butylcarbamoyl]ethyl}phenyl)difluoromethyl-phosphonic acid diethyl ester (61%). The intermediate compound was then converted into Compound 21 following the procedures of Example 11C, yielding 31 mg of Compound 21 (34%). $^1$H NMR: (DMSO-$d_6$, 400 MHz) δ 9.90 (s, 1H), 7.84 (dd, 1H), 7.42 (d, 2H), 7.29 (d, 2H), 7.30 (dd, 1H), 6.45-6.48 (m, 2H), 3.90 (dd, 2H), 3.71 (s, 3H), 3.05, (dd, 2H), 2.84 (dd, 2H), 2.37 (dd, 2H), 1.50-1.62 (m, 2H), 1.40-1.50 (m, 2H).

Example 22

Synthesis of Compound 22

(2S)-(4-{2-(4-Dodecylphenylsulfonylamino)-2-[4-(2-methoxycarbonyl-3-hydroxy-phenoxy)butylcarbamoyl]-ethyl}-phenyl)difluoromethylphosphonic acid

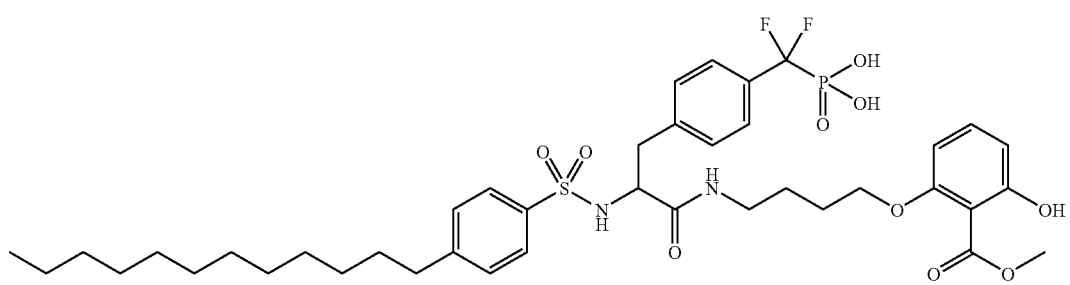

(2S)-(4-{2-(4-dodecylphenylsulfonylamino-2-[4-(2-methoxycarbonyl-3-hydroxy-phenoxy)butylcarbamoyl]-ethyl}-phenyl)difluoromethylphosphonic acid A. A solution of (2S)-(4-{2-benzyloxycarbonylamino-2-[4-(2-methoxycarbonyl-3-hydroxyphenoxy)butylcarbamoyl]ethyl}phenyl)difluoromethylphosphonic acid diethyl ester (produced in Example 8) (250 mg, 0.35 mmol) in 25 mL methanol was degassed, blanketed with nitrogen, cooled and charged with 50 mg 5% Pd on carbon. The atmosphere was exchanged with $H_2$, and the reaction stirred at 20° C. for 1 hour. The atmosphere was exchanged with nitrogen and the solution filtered over a plug of Celite®. The Celite® plug was sequentially rinsed with methanol, and the resulting solution was the concentrated to dryness in vacuo, yielding 207 mg of the free amine.

B. The free amine was dissolved in 10 mL of THF and treated with 135 mg of 4-dodecyl-benzenesulfonyl chloride and 0.35 mL of 1M $K_2CO_3$. The reaction was stirred overnight, and then quenched with aqueous ammonium chloride. After adjusting to pH=4 using 1M HCl, the product was extracted into EtOAc, dried and concentrated to 294 mg of product. Purification through multiple silica chromatographies using methanolic $CH_2Cl_2$ and EtOAc in $CH_2Cl_2$ yielded 57 mg of the diethyl phosphonate.

C. Deprotection of the phosphate esters was accomplished following the procedure of Example 11C to generate 19 mg of product. HPLC purification of this material yielded 4 mg of Compound 22 (1.4%). MS (ion spray):m/z 825.4 (M+H), 823.5 (M−H).

Example 23

Synthesis of Compound 23

(2S)-{4-[2-Phenylsulfonylamino-2-(4-phenoxybutylcarbamoyl)-ethyl]-phenyl}-difluoromethylphosphonic acid

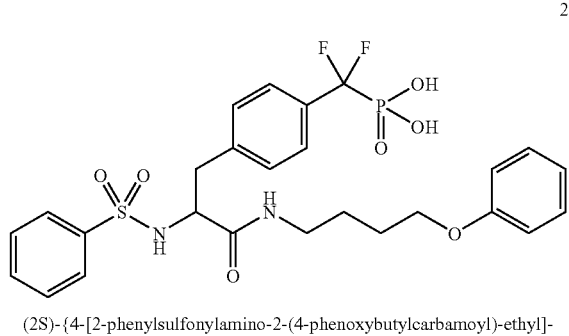

(2S)-{4-[2-phenylsulfonylamino-2-(4-phenoxybutylcarbamoyl)-ethyl]-phenyl}difluoromethylphosphonic acid The (2S)-{4-[2-benzyloxycarbonylamino-2-(4-phenoxybutylcarbamoyl)-ethyl]-phenyl}difluoromethylphosphonic acid diethyl ester produced in Example 15 was deprotected using procedure A of Example 22. The resultant amine (87 mg, 175 µmol), without further purification, was dissolved in 4 mL of $CH_2Cl_2$ and treated with 60 µL of pyridine (369 µmol) and 54 µL of benzenesulfonyl chloride (420 µmol). After stirring for 18 hours, the reaction was diluted with 20 mL of $CH_2Cl_2$ and sequentially washed with 20 mL of 1M HCl and 20 mL of water. The organic solution was dried ($Na_2SO_4$) and concentrated to 137 mg. Chromatography over silica gel using 2% methanolic $CH_2Cl_2$ yielded 78 mg of the intermediate compound (2S)-{4-[2-phenylsulfonylamino-2-(4-phenoxybutylcarbamoyl)-ethyl]-phenyl}difluoromethylphosphonic acid diethyl ester (70%). This intermediate compound was converted to Compound 23 following the procedures of Example 11C, yielding 70 mg. Further purification by HPLC yielded 2 mg of substantially purified Compound 23. MS (ion spray):m/z 583.1 (M+H), 581.2 (M−H)

$^1$H NMR: (DMSO-$d_6$, 400 MHz) δ 8.10 (d, 1H), 7.91 (dd, 1H), 7.58 (dd, 2H), 7.20-7.50 (m, 9H), 6.88-6.92 (m, 3H), 3.96 (ddd, 1H), 3.86 (dd, 2H), 2.80-2.86 (m, 3H), 2.68 (dd, 1H), 1.46-1.54 (m, 2H), 1.27-1.35 (m, 2H).

Example 24

Synthesis of Compound 24

(2S)-(4-{2-Phenylsulfonylamino-2-[4-(2-methoxycarbonyl-phenoxy)butylcarbamoyl]-ethyl}-phenyl)difluoromethylphosphonic acid

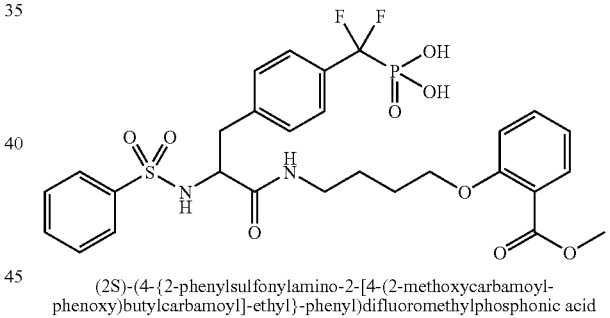

(2S)-(4-{2-phenylsulfonylamino-2-[4-(2-methoxycarbamoylphenoxy)butylcarbamoyl]-ethyl}-phenyl)difluoromethylphosphonic acid The intermediate compound (2S)-(4-{2-phenylsulfonylamino-2-[4-(2-methoxy-carbonylphenoxy)butylcarbamoyl]ethyl}phenyl)difluoromethylphosphonic acid diethyl ester was obtained from (2S)-(4-{2-benzyloxycarbonylamino-2-[4-(2-methoxycarbonyl-phenoxy)butylcarbamoyl]ethyl}phenyl)-difluoromethylphosphonic acid diethyl ester (produced in Example 17) following the procedure of Example 23, yielding 78 mg (66%). Compound 24 was prepared from this intermediate compound following the procedure of Example 11C, yielding 76 mg of product (99%). $^1$H NMR: (DMSO-$d_6$, 400 MHz) δ 7.92 (dd, 1H), 7.56-7.63 (m, 3H), 7.40-7.52 (m, 4H), 7.37 (d, 2H), 7.11 (d, 1H), 7.06 (d, 2H), 6.98 (ddd, 1H), 3.88-3.94 (3H), 3.76 (s, 3H), 2.78-2.88 (m, 3H), 2.62-2.66 (m, 1H), 1.45-1.52 (m, 2H), 1.34-1.40 (m, 2H).

Example 25

Synthesis of Compound 25

(2-Bromo-4-methylphenyl)difluoromethylphosphonic acid diethyl ester

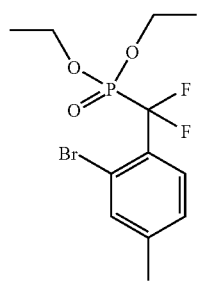

25

To a suspension of 8.5 g Cd metal (0.075 mole), in 80 mL DMF (dried over 4 Å molecular sieves for 24 hours) was added 18 g of diethyl bromodifluoro-methylphosphonate (0.068 mole) and 1 mL glacial acetic acid. Within 4 minutes an exotherm started and lasted for 20 minutes. The suspension was stirred for 3 hours and allowed to stand at room temperature for 30-40 minutes. A 40 mL aliquot of this solution was added to 6.72 g of CuCl (0.068 mole) followed after 2 minutes by the addition of 5 g of 3-bromo-4-iodotoluene (0.017 mole). The reaction suspension was stirred for 28 hours, then more cadmium reagent solution (30 mL) was added and the reaction stirred an additional 4 days. Ether (700 mL) was added and the solution was filtered through Celite®. The Celite® cake was washed with 300 mL of ether and the combined ether layer was washed with 500 mL of saturated ammonium chloride and 500 mL of water, then dried over magnesium sulfate. Filtration and solvent evaporation left behind 8.5 g of crude product. Flash chromatography on silica gel using 30% ethyl acetate/hexanes afforded 4.4 g of Compound 25.

Example 26

Synthesis of Compound 26

(2-Bromo-4-bromomethylphenyl)difluorometh-ylphosphonic acid diethyl ester

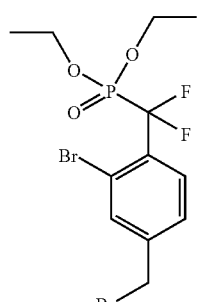

26

To 1.8 g (0.005 mole) of Compound 25 obtained from Example 25 above, in 30 mL carbon tetrachloride, were added AIBN (0.033 g, 0.0002) and N-bromosuccinimide (NBS, 0.89 g, 0.005 mole). The reaction then was heated at reflux for 2 hours. The reaction was allowed to reach room temperature and the solvent was removed under vacuum. The residue was taken up in 120 mL of ethyl acetate and washed with 60 mL of saturated NaHCO$_3$ and 60 mL of brine, then dried over MgSO$_4$. Filtration and solvent evaporation afforded 2.1 g of crude product. Flash chromatography on silica gel using 20-30% ethyl acetate/hexanes yielded 1.11 g of Compound 26. Compound 26 can be treated in a manner similar to the procedures of Example 40 to yield (2-bromo-4-bromomethylphenyl)difluoromethylphosphonic acid.

Example 27

Synthesis of Compound 27

[(2-Bromo-4-cyanomethylphenyl)difluoromethyl] phosphonic acid diethyl ester

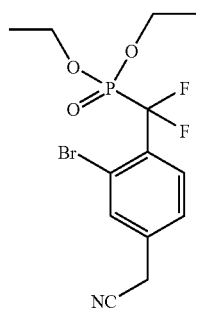

27

To Compound 26 (3.3 g, 0.0076 mole) in DCM (16 mL) were added H$_2$O (16 mL), tetrabutylammonium chloride (0.16 g) and potassium cyanide (0.98 g, 0.015 mole) and the reaction was stirred at room temperature for 4 hours. The reaction mixture was diluted with DCM (100 mL) and washed with H$_2$O (2×100 mL), 1N HCl (1×100 mL) and dried over Na$_2$SO$_4$. Flash chromatography on silica gel using 60% ethyl acetate/hexanes afforded 1.50 g of Compound 27. Compound 27 can be treated in a manner similar to the procedures of Example 40 to yield [(2-bromo-4-cyanomethylphenyl)di-fluoromethyl]-phosphonic acid.

Example 28

Synthesis of Compound 28

{[2-Bromo-4-(2-tert-butoxycarbonylaminoethyl) phenyl]difluoromethyl}phosphonic acid diethyl ester

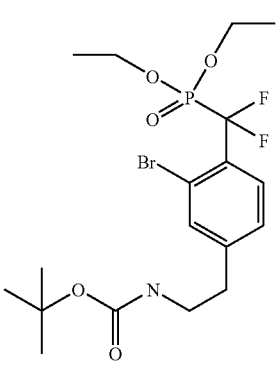

28

To 1.14 g (0.003 mole) of Compound 27 in MeOH (90 ml) at 0° C., were added 1.32 g of Boc$_2$O (0.006 mole) and CoCl$_2$.6H$_2$O (0.72 g, 0.003 mole). When all of CoCl$_2$.6H$_2$O was dissolved, 0.78 g of NaBH$_4$ (0.021 mole) was added in three portions over 15 minutes; after 40 minutes at 0° C. the solvents were evaporated. The resultant solid was taken up in EtOAc/saturated NaHCO$_3$ (120 mL each), filtered through Celite® and the EtOAc layer was separated and dried over Na$_2$SO$_4$. Flash chromatography on silica gel using 2% MeOH/CHCl$_3$ afforded 0.95 g of Compound 28.

Example 29

Synthesis of Compound 29

{[4-(2-Amino-ethyl)-2-bromophenyl]dilfluoromethyl}phosphonic acid diethyl ester hydrochloride

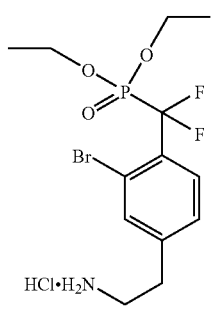

29

To 0.95 g (0.002 mole) of Compound 28 was added 16 mL of a 4N HCl solution in dioxane at room temperature and the reaction was stirred for 2 hours. The solvent was removed on the rotovap and the resultant oil was dried under high vacuum for several hours to give 0.85 g of Compound 29.

Example 30

Synthesis of Compound 30

{[2-Bromo-4-(2-benzoyloxyaminoethyl)phenyl]difluoromethyl}phosphonic acid diethyl ester

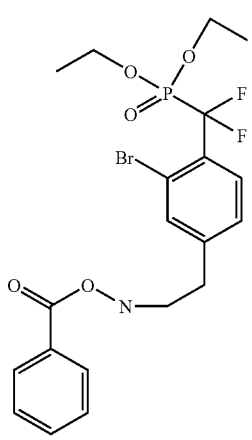

30

To 0.61 g (0.0014 mole) of Compound 29 in pH 10.5 buffer (8 mL) was added a solution of benzoyl peroxide (0.35 g, 0.0014 mole) in 8 mL of DCM in one portion and the reaction was stirred at room temperature overnight. After 21 hrs, the reaction was diluted with 35 mL of DCM and was washed with saturated NaHCO$_3$ (10 mL). The DCM layer was dried over Na$_2$SO$_4$, filtered and evaporated to give crude product (0.66 g). Flash chromatography on silica gel using 40% ethyl acetate/hexanes yielded 0.39 g of Compound 30.

Example 31

Synthesis of Compound 31

{[2-Bromo-4-(2-ethylaminoethyl)phenyl]difluoromethyl}phosphonic acid diethyl ester

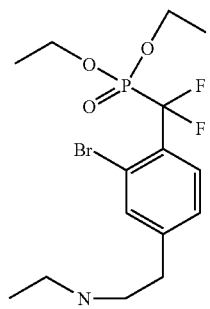

31

To 0.4 N Na$_2$CO$_3$ (1 mL) at 0° C. was added a 1 M THF solution of Et$_3$B (0.92 mL, 0.00092 mole). A solution of 0.39 g of Compound 30 (0.00077 mole) in THF (1.5 mL) was added dropwise over 2 minutes and the reaction was allowed to stir until it reached room temperature (over 1 hour) and was stirred thereafter for 4 hours. The THF was removed on the rotovap, H$_2$O (5 mL) was added and the aqueous layer was extracted with DCM (2×15 mL). The DCM layer was dried over Na$_2$SO$_4$, filtered and evaporated to yield Compound 31 (0.23 g).

Example 32

Synthesis of Compound 32

[(4-Azidomethyl-2-bromophenyl)difluoromethyl]phosphonic acid diethyl ester

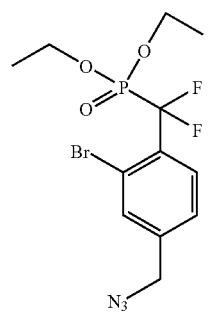

32

To 2.0 g (0.0046 mole) of Compound 26 in DMSO (10 mL) was added 0.6 g of NaN₃ (0.009 mole) at room temperature and the reaction was stirred for 60 hours. The reaction was diluted with 250 mL of ether and washed with 150 mL of water, and 150 mL of 1N HCl, dried over Na₂SO₄, filtered and evaporated to leave behind 0.55 g of the crude product. Flash chromatography on silica gel using 40% ethyl acetate/hexanes afforded 0.3 μg of Compound 32.

Example 33

Synthesis of Compound 33

Methyl-[4-(phosphonodifluoromethyl)phenyl]acetic acid diethyl ester

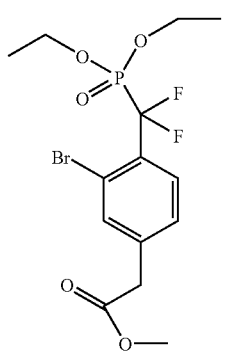

33

To 0.4 g of Compound 27 (0.0011 mole) in 0.22 mL of MeOH was added TMSCl (0.32 mL, 0.0025 mole) and the reaction flask was placed in an oil bath preheated to 47° C. and stirred for 4 hours. Water (0.05 mL) and Na₂CO₃ (0.12 g) were added and after 5 minutes the reaction was diluted with 15 mL of DCM, dried over Na₂SO₄, filtered and evaporated to leave behind 0.39 g of the crude product. Flash chromatography on silica gel using 40% ethyl acetate/hexanes afforded 0.2 g of Compound 33.

Example 34

Synthesis of Compound 34

3-Bromo-4-[(diethoxyphosphoryl)difluoromethyl) acetic acid

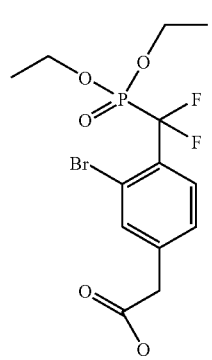

34

To 0.08 g of Compound 33 (0.00019 mole) in THF/H₂O (1.0 mL each) at 0° C. was added LiOH.H₂O (0.0085 g, 0.0002 mole) and the reaction was stirred for 100 minutes. The reaction mixture was added to a biphase of 0.2N HCl/EtOAc (20 mL each) and the EtOAc layer was separated, dried over Na₂SO₄, filtered and evaporated resulting in Compound 34.

Example 35

Synthesis of Compound 35

3-Bromo-4-[(diethoxyphosphoryl)difluoromethyl) benzoic acid

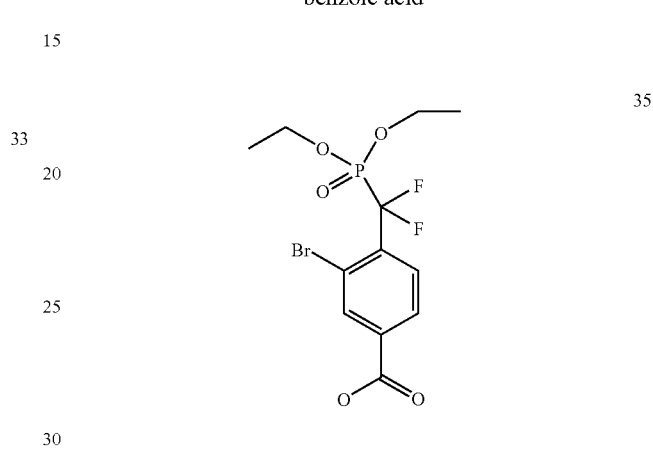

35

To 1.0 g (0.0023 mole) of Compound 26 in 10 mL of DMSO was added NaNO₂ (0.49 g, 0.0071 mole) followed by 1.3 mL of acetic acid. The reaction was stirred at room temperature for 1 hour and then at 30° C. for 1 hour. The reaction was diluted with Et₂O (120 mL) and washed with 75 mL of 1N HCl, dried over Na₂SO₄, filtered and evaporated to leave behind 11.0 g of crude product. Flash chromatography on silica gel using 4% MeOH/CHCl₃ afforded 0.15 g of Compound 35 and 0.04 g of [(2-bromo-4-hydroxymethylphenyl)difluoromethyl]phosphonic acid diethyl ester.

Example 36

Synthesis of Compound 36

{[4-(2-Benzoylaminoethyl)-2-bromophenyl]difluoromethyl}phosphonic acid diethyl ester

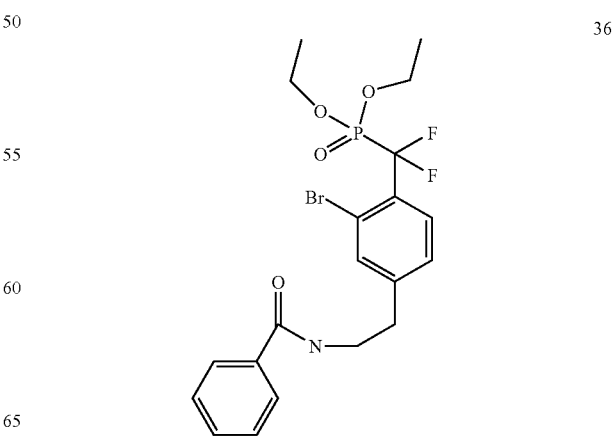

36

To Compound 29 (0.1 g, 0.00024 mole) in 1.5 mL of DCM were added DIEA (0.045 mL, 0.00026 mole), pyridine (0.021 mL, 0.00026 mole) and benzoyl chloride (0.031 mL, 0.00026 mole) and the reaction was stirred at room temperature for 5 hours. DCM (8 mL) was added and washed with 8 mL of 1N HCl, saturated NaHCO$_3$ (8 mL), 8 mL of brine, then dried over Na$_2$SO$_4$, filtered and then evaporated. Flash chromatography on silica gel using 2% MeOH/CHCl$_3$ afforded 0.083 g of Compound 36.

Alternatively, Compound 29 was dissolved in DMF (0.2M) and treated with HOBt.H$_2$O (1 equiv), carboxylic acid (1 equiv), EDC (1 equiv) and DIEA (3 equiv) and stirred at room temperature overnight. Workup is the same as in Example 39 below.

Example 37

Synthesis of Compound 37

{[4-(Benzoylaminomethyl)-2-bromophenyl]difluoromethyl}phosphonic acid diethyl ester

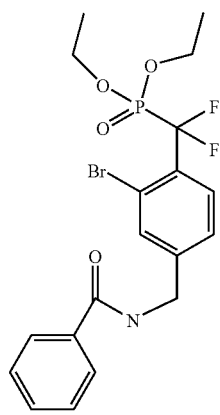

37

To Compound 32 (0.033 g, 0.000083 mole) in 1 mL of THF was added triphenylphosphine (0.023 g, 0.000084 mole) and the reaction was stirred at room temperature for 4 hours. Benzoyl chloride (0.0mL, 0.000083 mole) was added and the reaction was stirred overnight. To the resultant suspension was added 0.02 mL of H$_2$O and the reaction was stirred an additional 3.5 hours. THF was removed on the rotovap and the residue was taken up in 8 mL of EA and washed with 1N HCl (5 mL), saturated NaHCO$_3$ (5 mL), dried over Na$_2$SO$_4$, and then filtered and evaporated. Preparative TLC purification using 40% EtOAc/DCM afforded 0.014 g of Compound 37.

Example 38

Synthesis of Compound 38

[(2-Bromo-4-piperidin-1-ylmethylphenyl)difluoromethyl]phosphonic acid diethyl ester

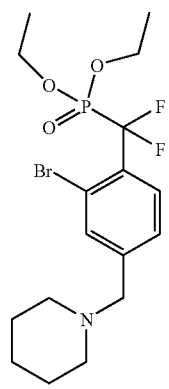

38

To 0.1 g (0.00023 mole) of Compound 26 in DMF (1.0 mL) at room temperature were added 0.04 mL of DIEA (0.00023 mole) and 0.024 mL of piperidine (0.00024 mole) and the reaction was stirred for 40 minutes. DCM (10 mL) was added and the solution was washed with saturated NaHCO$_3$ (10 mL), brine (10 mL), then dried over Na$_2$SO$_4$, and then was filtered and evaporated. Flash chromatography on silica gel using 2% MeOH/CHCl$_3$ afforded 0.078 g of Compound 38.

Example 39

Synthesis of Compound 39

{[2-Bromo-4-(phenethylcarbamoyl-methyl)phenyl]difluoromethyl}phosphonic acid diethyl ester

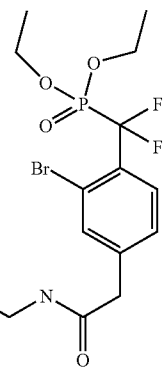

39

To 0.11 g of Compound 34 (0.00027 mole) in 2 mL of DMF at room temperature were added HOBt.H$_2$O (0.042 g, 0.00027 mole), phenethyl amine (0.035 mL, 0.00027 mole), EDC (0.053 g, 0.00027 mole) and DIEA (0.14 mL, 0.00081 mole); and the reaction was stirred for 17 hours. The reaction then was diluted with 30 mL of EtOAc and washed with 1N HCl (30 mL), saturated NaHCO$_3$ (30 mL), brine (30 mL), then dried over Na$_2$SO$_4$, and then was filtered and evaporated.

Flash chromatography on silica gel using 6% MeOH/CHCl$_3$ afforded 0.077 g of Compound 39.

Example 40

Synthesis of Compound 40

[(2-Bromo-4-methylphenyl)difluoromethyl]phosphonic acid

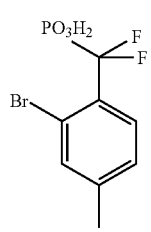

40

To 0.036 g (0.0001 mole) of Compound 25 in 0.5 mL of CH$_2$Cl$_2$ at room temperature, was added trimethylsilyl bromide (0.13 mL); and the reaction was stirred at room temperature overnight. The CH$_2$Cl$_2$ was removed and the residue was taken up in 1 mL of CH$_2$Cl$_2$ and the solvent removed again. The residue was dried under high vacuum for 40 minutes then dissolved in CH$_2$Cl$_2$ (1.0 mL) and treated with H$_2$O (1.0 mL) and the resultant reaction was stirred for 1 hour. CH$_2$Cl$_2$ was removed on the rotavap and the aqueous solution was transferred to a vial with the aid of H$_2$O/CH$_3$CN, frozen and lyophilized to give 0.030 g of Compound 40.

Example 41

Synthesis of Compound 41

[(2-Bromo-4-((2-tertbutoxycarbamoylhydrazino) methyl)phenyl)difluoromethyl]phosphonic acid diethyl ester

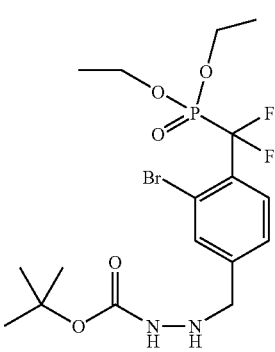

41

To Compound 26 (0.2 g, 0.00046 mole) in THF (5 mL) at room temperature was added tert-butyl carbazate (0.5 g, 0.0038 mole) and the reaction was stirred for 65 hours. The solvent was removed to give crude product. Flash chromatography on silica gel using 35% EtOAc/DCM afforded 0.2 g of pure Compound 41.

Example 42

Synthesis of Compound 42

[(2-Bromo-4-hydrazinomethylphenyl)difluoromethyl]phosphonic acid

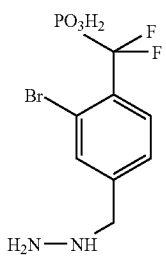

42

Compound 41 (0.05 g) was treated in a manner similar to Example 40 above to provide 0.04 g of the product Compound 42. MS (ion spray):m/z 330.95/332.92 (M+H). $^1$H NMR: (DMSO-d$_6$, 400 MHz) δ 7.72 (s, 1H) 7.59 (d, 1H, J=8.0 Hz), 7.45 (d, 1H, J=8.0 Hz), 4.02 (s, 2H).

Example 43

Synthesis of Compound 43

({2-Bromo-4-[3-(4-phenylbutyl)-1-aminoureidomethyl]phenyl}difluoromethyl)phosphonic acid

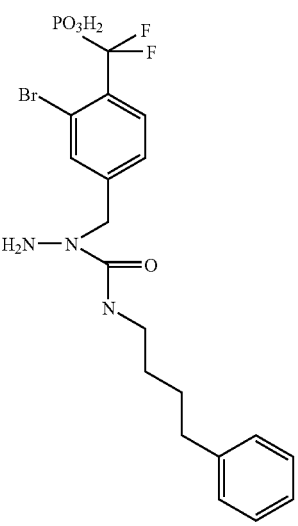

43

Compound 41 (0.21 g, 0.00043 mole) in THF (2 mL) was treated with CDI (0.07 g, 0.00043 mole) and catalytic DMAP (few crystals) and the reaction was stirred at room temperature for 24 hours. Phenbutyl amine (0.068 mL, 0.00043 mole) was added and the reaction was stirred for 20 hours. The THF was removed and the residue was taken up in 20 mL of EtOAc and washed with 1N HCl (20 mL), brine (20 mL), dried over Na₂SO₄, filtered and evaporated. Flash chromatography on silica gel using 30% EtOAc/DCM afforded 0.145 g of Boc-protected product. This product was treated in a manner similar to Example 40 to give 0.015 g of Compound 43. MS (ion spray):m/z 504.03/506.01 (M−H). ¹H NMR: (DMSO-d₆, 400 MHz) δ 7.65 (d, 1H, J=8.0 Hz) 7.52 (s, 1H), 7.26 (m, 3H), 7.17 (m, 3H), 6.94 (br s, 1H) 4.57 (s, 2H), 3.08 (m, 2H), 2.57 (m, 2H), 1.55 (m, 2H), 1.44 (m, 2H).

Example 44

Synthesis of Compound 44

[(2-Bromo-4-(benzenesulfonylhydrazonomethyl)phenyl)difluoromethyl]phosphonic acid

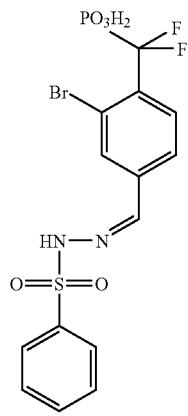

44

To 0.33 g (0.00075 mole) of Compound 26 in 3 mL of acetonitrile at room temperature was added 0.16 g (0.0009 mole) of benzenesulfonyl hydrazide and the reaction was heated at reflux for 7 hours. The solvent was removed on the rotovap and the residue dried under high vacuum. Flash chromatography on silica gel using 50% EtOAc/hexanes afforded 0.1 g of [(2-bromo-4-(benzenesulfonylhydrazonomethyl)phenyl)difluoromethyl]phosphonic acid diethyl ester. This material was treated in a manner similar to Example 40 to give 0.045 g of Compound 44. MS (ion spray):m/z 467.15/469.19 (M−H)

Example 45

Synthesis of Compound 45

[(2-Bromo-4-cyanomethylphenyl)difluoromethyl]phosphonic acid

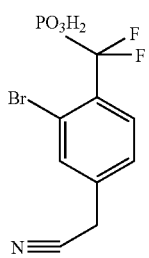

45

Compound 27 (0.026 g, 0.000068 mole) was treated in a manner similar to Example 40 above to give 0.02 g of Compound 45. MS (ion spray):m/z 325.85/326.95 (M+H), 347.89/349.93 (M+Na)

Example 46

Synthesis of Compound 46

{[4-(2-Benzenesulfonylaminoethyl)-2-bromophenyl]difluoromethyl}phosphonic acid

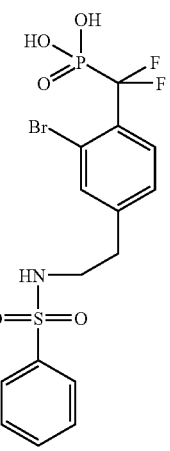

46

The free base of Compound 29 (0.08 g, 0.00021 mole) in 1 mL of DCM at room temperature was treated with 4-methylmorpholine (0.046 mL, 0.00042 mole) and benzenesulfonyl chloride (0.026 mL, 0.00021 mole) and the reaction was stirred for 6 hours. The solvent was removed and the residue was taken up in 10 mL of EtOAc and washed with 10 mL of 1N HCl dried over Na₂SO₄, filtered and evaporated. Flash chromatography on silica gel using 60% EtOAc/hexanes afforded 0.02 g of {[4-(2-benzenesulfonylaminoethyl)-2-bromophenyl]difluoromethyl}phosphonic acid diethyl ester. This intermediate was treated in a manner similar to Example 40 above to give the desired product Compound 46. MS (ion spray):m/z 468.01/469.99 (M−H)

Example 47

Synthesis of Compound 47

{[4-(2-Acetylaminoethyl)-2-bromophenyl]difluoromethyl}phosphonic acid

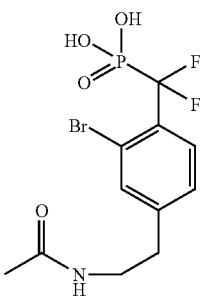

47

Compound 29 was treated as in Example 36 except that the benzoyl chloride was substituted with acetic anhydride to give the desired intermediate {[4-(2-acetylamino-ethyl)-2-bromophenyl]difluoromethyl}phosphonic acid diethyl ester. This intermediate was treated in a manner similar to Example 40 to give Compound 47. MS (ion spray):m/z 370.2/372.17 (M–H). ¹H NMR: (DMSO-d$_6$, 400 MHz) δ 7.91 (t, 1H, J=5.6 Hz) 7.55 (s, 1H), 7.52 (d, 1H, J=8.4 Hz), 7.30 (d, 1H, J=8.4 Hz), 3.25 (m, 2H), 2.7 (t, 2H, J=7.2 Hz), 1.76 (s, 3H)

Example 48

Synthesis of Compound 48

{[4-(2-Benzoylaminoethyl)-2-bromophenyl]difluoromethyl}phosphonic acid

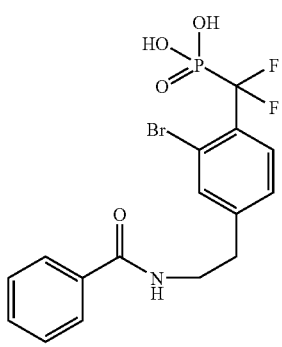

48

Compound 36 was treated in a manner similar to Example 40 to give Compound 48. MS (ion spray):m/z 432.14/434.12 (M–H). ¹H NMR: (DMSO-d$_6$, 400 MHz) δ 8.57 (t, 1H, J=5.6 Hz), 7.79 (m, 2H) 7.60 (s, 1H), 7.46 (m, 4H), 7.35 (d, 1H, J=8.4 Hz), 3.5 (m, 2H), 2.87 (t, 2H, J=7.6 Hz)

Example 49

Synthesis of Compound 49

{[2-Bromo-4-(2-phenylacetylaminoethyl)phenyl]difluoromethyl}phosphonic acid

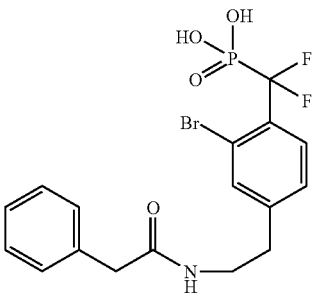

49

Compound 29 was treated in a manner similar to Example 36 except that benzoyl chloride was substituted with phenylacetyl chloride to give the intermediate {[2-bromo-4-(2-phenylacetylaminoethyl)phenyl]difluoromethyl}phosphonic acid diethyl ester which was treated in a manner similar to Example 40 above to give Compound 49. MS (ion spray):m/z 446.02/448.00 (M–H). ¹H NMR: (DMSO-d$_6$, 400 MHz) δ 8.11 (t, 1H, J=5.6 Hz), 7.55 (s, 1H) 7.50 (d, 1H, J=8.4 Hz), 7.27 (m, 3H), 7.21 (m, 3H), 3.36 (s, 2H), 3.29 (m, 2H), 2.73 (t, 2H, J=7.2 Hz)

Example 50

Synthesis of Compound 50

({2-Bromo-4-[2-(3-phenylpropionylamino)ethyl]phenyl}difluoromethyl)phosphonic acid

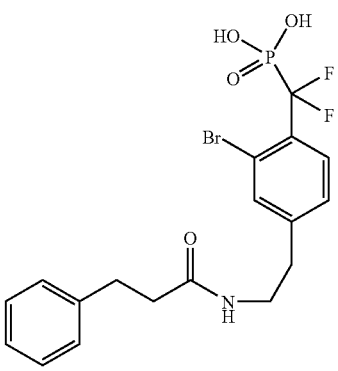

50

Compound 29 was treated in a manner similar to Example 40 except that benzoyl chloride was substituted with hydrocinnamoyl chloride to give ({2-bromo-4-[2-(3-phenylpropionylamino)ethyl]phenyl}difluoromethyl)phosphonic acid diethyl ester which was then treated in a manner similar to Example 40 above to give Compound 50. MS (ion spray):m/z 459.98/461.95 (M–H)

Example 51

Synthesis of Compound 51

({2-Bromo-4-[2-(4-phenylbutyrylamino)ethyl]phenyl}difluoromethyl)phosphonic acid

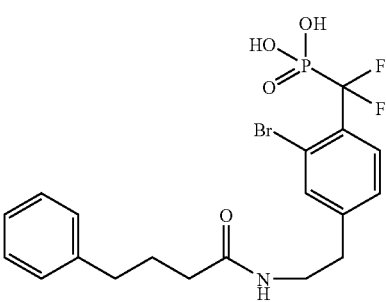

51

Compound 29 was coupled following the alternate procedure of Example 36 above, to 4-phenylbutyric acid to give ({2-bromo-4-[2-(4-phenylbutyrylamino)ethyl]phenyl}difluoromethyl)phosphonic acid diethyl ester which was treated in a manner similar to Example 40 to give Compound 51. MS (ion spray):m/z 473.94/476.04 (M–H)

Example 52

Synthesis of Compound 52

({2-Bromo-4-[2-(5-phenylpentanoylamino)ethyl]phenyl}difluoromethyl)phosphonic acid

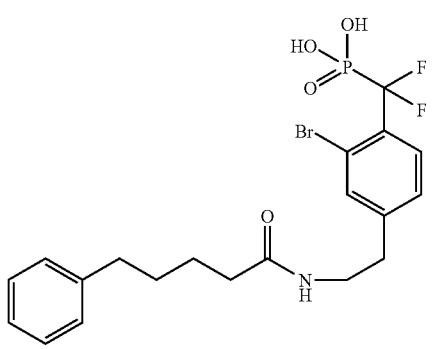

Compound 29 was coupled, following the alternate procedure of Example 36, to 5-phenylvaleric acid to give ({2-bromo-4-[2-(5-phenylpentanoylamino)ethyl]phenyl}difluoromethyl)phosphonic acid diethyl ester which was treated in a manner similar to Example 40 above to give Compound 52. MS (ion spray):m/z 488.09/490.07 (M−H). $^{1}$H NMR: (DMSO-d$_{6}$, 400 MHz) δ 7.87 (t, 1H, J=5.6 Hz), 7.53 (s, 1H) 7.51 (d, 1H, J=8.0 Hz), 7.27 (m, 3H), 7.16 (m, 3H), 3.27 (m, 2H), 2.71 (t, 2H, J=7.2 Hz), 2.54 (t, 2H, J=7.2 Hz), 2.04 (t, 2H, J=7.2 Hz), 1.48 (m, 4H)

Example 53

Synthesis of Compound 53

({2-Bromo-4-[2-(4-1H-indol-3-yl-butyrylamino)ethyl]phenyl}difluoromethyl)phosphonic acid

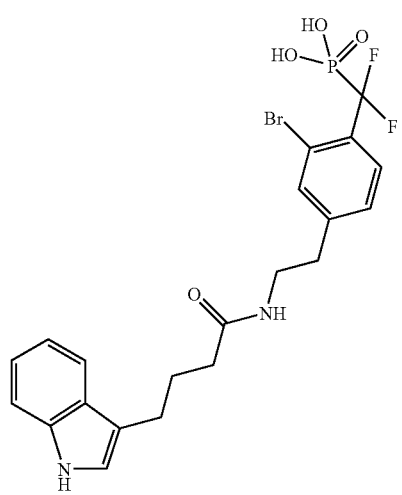

The free base of Compound 29 was coupled, following the alternate procedure of Example 36, to indole-3-butyric acid to give ({2-bromo-4-[2-(4-1H-indol-3-yl-butyrylamino)ethyl]phenyl}difluoromethyl)phosphonic acid diethyl ester which was then treated in a manner similar to Example 40 to give Compound 53. MS (ion spray):m/z 514.93/516.91 (M+H). $^{1}$H NMR: (DMSO-d$_{6}$, 400 MHz) δ 10.73 (s, 1H), 7.89 (t, 1H, J=5.6 Hz), 7.53 (m, 3H) 7.31 (d, 2H, J=8.0 Hz), 7.05 (m, 2H), 6.94 (m, 1H), 3.27 (m, 2H), 2.73 (t, 2H, J=7.2 Hz), 2.64 (t, 2H, J=7.2 Hz), 2.1 (t, 2H, J=7.2 Hz), 1.84 (m, 2H)

Example 54

Synthesis of Compound 54

[(2-Bromo-4-{2-[(2-phenylcyclopropanecarbonyl)amino]ethyl}phenyl)difluoromethyl]phosphonic acid

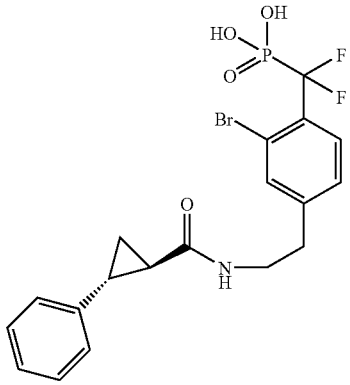

The free base of Compound 29 was coupled, following the alternate procedure of Example 36, to trans-2-phenylcyclopropane-1-carboxylic acid to give [(2-bromo-4-{2-[(2-phenylcyclopropanecarbonyl)amino]ethyl}phenyl)difluoromethyl]phosphonic acid diethyl ester which was treated in a manner similar to Example 40 to give Compound 54. MS (ion spray):m/z 472.03/474.00 (M−H)

Example 55

Synthesis of Compound 55

({4-[2-(Acetylethylamino)ethyl]-2-bromophenyl}difluoromethyl)phosphonic acid

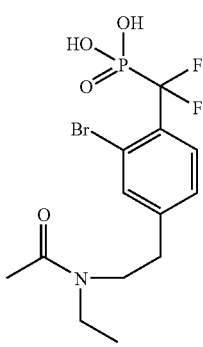

Compound 31 was treated as in Example 36 except that benzoyl chloride was substituted with acetic anhydride to give ({4-[2-(acetylethylamino)ethyl]-2-bromophenyl}difluoromethyl)phosphonic acid diethyl ester which was treated in a manner similar to Example 40 to give Compound 55. MS (ion spray):m/z 397.97/399.94 (M−H)

Example 56

Synthesis of Compound 56

({2-Bromo-4-[2-(ethyl-(2-phenylacetyl)amino)ethyl]phenyl}difluoromethyl)phosphonic acid

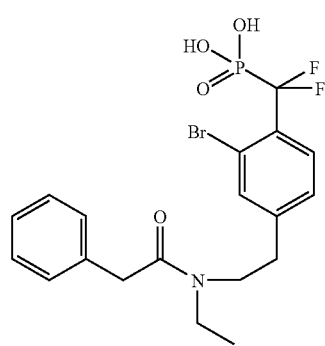

56

Compound 31 was treated as in Example 36 except that benzoyl chloride was substituted with phenylacetyl chloride to give ({2-bromo-4-[2-(ethyl-(2-phenylacetyl)amino)ethyl]phenyl}difluoromethyl)phosphonic acid diethyl ester which was treated in a manner similar to Example 40 to give Compound 56. MS (ion spray):m/z 474.21/476.18 (M−H). $^1$H NMR: (CD$_3$OD, 400 MHz) 1:1 mixture of cis and trans amide bond isomers δ 8.04 (t, 1H, J=8.4 Hz), 7.45-7.09 (m, 7H), 3.75 (s, 1H), 3.65 (s, 1H), 3.55-3.41 (m, 4H), 2.82 (t, 1H, J=7.6 Hz), 2.68 (t, 1H, J=8.0 Hz), 1.14 (t, 1.5H, J=7.2 Hz), 1.04 (t, 1.5H, J=7.2 Hz)

Example 57

Synthesis of Compound 57

[(2-Bromo-4-{2-[ethyl-(3-phenylpropionyl)amino]ethyl}phenyl)difluoromethyl]phosphonic acid

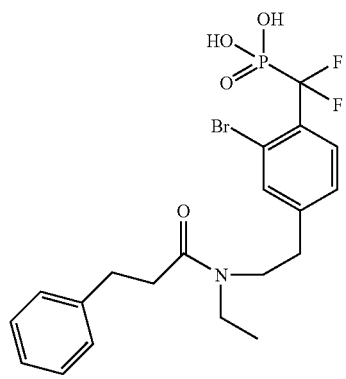

57

Compound 31 was treated in a similar manner as described in the alternate procedure of Example 36 except that benzoyl chloride was substituted with hydrocinnamic acid to give [(2-bromo-4-{2-[ethyl-(3-phenylpropionyl)amino]ethyl}phenyl)difluoromethyl]phosphonic acid diethyl ester which was treated in a manner similar to Example 40 to give Compound 57. MS (ion spray):m/z 488.03/490.00 (M−H)

Example 58

Synthesis of Compound 58

[(2-Bromo-4-{2-[ethyl-(2-phenylcyclopropanecarbonyl)amino]ethyl}phenyl)difluoromethyl]phosphonic acid

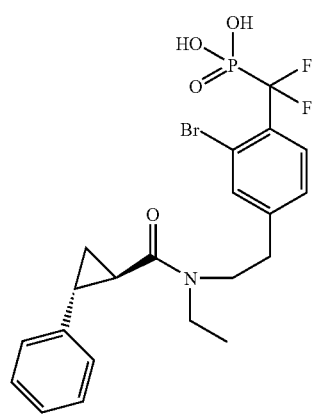

58

Compound 31 was treated in a similar manner as described in the alternate procedure of Example 36 except that benzoyl chloride was substituted with trans-2-phenylcyclopropane-1-carboxylic acid to give [(2-bromo-4-{2-[ethyl-(2-phenylcyclopropanecarbonyl)amino]ethyl}phenyl)difluoromethyl]phosphonic acid diethyl ester which was treated in a manner similar to Example 40 to give Compound 58. MS (ion spray): m/z 500.08/502.05 (M−H)

Example 59

Synthesis of Compound 59

[(2-Bromo-4-hydroxymethylphenyl)difluoromethyl]phosphonic acid

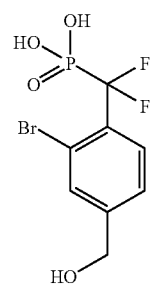

59

The diethyl ester compound [(2-bromo-4-hydroxymethylphenyl)difluoromethyl]phosphonic acid diethyl ester, obtained following Example 35, was treated in a manner similar to Example 40 to give Compound 59. MS (ion spray): m/z 315.1/317.11 (M−H). ¹H NMR: (DMSO-d₆, 400 MHz) δ 7.71 (s, 1H), 7.63 (d, 1H, J=8.8 Hz), 7.46 (d, 1H, J=8.4 Hz), 4.6 (s, 2H)

Example 60

Synthesis of Compound 60

3-Bromo-4-(phosphonodifluoromethyl)benzoic acid

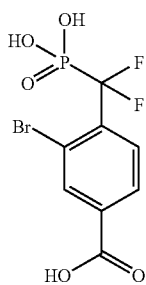

60

The carboxylic acid compound 3-bromo-4-[(diethoxyphosphoryl)difluoromethyl)benzoic acid, obtained following Example 35, was treated in a manner similar to Example 40 to give Compound 60. MS (ion spray):m/z 328.91/330.95 (M−H)

Example 61

Synthesis of Compound 61

[(2-Bromo-4-carbamoylphenyl)difluoromethyl]phosphonic acid

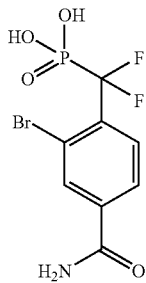

61

To 0.15 g of 3-bromo-4-[(diethoxyphosphoryl)difluoromethyl)benzoic acid obtained following Example 35, in 1.5 mL DCM at room temperature were added oxalyl chloride (0.5 mL) and 1 drop of DMF and the reaction was stirred for 90 minutes. The solvents were removed on the rotovap and the residue was taken up in 2 mL of DCM and the solvent removed. The residue was then dried under high vacuum for 1 hour, dissolved in THF (2 mL), cooled to 0° C. and ammonia gas was bubbled into the solution for 1 minute during which time a precipitate formed. After 20 minutes, the reaction was filtered and the filtrate was evaporated to leave 0.11 g of [(2-bromo-4-carbamoylphenyl)difluoromethyl]phosphonic acid diethyl ester. This compound was treated in a manner similar to Example 40 to give Compound 61. MS (ion spray): m/z 328.00/330.04 (M−H)

Example 62

Synthesis of Compound 62

{[2-Bromo-4-(4-phenylbutylcarbamoyl)phenyl]difluoromethyl}phosphonic acid

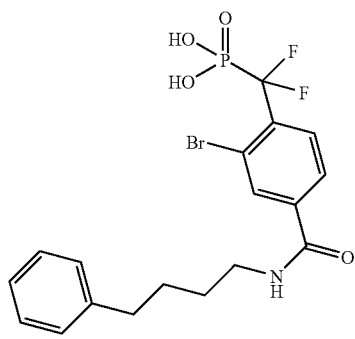

62

The 3-bromo-4-[(diethoxyphosphoryl)difluoromethyl) benzoic acid (Compound 35) was coupled to phenbutyl amine following the procedures of Example 39 to give {[2-bromo-4-(4-phenylbutylcarbamoyl)phenyl]difluoromethyl}-phosphonic acid diethyl ester which was treated in a manner similar to Example 40 to give Compound 62. MS (ion spray): m/z 459.98/461.95 (M−H)

Example 63

Synthesis of Compound 63

[3-Bromo-4-(phosphonodifluoromethyl)phenyl]acetic acid methyl ester

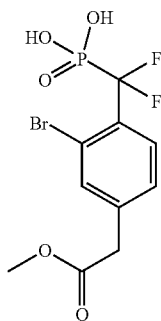

63

Compound 33 was treated in a manner similar to Example 40 to give Compound 63. MS (ion spray):m/z 357.07/359.04 (M–H)

Example 64
Synthesis of Compound 64

[3-Bromo-4-(phosphonodifluoromethyl)phenyl]acetic acid

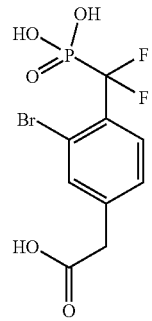
64

Compound 34 was treated in a manner similar to Example 40 to give Compound 64. MS (ion spray):m/z 343.01/345.02 (M–H)

Example 65
Synthesis of Compound 65

{[2-Bromo-4-(phenethylcarbamoylmethyl)phenyl]difluoromethyl}phosphonic acid

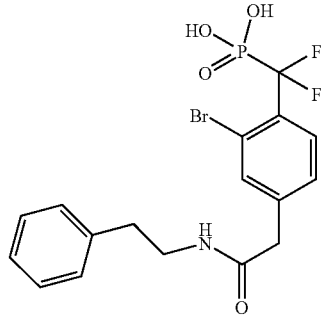
65

Compound 39 was treated in a manner similar to Example 40 to give Compound 65. MS (ion spray):m/z 446.16/448.14 (M–H). $^1$H NMR: (DMSO-$d_6$, 400 MHz) δ 8.19 (t, 1H, J=5.6 Hz), 7.58 (s, 1H), 7.51 (d, 1H, J=8.0 Hz), 7.27 (m, 3H), 7.17 (m, 3H), 3.42 (s, 2H), 3.27 (m, 2H), 2.70 (t, 2H, J=7.2 Hz)

Example 66
Synthesis of Compound 66

{[4-(Benzoylaminomethyl)2bromophenyl]difluoromethyl}phosphonic acid

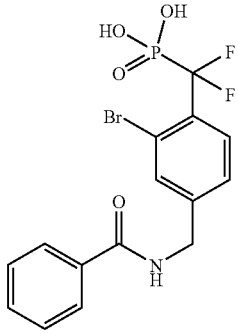
66

Compound 37 was treated in a manner similar to Example 40 to give Compound 66. MS (ion spray):m/z 418.12/420.10 (M–H)

Example 67
Synthesis of Compound 67

{[4-(Acetylamino-methyl)-2-bromophenyl]difluoromethyl}phosphonic acid

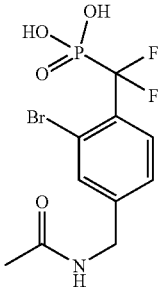
67

Compound 32 was treated in a manner similar to Example 37 except that benzoyl chloride was substituted with acetic anhydride to give {[4-(acetylaminomethyl)-2-bromophenyl]difluoromethyl}phosphonic acid diethyl ester which was then treated in a manner similar to Example 40 to give Compound 67. MS (ion spray):m/z 356.12/358.09 (M–H)

Example 68
Synthesis of Compound 68

{[4-(2-Aminoethyl)-2-bromophenyl]difluoromethyl}phosphonic acid

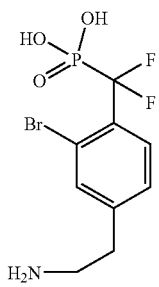
68

Compound 29 was treated in a manner similar to Example 40 to give Compound 68. MS (ion spray):m/z 328.02/329.99 (M–H)

Example 69
Synthesis of Compound 69

{[2-Bromo-4-(2-ethylaminoethyl)phenyl]difluoromethyl}phosphonic acid

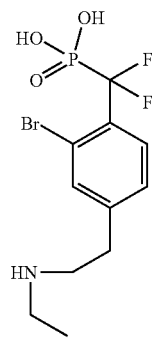
69

Compound 31 was treated in a manner similar to Example 40 to give Compound 69. MS (ion spray):m/z 355.98/357.96 (M–H)

Example 70

Synthesis of Compound 70

[(4-Azidomethyl-2-bromophenyl)difluoromethyl]phosphonic acid

70

Compound 32 was treated in a manner similar to Example 40 to give Compound 70. MS (ion spray):m/z 340.05/342.09 (M–H)

Example 71

Synthesis of Compound 71

[(2-Bromo-4-ethylaminomethylphenyl)difluoromethyl]phosphonic acid hydrobromide

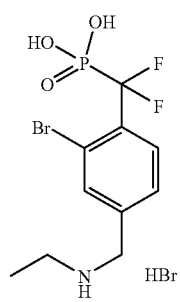

71

Compound 26 was reacted with ethyl amine in a manner similar to Example 38 except no base was used and THF was used instead of DMF to give [(2-bromo-4-ethylaminomethylphenyl)difluoromethyl]phosphonic acid diethyl ester which was then treated in a manner similar to Example 40 to give Compound 71. MS (ion spray):m/z 341.93/343.94 (M–H). $^1$H NMR: (DMSO-d6, 400 MHz) δ 8.82 (br s, 2H), 7.85 (s, 1H), 7.64 (d, 1H, J=8.4 Hz), 7.56 (d, 1H, J=8.4 Hz), 4.15 (m, 2H), 2.97 (m, 2H), 1.19 (t, 3H, J=7.6 Hz)

Example 72

Synthesis of Compound 72

[(2-Bromo-4-dimethylaminomethylphenyl)difluoromethyl]phosphonic acid hydro-bromide

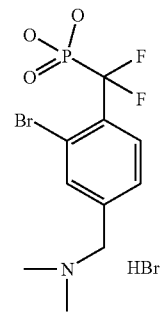

72

Compound 26 was reacted with dimethyl amine in a manner similar to Example 38 to give [(2-bromo-4-dimethylaminomethylphenyl)difluoromethyl]phosphonic acid diethyl ester which was then treated in a manner similar to Example 40 to give Compound 72. MS (ion spray):m/z 342.30/344.28 (M–H). $^1$H NMR: (DMSO-d6, 400 MHz) δ 10.2 (br s, 1H), 7.86 (s, 1H), 7.68 (d, 1H, J=8.0 Hz), 7.56 (d, 1H, J=8.0 Hz), 4.27 (s, 2H), 2.68 (s, 6H)

Example 73

Synthesis of Compound 73

[(2-Bromo-4-diethylaminomethylphenyl)difluoromethyl]phosphonic acid hydrobromide

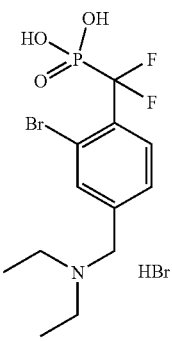

73

Compound 26 was reacted with diethyl amine in a manner similar to Example 38 except no base was used and THF was used instead of DMF to give [(2-bromo-4-diethylaminomethylphenyl)difluoromethyl]phosphonic acid diethyl ester which was then treated in a manner similar to Example 40 to give Compound 73. MS (ion spray):m/z 370.00/371.97

(M–H). ¹H NMR: (CD₃OD, 400 MHz) δ 7.87 (s, 1H), 7.78 (d, 1H, J=8.4 Hz), 7.55 (d, 1H, J=8.4 Hz), 4.34 (s, 2H), 3.22 (m, 4H), 1.35 (t, 6H, J=7.6 Hz)

Example 74

Synthesis of Compound 74

[(4-Azetidin-1-ylmethyl-2-bromophenyl)difluoromethyl]phosphonic acid hydrobromide

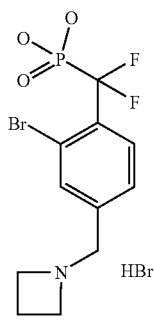

Compound 26 was reacted with azetidine hydrochloride in a manner similar to Example 38 to give [(4-azetidin-1-ylmethyl-2-bromophenyl)difluoromethyl]phosphonic acid diethyl ester which was then treated in a manner similar to Example 40 to give Compound 74. MS (ion spray):m/z 354.11/356.09 (M–H). ¹H NMR: (DMSO-d6, 400 MHz) δ 10.08 (br s, 1H), 7.85 (s, 1H), 7.65 (d, 1H, J=8.0 Hz), 7.57 (d, 1H, J=8.0 Hz), 4.40 (d, 2H, J=6.4 Hz), 4.04 (m, 4H), 2.37 (m, 2H)

Example 75

Synthesis of Compound 75

[(2-Bromo-4-pyrrolidin-1-ylmethylphenyl)difluoromethyl]phosphonic acid hydro-bromide

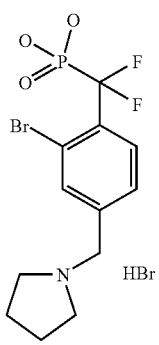

Compound 26 was reacted with pyrrolidine in a manner similar to Example 38 to give [(2-bromo-4-pyrrolidin-1-ylmethylphenyl)difluoromethyl]phosphonic acid diethyl ester which was then treated in a manner similar to Example 40 above to give Compound 75. MS (ion spray):m/z 368.23/370.21 (M–H) ¹H NMR: (DMSO-d6, 400 MHz) δ 9.97 (br s, 1H), 7.92 (s, 1H), 7.67 (d, 1H, J=8.0 Hz), 7.62 (d, 1H, J=8.0 Hz), 4.38 (d, 2H, J=5.2 Hz), 3.37 (m, 2H), 3.08 (m, 2H), 2.02 (m, 2H), 1.84 (m, 2H)

Example 76

Synthesis of Compound 76

{[2-Bromo-4-(2,5-dihydro-pyrrol-1-ylmethyl)phenyl]difluoromethyl}phosphonic acid hydrobromide

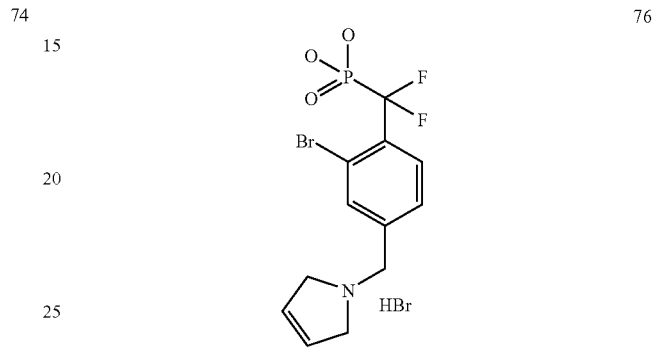

Compound 26 was reacted with pyrroline in a manner similar to Example 38 to give {[2-bromo-4-(2,5-dihydropyrrol-1-ylmethyl)phenyl]difluoromethyl}phosphonic acid diethyl ester which was treated in a manner similar to Example 40 to give Compound 76.

MS (ion spray):m/z 366.23/368.21 (M–H) ¹H NMR: (DMSO-d6, 400 MHz) δ 11.5 (br s, 1H), 7.90 (s, 1H), 7.66 (m, 2H), 5.89 (s, 2H), 4.43 (s, 2H), 3.98 (m, 4H)

Example 77

Synthesis of Compound 77

[(2-Bromo-4-piperidin-1-ylmethylphenyl)difluoromethyl]phosphonic acid hydrobromide

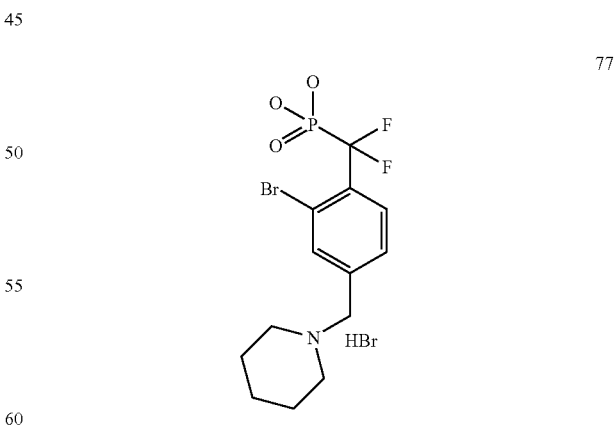

Compound 38 was treated in a manner similar to Example 40 to give Compound 77. MS (ion spray):m/z 382.21/384.21 (M–H). ¹H NMR: (DMSO-d6, 400 MHz) δ 9.70 (br s, 1H), 7.88 (s, 1H), 7.68 (d, 1H, J=8.0 Hz), 7.59 (d, 1H, J=8.0 Hz), 4.28 (s, 2H), 3.28 (m, 2H), 2.85 (m, 2H), 1.77 (m, 2H), 1.64 (m, 3H), 1.36 (m, 1H)

Example 78

Synthesis of Compound 78

[(2-Bromo-4-morpholin-4-ylmethyl-phenyl)difluoromethyl]phosphonic acid hydro-bromide

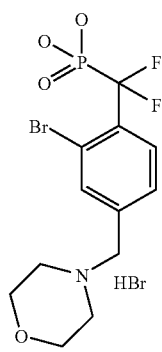

Compound 26 was reacted with morpholine following procedures substantially similar to Example 38 to give [(2-bromo-4-morpholin-4-ylmethylphenyl)difluoromethyl] phosphonic acid diethyl ester which was then treated in a manner similar to Example 40 to give Compound 78. MS (ion spray):m/z 384.21/386.30 (M−H). $^1$H NMR: (DMSO-d6, 400 MHz) δ 10.30 (br s, 1H), 7.88 (s, 1H), 7.68 (d, 1H, J=8.0 Hz), 7.59 (d, 1H, J=8.0 Hz), 4.33 (s, 2H), 4.00-3.60 (br m, 4H), 3.14 (br m, 4H)

Example 79

Synthesis of Compound 79

{[2-Bromo-4-(4-methyl-piperazin-1-ylmethyl)phenyl]difluoromethyl}phosphonic acid bishydrobromide

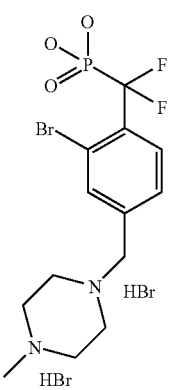

Compound 26 was reacted with 4-methylpiperazine following the procedures of Example 38 to give {[2-bromo-4-(4-methyl-piperazin-1-ylmethyl)phenyl]difluoromethyl}phosphonic acid diethyl ester which was then treated in a manner similar to Example 40 to give Compound 79. MS (ion spray):m/z 397.28/399.28 (M−H). $^1$H NMR: (D20, 400 MHz) δ 7.70 (s, 1H), 7.58 (d, 1H, J=8.0 Hz), 7.42 (d, 1H, J=8.0 Hz), 4.22 (s, 2H), 3.41 (br m, 8H), 2.85 (s, 3H)

Example 80

Synthesis of Compound 80

[(1-Bromo-naphthalen-2-yl)difluoromethyl]phosphonic acid

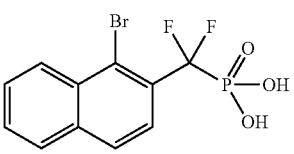

A. To a solution of 1-bromo-2-naphthaldehyde (0.740 g, 0.001 mole) in tetrahydrofuran (10 mL) was added triethylamine (0.150 mL, 0.001 mole) followed by diethylphosphite (0.330 mL, 0.002 mole). The reaction mixture was then stirred at room temperature under nitrogen gas for 18 hours. The volatiles then evaporated in vacuo and further dried under vacuum. The resulting solid was triturated with ether and the solid that separated out was collected and dried under vacuum to get 0.935 g of [(1-bromonaphthalene-2-yl)-hydroxymethyl]phosphonic acid diethyl ester B. This material was added to 40 mL of acetone. 20 eq. of manganese dioxide (4.31 g, 0.05 moles) was added and the mixture was stirred at room temperature for one hour. Another 20 eq. of manganese dioxide was added to it and it was stirred for another one hour. The solid manganese dioxide was filtered off on a Celite® pad and washed with hot acetone. Combined filtrates were evaporated to afford 0.6 g of crude (1-bromo-naphthalene-2-carbony)phosphonic acid diethyl ester. Flash chromatography on silica gel using 0-5% ethyl acetate/dichloromethane followed by drying of the product under high vacuum afforded 0.260 g of intermediate.

C. To a solution of diethyl (1-bromonaphthalene-2-carbony) phosphonate ester in dichloromethane (2 mL) was added (diethylamino)sulfur trifluoride (1.3 mL, 0.01 mole) at 0° C. and it was allowed to come to room temperature then stirred for another 4 hours. The reaction mixture then was diluted with dichloromethane (50 mL) and washed with cold saturated aqueous sodium bicarbonate (NaHCO$_3$, 25 mL), then dried over magnesium sulfate (MgSO$_4$). Filtration and solvent evaporation provided 0.260 g of product. Flash chromatography on silica gel using 0-5% EtOAc/dichloromethane followed by drying of the product under high vacuum afforded 0.120 g of diethyl [(1-bromo-naphthalene-2-yl)difluoromethylphosphonate ester. Compound 80 was prepared from this corresponding diethyl ester using procedures similar to those of Example 40. $^1$H NMR: (DMSO-d$_6$, 400 MHz) δ 8.52 (d, 1H, J=8.4 Hz) 8.11 (m, 2H), 7.79 (m, 3H). MS (ion spray): m/z 337.00 (M+H)

Example 81

Synthesis of Compound 81

(6-Bromo-benzo[1,3]dioxol-5-yl)difluoromethylphosphonic acid

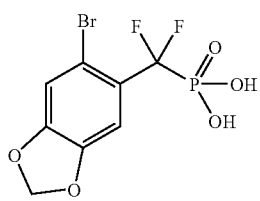

81

The intermediate [(6-bromo-benzo[1,3]dioxol-5-yl)hydroxymethyl]phosphonic acid diethyl ester was prepared from 6-bromo-benzo[1,3]dioxol-5-carbaldehyde following a procedure similar to Example 80A. The intermediate [(6-bromo-benzo[1,3]dioxol-5-yl)hydroxymethyl]phosphonic acid diethyl ester was used to prepare [(6-Bromo-benzo[1,3]dioxol-5-carbonyl)phosphonic acid diethyl ester following a procedure similar to Example 80B except pyridinium chlorochromate was used as an oxidizing agent. This resultant material was used to prepare [(6-bromo-benzo[1,3]dioxol-5-yl)difluoromethylphosphonic acid diethyl ester following a procedure similar to Example 80C. Compound 81 was prepared from the (6-bromo-benzo[1,3]dioxol-5-yl)difluoromethylphosphonic acid diethyl ester following a procedure similar to Example 40. $^1$H NMR: (DMSO-$d_6$, 400 MHz) δ 7.13 (s, 1H), 7.7 (s, 1H), 6.05 (d, 1H, J=2.0 Hz). MS (ion spray): m/z 330.17 (M–H)

Example 82

Synthesis of Compound 82

(2-Bromo-5-methylphenyl)difluoromethylphosphonic acid

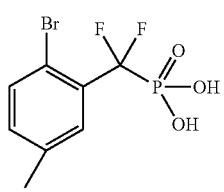

82

A. To a suspension of 2-bromo-5-methyl benzoic acid (1.0 g, 0.00465 mole) in dry dichloromethane (10 mL) was added oxalylchloride (1.22 mL, 0.013 mole) dropwise at 0° C. followed by 1-2 drops of N,N-dimethyl formamide. The reaction mixture was then stirred for 2 hours at room temperature and the solvents were evaporated and the product dried under vacuum to yield 2-bromo-5-methylbenzoyl chloride which was used for the next step. To a precooled solution of 2-bromo-5-methyl benzoyl chloride in toluene (5 mL) was slowly added a pre-cooled solution of triethylphosphite (1.05 mL, 0.00604 mole) in toluene. The reaction was then left at room temperature for overnight. The solvents were then evaporated on a rotovap. The resultant product was diluted with dichloromethane (50 mL), washed with saturated sodium bicarbonate (NaHCO$_3$, 25 mL), and then dried over magnesium sulfate (MgSO$_4$). Filtration and solvent evaporation provided 1.1 g of product. Flash chromatography on silica gel using 0%-5% ethyl acetate/dichloromethane followed by drying of the product under high vacuum afforded 0.900 g of (2-bromo-5-methylbenzoyl)phosphonic acid diethyl ester.

B. The material from A above was used to prepare [2-bromo-5-methylbenzoyl)difluoromethyl]phosphonic acid diethyl ester following a procedure similar to Example 80C. This material was used to prepare Compound 82 following a procedure similar to Example 40. $^1$H NMR: (DMSO-$d_6$, 400 MHz) δ 7.56 (d, 1H, J=8.4 Hz), 7.40 (s, 1H), 7.19 (d, 1H, J=8.0 Hz), 2.28 (s, 3H). MS (ion spray): m/z 300.15/301.05 (M–H)

Example 83

Synthesis of Compound 83

(2-Bromo-5-hydroxyphenyl)difluoromethylphosphonic acid

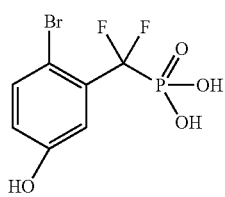

83

(2-Bromo-5-methoxybenzoyl)phosphonic acid diethyl ester was prepared following a procedure similar to Example 82A except that 2-bromo-5-methoxybenzoyl chloride was used instead of 2-bromo-5-methylbenzoylchloride. This product was subjected to conditions similar to those of Example 82C to yield (2-bromo-5-methoxyphenyl)difluoromethylphosphonic acid diethyl ester. To a solution of (2-bromo-5-methoxyphenyl)dilfluoromethylphosphonic acid diethyl ester (0.170 g, 0.0005 moles) in dichloromethane (1 mL) was added boron tribromide (0.175 mL, 0.0009 moles) at 0° C. and it was allowed to come to room temperature, then stirred for 3 hours at room temperature. It was then diluted with dichloromethane (50 mL), washed with cold water, then dried over magnesium sulfate (MgSO$_4$). Filtration and solvent evaporation provided 0.130 g of (2-bromo-5-hydroxyphenyl)dilfluoromethyl-phosphonic acid diethyl ester. This material was used to prepare Compound 83 following a procedure similar to Example 40. $^1$H NMR:

(DMSO-d$_6$, 400 MHz) δ 10.03 (s, 1H, OH), 7.42 (d, 1H, J=8.8 Hz), 7.07 (bs, 1H), 6.76 (m, 1H). MS (ion spray): m/z

Example 84

Synthesis of Compound 84

[(4-Bromo-biphenyl-3-yl)difluoromethyl]phosphonic acid

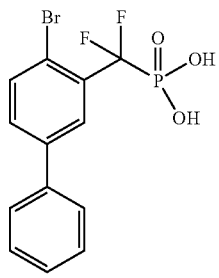

To a solution of the diethyl ester of Compound 83 (0.130 g, 0.000362 moles) in dichloromethane (3 mL) was added pyridine (0.0148 mL, 0.00180 mole) followed by trifluoromethanesulfonic anhydride (0.070 mL, 0.000416 mole) at 0° C. The reaction then was stirred for one hour at 0° C. It was then diluted with dichloromethane (50 mL), washed with water, 0.5N aqueous sodium hydroxide, 10% aqueous citric acid, then dried over magnesium sulfate (MgSO$_4$). Filtration and solvent evaporation provided 0.150 g of crude product. Flash chromatography on silica gel using dichloromethane followed by drying of the product under high vacuum afforded 0.120 g of trifluoromethane sulfonic acid-4-bromo-3-[diethoxyphosphoryl]dilfluoromethylphenyl ester. To a solution of this material in toluene (1 mL) was added phenylboronic acid (0.055 g, 0.000448 mole), tetrakistriphenylphosphinepalladium(0) (3 mole %) and anhydrous potassium carbonate (0.046 g, 0.000336 mole). The reaction temperature then was raised to and maintained at 90° C. for next 3 hours. It was then diluted with ethylacetate (50 mL), washed with saturated sodium bicarbonate (NaHCO$_3$), saturated sodium chloride solution and dried over magnesium sulfate (MgSO$_4$). Filtration and solvent evaporation provided 0.100 g of crude product. Flash chromatography on silica gel using 0%-1% ethylacetate/dichloromethane followed by drying of the product under high vacuum afforded 0.015 g of [(4-bromo-biphenyl-3-yl)difluoromethyl]phosphonic acid diethyl ester. Compound 84 was prepared from the [(4-bromo-biphenyl-3-yl)difluoromethyl]phosphonic acid diethyl ester following a procedure similar to Example 40. $^1$H NMR: (CD$_3$OD, 400 MHz) δ 7.79 (m, 1H), 7.68 (d, 1H, J=8.4 Hz), 7.52 (m, 3H), 7.36 (m, 3H).

MS (ion spray): m/z 363.12 (M–H).

Example 85

Synthesis of Compound 85

[(2-Bromo-5-bromomethylphenyl)difluoromethyl] phosphonic acid

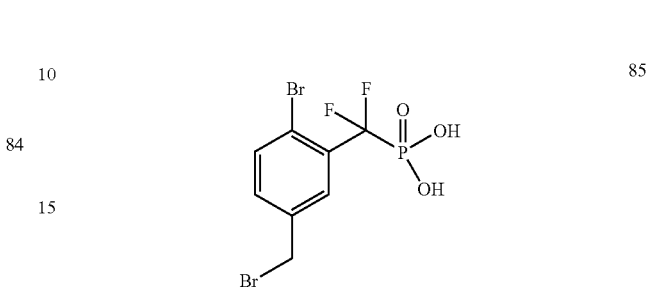

To a biphasic mixture of (2-bromo-5-methylbenzoyl)phosphonic acid diethyl ester (0.080 mL, 0.00147 mole) followed by 35% aqueous hydrogen peroxide (1.5 mL, 0.00158 mole). The reaction mixture was then stirred at room temperature overnight. It was then diluted with dichlormethane, washed with saturated sodium bicarbonate (NaHCO$_3$), water, and then dried over magnesium sulfate (MgSO$_4$). Filtration and solvent evaporation provided product. Flash chromatography on silica gel using 0%-1% ethylacetate/dichloromethane followed by drying under high vacuum afforded 0.180 g of [(2-bromo-5-bromomethylphenyl)difluoromethyl]phosphonic acid diethyl ester. Compound 85 was prepared from this corresponding diethyl ester following a procedure similar to Example 40. $^1$H NMR: (CD$_3$OD, 400 MHz) δ 7.44 (m, 2H), 7.18 (d, 1H, J=8.4 Hz), 4.32 (s, 2H). MS (ion spray): m/z 381.09 (M+H).

Example 86

Synthesis of Compound 86

[(2-Bromo-4-trifluoromethyl-phenyl)difluoromethyl] phosphonic acid

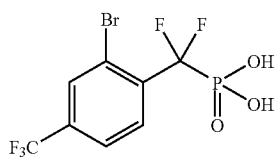

Commercially available 2-bromo-4-(trifluoromethyl)benzeneamine (2.06 g, 8.6 mmol) was suspended in concentrated HCl (4.0 mL). Clumps of material were broken up with a spatula, then ice (~2.6 g) was added to the mixture and it was cooled over an ice bath. A solution of NaNO$_2$ (0.64 g, 9.3 mmol) in H$_2$O (2.6 mL) was added dropwise while maintaining the temperature of the reaction mixture at 0-5° C. The mixture was stirred for 20 minutes over the ice bath, then poured slowly into a solution of KI (12.5 g, 75.3 mmol) in H$_2$O (16 mL). The KI mixture was stirred for several minutes, then left to settle over night. The reaction mixture was extracted thrice with hexanes. The combined organics were washed twice with 1M NaOH, once with aqueous sodium bisulfite solution, then with brine. The solution was dried over MgSO₄, vacuum filtered through Celite® and conc in vacuo to give 2.33 g of 2-bromo-4-(trifluoromethyl)-iodobenzene. By TLC (100% hexanes) and ¹H NMR analysis, it was determined that the product was of sufficient purity to be used in the subsequent step. The resultant diethyl [2-bromo-4-(trifluoromethyl)-phenyl]difluoromethylphosphonate was synthesized from 2-bromo-4-(trifluoromethyl)-iodobenzene according to Example 25 except that chlorotrimethylsilane (several drops) was used in place of acetic acid. Compound 86 was synthesized according to procedures similar to those of Example 40 from this corresponding diethyl phosphonate. MS (ES–):m/z 352.9, 354.9 (M–H). ¹H NMR: (DMSO-d₆, 400 MHz) δ 8.07 (s, 1H), 7.89 (d, J=8.0, 1H), 7.78 (d, J=8.0, 1H).

Example 87

Synthesis of Compound 87

[2-Bromo-5-(trifluoromethyl)phenyl]difluoromethylphosphonic acid

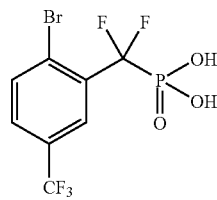

2-Bromo-5-(trifluoromethyl)-iodobenzene was synthesized from 2-bromo-5-(trifluoromethyl)benzeneamine according to the procedure described for Example 86. Diethyl [2-bromo-5-(trifluoromethyl)phenyl]difluoromethylphosphonate was synthesized from 2-bromo-5-(trifluoromethyl)-iodobenzene according to Example 25 except that chlorotrimethylsilane (several drops) was used in place of acetic acid. Compound 87 was synthesized according to procedures similar to those of Example 40 from this corresponding diethyl phosphonate. MS (ES–): m/z 353.0, 355.0 (M–H). ¹H NMR: (DMSO-d₆, 400 MHz) δ 7.94 (d, J=8.2, 1H), 7.90 (s, 1H), 7.68 (d, J=8.2, 1H).

Example 88

Synthesis of Compound 88

(2-Fluoro-4-methylphenyl)difluoromethylphosphonic acid

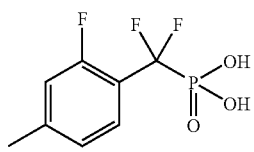

2-Fluoro-1-iodo-4-methylbenzene was synthesized from 2-fluoro-4-methylaniline compound according to the procedure described for Example 86. Purification of the iodobenzene compound was performed by chromatography (0-2% EtOAc-hexanes). Diethyl (2-fluoro-4-methylphenyl)difluoromethylphosphonate was synthesized from 2-fluoro-1-iodo-4-methylbenzene according to Example 25 except that chloro-trimethylsilane (several drops) was used in place of acetic acid. Compound 98 was synthesized according to procedures similar to those of Example 40 from the corresponding diethyl phosphonate. MS (ES–): m/z 239.1 (M–H). ¹H NMR: (DMSO-d₆, 400 MHz) δ 7.33-7.37 (m, 1H), 7.08-7.11 (m, 2H), 2.33 (s, 3H).

Example 89

Preparation of Compound 89

Sodium (2-bromo-4-chlorophenyl)difluoromethyl phosphonate

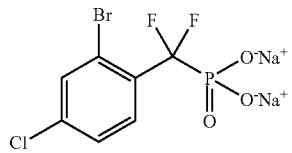

Diethyl (2-bromo-4-chlorophenyl)difluoromethylphosphonate was synthesized from commercially available 2-bromo-4-chloroiodobenzene according to Example 25 except that chlorotrimethylsilane (several drops) was used in place of acetic acid. Compound 89 was synthesized according to procedures similar to those of Example 40 from the corresponding diethyl phosphonate. The disodium salt was prepared from the phosphonic acid and NaHCO₃. MS (ES–): m/z 319.0, 321.1 (M–H). ¹H NMR: (CD₃OD, 400 MHz) δ 8.09 (d, J=8.6, 1H), 7.60 (d, J=2.3, 1H), 7.30-7.32 (m, 1H).

Example 90

Synthesis of Compound 90

(3-Bromonaphthalen-2-yl)difluoromethylphosphonic acid

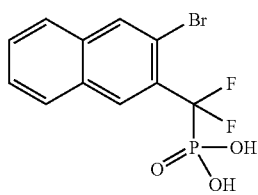

Diethyl (3-bromonaphthalen-2-yl) difluoromethylphosphonate was synthesized from commercially available 2-bromo-3-iodonaphthalene according to Example 25 except that chlorotrimethylsilane (several drops) was used in place of acetic acid. Compound 90 was synthesized according to procedures similar to those of Example 40 from this corresponding diethyl phosphonate. MS (ES–): m/z 335.0, 337.0

(M–H). $^1$H NMR: (CD$_3$OD, 400 MHz) δ 8.25 (s, 2H), 7.95 (dd, J=1.6, 7.8, 1H), 7.85 (dd, J=2.0, 8.0, 1H), 7.56-7.63 (m, 2H).

Example 91

Synthesis of Compound 91

[2-Bromo-(4-dibromomethyl)phenyl]difluoromethylphosphonic acid

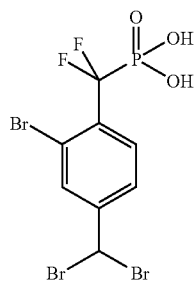

Diethyl (2-bromo-4-methylphenyl)difluoromethylphosphonate was brominated according to Example 26. Repeated chromatography with EtOAc-hexanes afforded substantially pure diethyl [2-bromo-(4-dibromomethyl)phenyl]difluoromethyl-phosphonate along with the mono-brominated product. Compound 91 was synthesized according to procedures similar to those of Example 40 from this corresponding diethyl phosphonate. MS (ES–): m/z 456.7, 458.6 (M–H). $^1$H NMR: (DMSO-d$_6$, 400 MHz) δ 7.89 (d, J=1.6, 1H), 7.76 (dd, J=1.6, 8.2, 1H), 7.65 (d, J=8.2, 1H), 7.38 (s, 1H).

Example 92

Synthesis of Compound 92

(2-Bromo-5-methoxyphenyl)difluoromethylphosphonic acid

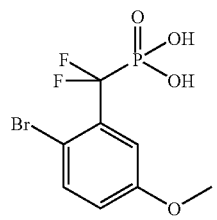

Diethyl (2-bromo-5-methoxyphenyl)oxomethylphosphonate was synthesized according to Example 82 from commercially available 2-bromo-5-methoxybenzoyl chloride. The product was used for the subsequent step without purification. Diethyl (2-bromo-5-methoxyphenyl)difluoromethylphosphonate was synthesized from the corresponding oxo-phosphonate using Example 80C. Compound 92 was synthesized according to procedures similar to those of Example 40 from this corresponding diethyl phosphonate. Compound 92 was purified by chromatography on a C-18 column eluted with 0-40% MeCN—H$_2$O (containing 0.05% formic acid). MS (ES–): m/z 315.0, 316.9 (M–H). $^1$H NMR: (DMSO-d$_6$, 400 MHz) δ 7.59 (d, J=8.6, 1H), 7.11 (d, J=2.4, 1H), 6.98-7.01 (m, 1H), 3.75 (s, 3H).

Example 93

Synthesis of Compound 93

(2-Bromo-5-ethoxyphenyl)difluoromethylphosphonic acid

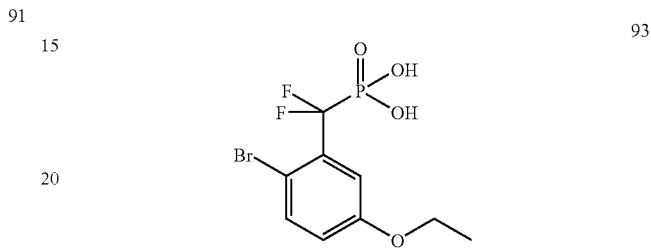

2-Bromo-5-hydroxybenzaldehyde (0.96 g, 4.8 mmol) was dissolved in anhydrous DMSO (10 mL). Iodoethane (0.50 mL, 6.2 mmol) and Cs$_2$CO$_3$ (1.9 g, 6.3 mmol) were added and the mixture stirred at room temperature for 1.5 hours. Additional Cs$_2$CO$_3$ (1.45 g, 4.8 mmol) was added to the reaction mixture and then was stirred for 30 minutes. The reaction mixture was diluted with H$_2$O and EtOAc and the layers were separated. Brine was added to the aqueous layer and it was extracted twice with EtOAc. The combined organics were washed with 1M NaOH twice and brine thrice, and then was dried over MgSO$_4$. The solution was vacuum-filtered through Celite® and concentrated in vacuo to give 1.08 g of 2-bromo-5-ethoxybenzaldehyde. 2-Bromo-5-ethoxy-benzaldehyde (1.02 g, 4.45 mmol) was dissolved in anhydrous toluene (10 mL) under N$_2$. Diethyl phosphite (0.57 mL, 4.4 mmol), then MgO (0.45 g, 11.2 mmol) was added and the N$_2$ inlet was removed. The mixture was stirred at room temperature for 1.75 hours, and more diethyl phosphite (0.1 mL, 0.77 mmol) was then added. The mixture was stirred for an additional 2.75 hours, then diluted with EtOAc, H$_2$O, and saturated aqueous NaHCO$_3$. The layers were separated and the organic layer was washed with brine, dried over MgSO$_4$, vacuum-filtered through Celite® and conc in vacuo to give 1.70 g of crude material. The product was used without purification. Diethyl (2-bromo-5-ethoxyphenyl)-(hydroxy)-methyl-phosphonate (1.13 g, 3.08 mmol) was dissolved in anhydrous dichloromethane (13 mL). Pyridinium chlorochromate (1.22 g, 4.6 mmol) was added and the mixture was stirred at room temperature for 17 hours at which time additional pyridinium chlorochromate (1.1 g, 5.1 mmol) was added. The mixture was stirred at room temperature for 3 hours, and then was refluxed for 45 minutes under a drying tube. The reaction was diluted with dichloromethane and washed with H$_2$O and saturated aq. NaHCO$_3$, dried over MgSO$_4$, vacuum-filtered through Celite® and concentrated in vacuo. The product was chromatographed (EtOAc-hexanes) to give diethyl (2-bromo-5-ethoxyphenyl)-oxomethylphosphonate. The diethyl (2-bromo-5-ethoxyphenyl)oxo-methyl-phosphonate was reacted with DAST according to Example 80C to give diethyl (2-bromo-5-ethoxyphenyl)difluoromethylphosphonate. Compound 93 was synthesized according to procedures similar to those of Example 40 from this corresponding diethyl phosphonate. MS (ES–): m/z 329.0, 331.0 (M–H). $^1$H NMR: (DMSO-d$_6$, 400 MHz) δ 7.56 (d, J=8.8, 1H), 7.11 (d, J=2.7, 1H), 6.97 (dd, J=2.7, 8.8, 1H), 4.01 (q, J=7.2, 2H), 1.30 (t, J=7.2, 3H).

Example 94

Synthesis of Compound 94

(2-Bromo-5-iodophenyl)difluoromethylphosphonic acid

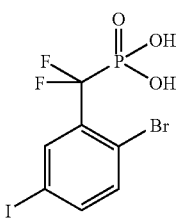

94

2-Bromo-5-iodobenzoic acid was converted to 2-bromo-5-iodobenzoyl chloride following procedures similar to those in Example 82A. The 2-bromo-5-iodobenzoyl chloride was reacted with triethyl phosphite following procedures similar to those in Example 82 to give diethyl (2-bromo-5-iodophenyl)oxomethylphosphonate. The diethyl (2-bromo-5-iodophenyl)oxomethylphosphonate was converted to diethyl (2-bromo-5-iodophenyl)difluoromethylphosphonate following procedures similar to those in Example 80C. Compound 94 was synthesized according to procedures similar to those of Example 40 from this corresponding diethyl phosphonate. MS (ES−): m/z 411.0, 413.0 (M−H). $^1$H NMR: (DMSO-d$_6$, 400 MHz) δ 7.93 (s, 1H), 7.67-7.69 (m, 1H), 7.45 (d, J=8.2, 1H).

Example 95

Synthesis of Compound 95

(2-Iodo-4-methylphenyl)difluoromethylphosphonic acid

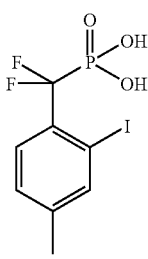

95

Commercially available 4-iodo-3-nitrotoluene was reacted with diethyl bromodifluoromethylphosphonate under Cd coupling conditions using Example 25 to yield diethyl (4-methyl-2-nitrophenyl)difluoromethylphosphonate. The diethyl (4-methyl-2-nitrophenyl)difluoromethylphosphonate (500 mg, 1.55 mmol) was dissolved in EtOAc (10 mL) and EtOH (10 mL). Five percent Pd—C (approximately 20 mg) was added and the mixture placed under H$_2$ (1 atm.) and stirred at room temperature overnight. The mixture was then filtered and concentrated in vacuo to give diethyl (4-methyl-2-aminophenyl)difluoromethylphosphonate. The diethyl (4-methyl-2-amino-phenyl)difluoromethylphosphonate was converted to diethyl (2-iodo-4-methylphenyl)-difluoromethylphosphonate using Example 86. Compound 95 was synthesized from this corresponding diethyl phosphonate using procedures similar to those of Example 40. MS (ES−): m/z 347.1 (M−H). $^1$H NMR: (CD$_3$OD, 400 MHz) δ 7.90 (s, 1H), 7.49 (dd, J=0.8, 8.2, 1H), 7.27 (d, J=8.2, 1H), 2.31 (s, 3H).

Example 96

Synthesis of Compound 96

[4-(Difluoro-phosphonomethyl)phenyl]acetic acid benzyl ester

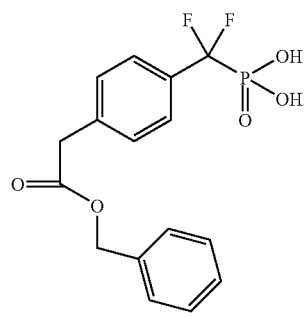

[4-(Difluoro-phosphono-methyl)-phenyl]-acetic acid benzyl ester

Compound 96 was prepared from 4-iodophenylacetic acid benzyl ester using procedures similar to those of Example 25 and 40. MS (ion spray): m/z 355.2 (M−H); 357.3 (M+H). $^1$H NMR: (DMSO-d$_6$, 400 MHz) δ 7.48-7.31 (m, 9H), 5.12 (s, 2H), 3.81 (s, 2H).

Example 97

Synthesis of Compound 97

[4-(Difluoro-phosphonomethyl)phenyl]acetic acid

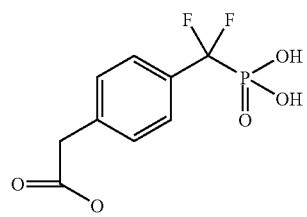

[4-(Difluoro-phosphono-methyl)-phenyl]-acetic acid

To Compound 96 (358 mg, 1.0 mmole) in 5 mL of MeOH was added 100 mg of 5% palladium/carbon. This solution was stirred under an atmosphere of H$_2$ gas for 2 hours. Filtration over a bed of Celite® followed by evaporation to dryness gave 269 mg of Compound 97. MS (ion spray): m/z 265.2 (M−H); 267.3 (M+H); $^1$H NMR: (DMSO-d$_6$, 400 MHz) δ 7.45 (d, 2H), 7.31 (d, 2H), 3.61 (s, 2H).

Example 98

Synthesis of Compound 98

3-{3-Bromo-4-[(diethoxyphosphoryl)difluoromethyl]phenyl}-2-methanesulfonyl-aminopropionic acid

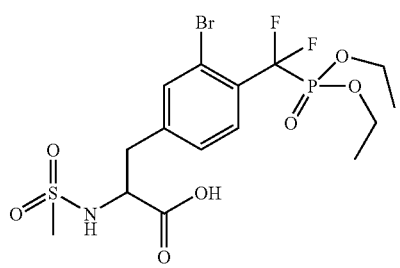

To tert-Butyl diphenyliminoglycine (0.68 g, 0.0023 mole), (−)-O-9-allyl-N-9-anthracenylmethyl cinchonidium bromide (0.14 g, 0.00023 mole) and CsOH.H$_2$O (3.86 g, 0.023 mole) at −78° C. was added DCM (8 mL). To this suspension was then added a solution of the (2-bromo-4-bromomethyl-phenyl)-difluoro-methylphosphonic acid diethyl ester (Compound 26) (1.5 g, 0.0034 mole) in DCM (6 mL) in one portion and the reaction was vigorously stirred for 24 hours at −78° C. The reaction was diluted with Et$_2$O (400 mL) and the Et$_2$O layer was washed with H$_2$O (2×150 mL), brine (150 mL) and dried over MgSO$_4$ for 15-20 min. Filtration and solvent evaporation left behind 2.1 g of crude product. Flash chromatography using silica gel (100 mL) and 20% ethyl acetate/hexanes afforded (2S)-{4-[2-benzhydrylideneamino-2-(tert-butoxycarbonyl)-ethyl]-2-bromo-phenyl}-difluoromethylphosphonic acid diethyl ester (1.35 g). The intermediate (2S)-{4-[2-Benzhydrylideneamino-2-(tert-butoxycarbonyl)ethyl]-2-bromo-phenyl}-difluoro-methylphosphonic acid diethyl ester was prepared on a larger scale (12.3 g, 18.9 mmole) and was dissolved in 30 mL of THF/H$_2$O/CH$_3$COOH (1:1:1) and stirred at room temperature for 3 hours. Water (100 mL) was added followed by neutralization to pH=8 with saturated NaHCO$_3$. This mixture was then extracted with 2×200 mL of EtOAc. The combined organic layers were dried over Na$_2$SO$_4$ and evaporated to dryness. This mixture was dissolved in 100 mL of anhydrous CH$_2$Cl$_2$ with stirring under nitrogen. Methyl morpholine 3.82 g. (37.8 mmole) was added followed by 3.25 g (28.4 mmole) of methanesulfonyl chloride and this mixture was stirred at room temperature overnight. The mixture was then extracted with 100 mL of 1N HCl, dried over Na$_2$SO$_4$ and evaporated. Column chromatography (20% EtOAc/CH$_2$Cl$_2$) gave 3-{3-bromo-4-[(diethoxyphosphoryl)difluoromethyl]phenyl}-2-methanesulfonylamino-propionic acid t-butyl ester (8.0 g). This material was stirred in 50 mL of 30% TFA/CH$_2$Cl$_2$ for 3 hours, followed by evaporation to dryness to give approximately 7 g of Compound 98. $^1$H NMR: (DMSO-d$_6$, 400 MHz) δ 7.72-7.69 (m, 2H), 7.51 (dd, 1H), 7.43 (d, 1H), 4.10 (m, 5H), 3.08 (dd, 1H), 2.82 (dd, 1H), 2.66 (s, 3H). 1.21 (t, 6H).

Compound 98 can be converted into the corresponding free phosphonic acid using procedures similar to those of Example 40.

Example 99

Synthesis of Compound 99

{[2-Bromo-4-(2-carbamoyl-2-methanesulfonylaminoethyl)phenyl]difluoromethyl}-phosphonic acid

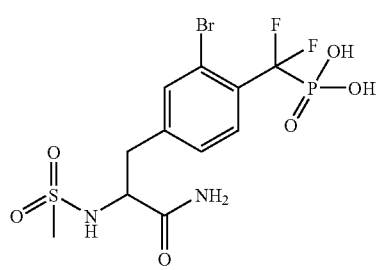

Compound 98 (254 mg, 0.5 mmole) was stirred in 5 mL of 25% oxalyl chloride containing 1 drop of DMF for 3 hours. This mixture was evaporated to dryness and 5 mL of anhydrous THF was added followed by evaporation to dryness to remove residual oxalyl chloride. The residue was dissolved in 2 mL of anhydrous THF and then 3 mL of 2M NH$_3$ in MeOH was added. After stirring at room temperature for 2 hours, the mixture was evaporated to dryness. Column chromatography (4% MeOH, CH$_2$Cl$_2$) gave 153 mg of {[2-bromo-4-(2-carbamoyl-2-methanesulfonylaminoethyl)-phenyl]-difluoromethyl}-phosphonic acid diethyl ester. This material was converted to Compound 99 using the procedures similar to those of Example 40. MS (ion spray): m/z 450.2/452.2 (M−H); 452.2/454.1 (M+H). $^1$H NMR: (MeOD-d$_3$, 400 MHz) δ 7.70 (s, 1H), 7.59 (dd, 1H), 7.40 (d, 1H), 4.16 (m, 1H), 3.13 (dd, 1H), 2.87 (dd, 1H), 2.54 (s, 3H).

Example 100

Synthesis of Compound 100

{[2-Bromo-4-(2-methanesulfonylamino-2-methylcarbamoylethyl)phenyl]difluoromethyl}phosphonic acid

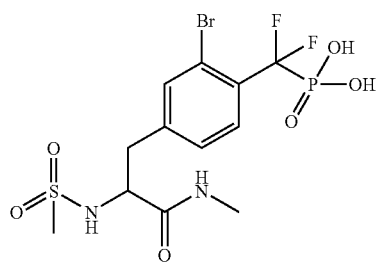

Compound 100 was prepared using a similar procedure to Compound 99 except that 2M methylamine in THF was used. MS (ion spray): m/z 464.2/466.2 (M–H); 466.2/468.1 (M+H). $^1$H NMR: (DMSO-d$_6$, 400 MHz) δ 8.03 (q, 1H), 7.60 (s, 1H), 7.55 (d, 1H), 7.48 (d, 1H), 7.31 (d, 1H), 3.95 (m, 1H), 2.89 (dd, 1H), 2.71 (dd, 1H), 2.55 (d, 3H), 2.54 (s, 3H).

Example 101

Synthesis of Compound 101

{[2-Bromo-4-(2-dimethylcarbamoyl-2-methanesulfonylamino-ethyl)-phenyl]-difluoromethyl}-phosphonic acid

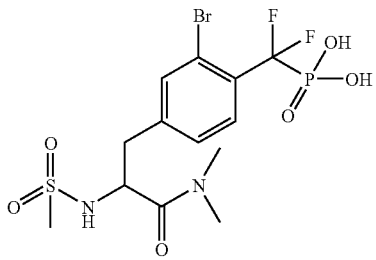

101

Compound 101 was prepared using a similar procedure to Compound 99 except that 2M dimethylamine in THF was used. MS (ion spray): m/z 478.2/480.2 (M–H); 480.2/482.1 (M+H). $^1$H NMR: (DMSO-d$_6$, 400 MHz) δ 7.64 (s, 1H), 7.55 (d, 1H), 7.50 (d, 1H), 7.38 (d, 1H), 4.49 (m, 1H), 2.94 (s, 3H), 2.92 (dd, 1H), 2.80 (s, 3H), 2.75 (dd, 1H), 2.65 (s, 3H).

Example 102

Synthesis of Compound 102

[(2-Bromo-3,4-dimethylphenyl)difluoromethyl]phosphonic acid

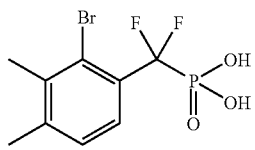

102

[(2-Bromo-3,4-dimethyl-phenyl)-difluoro-methyl]-phosphonic acid
C$_9$H$_{10}$BrF$_2$O$_3$P
Mol. Wt.: 315.05

To a solution of 2-bromo-3,4-dimethylnitrobenzene (1.0 g, 4.35 mmole) in 10 mL DMF was added SnCl$_2$.2H$_2$O (4.92 g, 21.8 mmole). This solution was stirred overnight at room temperature 50 mL of H$_2$O was added and the pH was adjusted to 8 with the addition of sat. NaHCO$_3$ and extracted with 150 mL of EtOAC. The organic layer was dried over Na$_2$SO$_4$, filtered and evaporated yielding 2-bromo-3,4-dimethylaniline which was used as is in the conversion to 2-bromo-3,4-dimethyliodobenzene in a similar manner to that of Example 86. Compound 102 was prepared from 2-bromo-3,4-dimethyliodo-benzene using procedures similar to those of Examples 25 and 40. MS (ion spray): m/z 314.0/316.1 (M–H); 316.1/318.0 (M+H). $^1$H NMR: (DMSO-d$_6$, 400 MHz) δ 7.37 (d, 1H), 7.15 (d, 1H), 2.43 (s, 3H), 2.37 (s, 3H).

Example 103

Synthesis of Compound 103

[(2-Bromo-3-methylphenyl)difluoromethyl]phosphonic acid

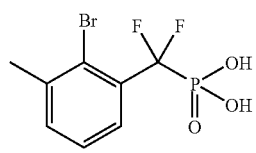

103

[(2-Bromo-3-methyl-phenyl)-difluoro-methyl]-phosphonic acid
C$_8$H$_8$BrF$_2$O$_3$P
Mol. Wt.: 301.02

Compound 103 was prepared from 2-bromo-3-methyliodobenzene using procedures similar to those of Examples 25 and 40. MS (ion spray): m/z 300.0/302.1 (M–H); 302.1/304.0 (M+H). $^1$H NMR: (DMSO-d$_6$, 400 MHz) δ 7.54 (dd, 1H), 7.45-7.40 (m, 2H), 2.41 (s, 3H).

Example 104

Synthesis of Compound 104

[(2-Bromo-4-isopropylphenyl)difluoromethyl]phosphonic acid

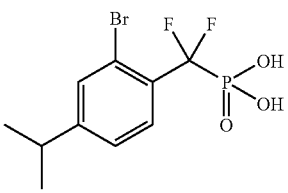

104

[(2-Bromo-4-isopropyl-phenyl)-difluoro-methyl]-phosphonic acid
C$_{10}$H$_{12}$BrF$_2$O$_3$P
Mol. Wt.: 329.08

2-Bromo-4-isopropyliodobenzene was prepared from 2-bromo-4-isopropylaniline using procedures similar to those in Example 86. Compound 104 was prepared from 2-bromo-4-isopropyliodobenzene using procedures similar to those of Examples 25 and 40. MS (ion spray): m/z 328.1/330.1 (M–H); 330.1/332.1 (M+H). $^1$H NMR: (DMSO-d$_6$, 400 MHz) δ 7.55 (d, 1H), 7.51 (dd, 1H), 7.35 (d, 1H), 2.91 (m, 1H), 1.18 (d, 6H).

Example 105

Synthesis of Compound 105

{[2-Bromo-4-(2-methane sulfonylamino-2-methyl-carbamoylethyl)phenyl]difluoromethyl}phosphonic acid

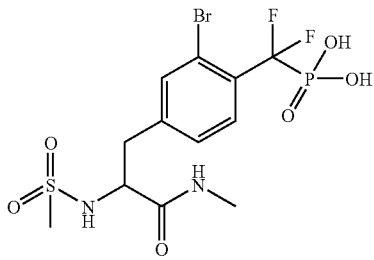

To make the D-isomer of Compound 100, the procedure in Example 98 was used except (+)-O-9-allyl-N-9-anthracenyl-methyl cinchoninium bromide was used as the phase transfer catalyst in the alkylation step to give the (2R)-{4-[2-benzhy-drylideneamino-2-(tert-butoxycarbonyl)-ethyl]-2-bromo-phenyl}difluoromethyl-phosphonic acid diethyl ester. The final compound was then synthesized using a procedure similar to Example 100.

Example 106

PTP Enzymatic Activity Assay

Assays of PTP activity using a tyrosine phosphorylated $^{32}$P-labeled EGF (Epidermal Growth Factor) receptor autophosphorylation site peptide as substrate were performed essentially as described (Flint et al., 1993 *EMBO J.* 12:1937-1946; Zhang et al., 1994 *Biochem.* 33:2285-2290, specific activity 11 uCi/nM).

Aliquots (20 μL) of compound diluted from 100% DMSO stock solutions into 25 mM Tris-pH 7.5 containing 6% DMSO were distributed into V-bottomed wells of a 96-well polypropylene microtiter plate; control wells received Tris-DMSO containing no compound. A 20 uL aliquot of assay buffer (25 mM Tris-pH 7.5, 1 mM EDTA, 3 mM dithiothreitol (DTT), 0.3 mg/mL ovalbumin) was added to wells designated as enzyme negative controls. The $^{32}$P-labeled substrate peptide (diluted to 0.6 μM in assay buffer without DTT) was added to all wells in 20 μL aliquots. The plate was agitated for 20 seconds on an orbital shaker and incubated for 13 minutes at room temperature. PTP1B (diluted into ice-cold assay buffer from a 50% glycerol stock such that this amount of enzyme would utilize less than 20% of the substrate in the assay), was added (20 μl per well) to all wells except enzyme negative control wells. The plate was agitated and incubated an additional 13 minutes at room temperature. 140 μL of an activated charcoal suspension (25 mg/mL in 0.1 M NaH$_2$PO$_4$, pH≦5) was added to each well, the contents mixed by vortexing, and the plate centrifuged 2400 rpm for 3 minutes at room temperature in a tabletop centrifuge (Beckman Instruments, Inc.). 100 μL aliquots of the resulting supernatant in each well was transferred to a beta-scintillation counting plate (Perkin Elmer, Inc.) and $^{32}$P beta emissions were quantified according to the manufacturer's recommendations. After subtracting background counts, correcting for enzyme negative control values, and normalizing to control wells that received no compound, compound concentrations at which 50% of the maximal enzyme activity was inhibited (IC$_{50}$) were calculated.

Example 107

Assay for Compound Efficacy in Cells: Insulin Receptor Tyrosine Phosphorylation Insulin receptor tyrosine phosphorylation (IR PY) was evaluated by an ELISA, using 293-HEK cells overexpressing the human insulin receptor (293/IR cells). 293/IR cells growing in 96-well plates at 37° C. with 5% CO$_2$ were serum-starved for 16 hours, pretreated with various concentrations of compounds for 2 hours, and then exposed to 3 nM insulin for an additional 10 minutes. The cells were then removed from the incubator and lysed in extraction buffer (50 mM Tris-HCl, pH 7.5 (room temperature); 2 mM EDTA, pH 7-8; 1 mM phosphate (polyphosphate); 1 mM NaVO$_4$ (pH 10, monomeric); 0.1% Triton X-100; Protease Inhibitor Cocktail set III, (Calbiochem, San Diego, Calif.)) at 4° C. for 20 minutes with agitation. The IR PY ELISA was performed as follows: Dynex Immulon HB4X plates were coated with anti-insulin receptor antibody Ab-1 (NeoMarkers, Inc., Fremont, Calif.) in phosphate buffered saline (PBS)+5 μg/mL bovine serum albumin. The plates were subsequently blocked with 3% bovine serum albumin in PBS. Cell lysates were transferred to the ELISA plate wells and incubated at 23° C. for 1 hr with agitation. The wells were washed three times with TBST (20 mM Tris-HCl, pH 7.5; 150 mM NaCl; 0.05% Tween 20). An anti-phosphotyrosine antibody conjugated to horseradish peroxidase (4G10-HRP, www.upstate.com) diluted in TBST was incubated with the wells at 23° C. for 1 hour with agitation. The plates were washed three more times with TBST prior to colorimetric detection of horseradish peroxidase with 3,3',5,5'-Tetramethylbenzidine Liquid Substrate System (Sigma-Aldrich, Inc, St. Louis, Mo.).

We claim:
1. A compound of Formula IIe:

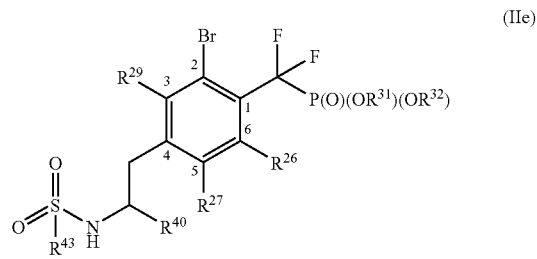

wherein R$^{26}$, R$^{27}$ and R$^{29}$ are each independently H, halo, —OH, —NO$_2$, —CN, —CF$_3$, —CHF$_2$, —CH$_2$CH$_3$, —CH$_2$CF$_3$, —CF$_2$CF$_3$, —CH$_2$Cl, —CH$_2$OH, —CH$_2$CH$_2$OH, —CH$_2$NH$_2$, —CH$_2$CH$_2$NH$_2$, —CH$_2$SO$_2$CH$_3$, —OR$^{23}$, —C(O)R$^{23}$, —C(O)OR$^{23}$, —C(O)N(R$^{23}$)(R$^{24}$), —OC(O)R$^{23}$, —OC(O)OR$^{23}$, —OC(O)N(R$^{23}$)(R$^{24}$), —N(R$^{23}$)(R$^{24}$), —S(O)$_2$R$^{23}$, —S(O)R$^{23}$, —SR$^{23}$, —S(O)$_2$N(R$^{23}$)(R$^{24}$); —NR$^{23}$C(O)R$^{24}$, —NR$^{23}$C(O)OR$^{24}$, —NR$^{23}$SOOR$^{24}$, —NR$^{23}$C(O)N(R$^{24}$)(R$^{25}$), —NR$^{23}$SO$_2$R$^{24}$, —NR$^{23}$SO$_2$N(R$^{24}$)(R$^{25}$) or optionally substituted C$_{1-6}$ alkyl, C$_{1-6}$ alkoxy, or aryl; where R$^{23}$, R$^{24}$ and R$^{25}$ are each independently H, C$_{1-4}$ alkyl or C$_{3-8}$ cycloalkyl or aryl;

$R^{31}$ and $R^{32}$ are each independently H, alkyl or $C_{5-6}$ aryl;

$R^{40}$ is H, alkyl, alkylene, —C(O)OR$^{39}$, —C(O)N(R$^{37}$)(R$^{38}$) or —N(NH$_2$)C(O)NH(CH$_2$)$_n$Ph;

$R^{37}$ and $R^{38}$ are each independently H, —C(O)OR$^{39}$, —C(O)cycloalkyl-Ph, —S(O)$_2$R$^{39}$, —C(O)R$^{39}$, —OC(O)R$^{39}$, —C(O)(CH$_2$)$_q$R$^{39}$, —S(O)$_2$, —S(O)$_2$NHR$^{39}$, —S(O)$_2$N(R$^{44}$)(R$^{39}$), —N(R$^{44}$)(R$^{39}$), —C(O)N(R$^{44}$)(R$^{39}$) or —NHC(O)N(R$^{44}$)(R$^{39}$); or optionally substituted $C_{1-6}$ alkyl, $C_{3-8}$ cycloalkyl or $C_{5-8}$ aryl;

$R^{39}$ is H or optionally substituted $C_{1-6}$ alkyl or aryl;

$R^{43}$ is H, —NHR$^{39}$ or R$^{39}$;

wherein n is an integer from 0 to 4; and wherein each of the phenyl carbon atoms 3, 5 or 6 including its respective substituents are optionally replaced by N; or phenyl carbons atoms 5 and 6 and their respective substituents are optionally replaced by S, N or O; or a pharmaceutically acceptable salt, ester or prodrug thereof.

2. The compound of claim 1, wherein $R^{26}$, $R^{27}$ and $R^{29}$ are each H; $R^{40}$ is —C(O)NR$^{37}$R$^{38}$; $R^{43}$ is H or —NH$_2$; or optionally substituted $C_{1-6}$ alkyl or $C_{3-8}$ aryl; or a pharmaceutically acceptable salt, ester or prodrug thereof.

3. The compound of claim 2 wherein $R^{37}$ is H; $R^{38}$ is optionally substituted $C_{1-6}$ alkyl; and $R^{43}$ is optionally substituted $C_{1-6}$ alkyl or aryl.

* * * * *